(12) United States Patent
Fisher et al.

(10) Patent No.: US 7,229,822 B1
(45) Date of Patent: Jun. 12, 2007

(54) MELANOMA DIFFERENTATION ASSOCIATED GENE-5 AND VECTORS AND CELLS CONTAINING SAME

(76) Inventors: Paul B. Fisher, 15 Gordon Pl., Scarsdale, NY (US) 10583; Dong-Chul Kang, 200 Union Ave., Apt. A, Rutherford, NJ (US) 07070; Rahul V. Gopalkrishnan, 302 W. 79 St., Apt. 2A, New York, NY (US) 10024

( * ) Notice: Subject to any disclaimer, the term of this patent is extended or adjusted under 35 U.S.C. 154(b) by 0 days.

(21) Appl. No.: 09/515,363

(22) Filed: Feb. 29, 2000

(51) Int. Cl.
   C12N 15/63    (2006.01)
   C12N 15/85    (2006.01)
   C07H 21/04    (2006.01)

(52) U.S. Cl. .................. 435/320.1; 435/325; 536/23.1
(58) Field of Classification Search ............... 536/23.4; 435/455, 325
   See application file for complete search history.

(56) References Cited

U.S. PATENT DOCUMENTS

| | | | |
|---|---|---|---|
| 5,399,346 | A | 3/1995 | Anderson et al. |
| 5,643,761 | A | 7/1997 | Fisher et al. |
| 5,912,236 | A | 6/1999 | Xu et al. |
| 6,025,127 | A | 2/2000 | Sidransky et al. |
| 6,051,376 | A | 4/2000 | Fisher et al. |
| 2002/0048763 | A1 | 4/2002 | Penn et al. |

FOREIGN PATENT DOCUMENTS

| | | |
|---|---|---|
| EP | 336523 | 10/1989 |
| WO | WO90/11092 | 10/1990 |
| WO | WO93/23034 | 11/1993 |
| WO | WO95/11986 | 5/1995 |
| WO | WO 01/85955 | 11/2001 |

OTHER PUBLICATIONS

A74554, Oct. 15, 1999.*
A77533, Oct. 19, 1999.*
Brenner (1999) Trends in Genetics 15:132-133.*
Doerks (1998) Trends in Genetics 14:248-250.*
Scott et al (1999) Nature Genetics 21:440-443.*
Fisher, P.B. and S. Grant, *Effects of Interferon On Differentiation Of Normal And Tumor Cells, Pharmacology & Therapeutics*, (1985) 27(2):143-66 (Exhibit B).
Hofmann, K., P. Bucher and J. Tschopp, *The CARD Domain: A New Apoptic Signalling Motif. Trends Biochem. Sci.*, (1997) 22(5):155-6. (Exhibit C).
Huang, F., et al., *Differentation Induction Subtraction Hybridization (DISH): A Strategy For Cloning Genes Displaying Differential Expression During Growth Arrest And Terminal Differentiation*, Gene. (1999) 236(1):125-31 (Exhibit D).
Huang, F., et al., *Identification And Temporal Expression Pattern Of Genes Modulated During Irreversible Growth Arrest And Terminal Differentiation In Human Melanoma Cells*, Oncogene, (1999) 18(23):3546-52 (Exhibit E).

Jiang, H. and P.B. Fisher, *Use Of A Sensitive And Efficient Subtraction Hybridization Protocol For The Identification Of Genes Differentially Regulated During The Induction Of Differentiation In Human Melanoma Cells, Molecular Cellular Differentiation*, (1993) 1(3): 285-299 (Exhibit F).
Jiang, H., et al., *Subtraction Hybridization Identifies A Novel Melanoma Differentiation Associated Gene, mda-7, Modulated During Human Melanoma Differentiation, Growth and Progression*, Oncogene, (1985) 11(12): 2477-86 (Exhibit G).
Jiang, H., et al., *The Melanoma Differentiation-Associated Gene mda-6, Which Encodes The Cyclin-Dependent Kinase Inhibitor p21, Is DIfferentially Expressed During Growth, Differentiation And Progression In Human Melanoma Cells, Oncogene*, (1985) 10(9): 1855-64 (Exhibit H).
Jiang, H., et al., *Gene Expression Changes Associated With Reversible Growth Suppression And The Induction Of Terminal Differentiation In Human Melanoma Cells, Molecular Cellular Differentiation*, (1993) 1(1):41-66 (Exhibit I).
Jiang, H., S. Waxman and P.B. Fisher, *Regulation Of c-fos, c-jun And jun-B Gene Expression In Human Melanoma Cells Induced To Terminally Differentiate, Molecular Cellular Differentiation*, (1993) 1(2): 197-214 (Exhibit J).
Jiang, H., et al., *The Melanoma Differentiation Associated Gene mda-7 Suppresses Cancer Cell Growth, Proceedings of the National Academy of Sciences of the United States of America*, (1996) 93(17): 9160-5 (Exhibit K).
Jiang, H., et al., *The Melanoma Differentiation Associated Gene-6 (mda-6), Which Encodes The Cyclin-Dependent Kinase Inhibitor p21, May Function As A Negative Regulator Of Human Melanoma Growth And Progression, Molecular Cellular Differentiation*, (1996) 4(1): 67-89 (Exhibit L).
Lin, J. J., H. Jiang and P.B. Fisher, *Melanoma Differentiation Associated Gene-9, mda-9, Is A Human Gamma Interferon Responsive Gene, Gene*, (1988) 207(2): 105-10 (Exhibit M).
Luking, A., U. Stahl and U. Schmidt, *The Protein Family Of RNA Helicases, Crit. Rev. Biochem. Mol. Biol.*, (1998) 33(4): 259-96 (Exhibit N).
Rani, M.R.S., et al. *Characterization Of Beta-R1, A Gene That Is Selectively Induced By Interferon Beta (IFN-beta) Compared With IFN-alpha, J. Biol. Chem.*, (1996) 271(37): 22878-84 (Exhibit O); and.
Su, Z.-z., Y. Shi and P.B. Fisher, *Subtraction Hybridization Identifies A Transformation Progression-Associated Gene PEG-3 With Sequence Homology To A Growth Arrest And DNA Damage-Inductible Gene, Proc. Natl. Acad. Sci. USA*, (1997) 94(17): 9125-30 (Exhibit P).

(Continued)

*Primary Examiner*—Celine Qian
(74) *Attorney, Agent, or Firm*—Baker Botts LLP

(57) ABSTRACT

The invention provides for isolated nucleic acids encoding an Mda-5 polypeptide as shown in SEQ ID NO:1. The invention also provides for isolated nucleic acids comprising derivatives of the sequence of SEQ ID NO:1 that encode polypeptides functionally equivalent to Mda-5. The invention further provides for fragments of the isolated nucleic acid of SEQ ID NO:1 that encode polypeptides having Mda-5 biological activity. Vectors comprising these isolated nucleic acids and host cells comprising these vectors are also provided by the instant invention.

10 Claims, 32 Drawing Sheets

OTHER PUBLICATIONS

Kawai T, et al. (2005) IPS-1, an adaptor triggering RIG-I- and Mda5-mediated type I interferon induction. Nat Immunol. 6(10):981-8. Epub Aug. 28, 2005.

Meylan, E, et al. (2005) Cardif is an adaptor protein in the RIG-I antiviral pathway and is targeted by hepatitis C virus. Nature. 437(7062):1167-72. Epub Sep. 21, 2005.

Kang et al., (2004) Expression analysis and genomic characterization of human melanoma differentiation associated gene-5, mda-5: a novel type I interferon-responsive apoptosis-inducing gene. Oncogene 23(9):1789-800.

Cocude et al. (2003) A novel cellular RNA helicase, RH116, differentially regulates cell growth, programmed cell death and human immunodeficiency virus type 1 replication. J Gen Virol. 84(Pt 12):3215-25.

Kovacsovics M, et al. (2002) Overexpression of Helicard, a CARD-containing helicase cleaved during apoptosis, accelerates DNA degradation. Curr Biol. May 14, 2002; 12(10):838-43.

Nagano M, et al. (2001) Point mutation (-69 G→A) in the promoter region of cholesteryl ester transfer protein gene in Japanese hypoeralphalipoproteinemic subjects. Arterioscler Thromb Vasc Biol. Jun;21(6):985-90.

Brenner SE (1999) Errors in genome annotation. TIG 15(4):132-133.

Huang et al., (1999) Identification and temporal expression pattern of genes modulated during irreversible growth arrest and terminal differentiation in human melanoma cells. Oncogene 18:3546-3552.

Huang et al., (1999) Differentiation induction subtraction hybridization (DISH): a strategy for cloning genes displaying differential expression during growth arrest and terminal differentiation. Gene 236:125-131.

Scott et al., (1999) The Pendred syndrome gene encodes a chloride-iodide transport protein. Nat. Genet. 21:440-443.

Sibson et al., (1999) Genbank Sequence Accession No. A74554, 377 bp linear DNA from International Patent Application No. WO 9401548, sequence release date Oct. 15, 1999.

Sibson et al., (1999) Genbank Accession No. A77533, 377 bp linear DNA from European Patent Application No. EP 0587279, sequence released Oct. 19, 1999.

Adams MD (1998), Accession No. AQ284992, and corresponding Homology Comparison RESULT #1.

Doerks, T, Bairoch A, Bork P (1998) Protein annotation: detective work for function prediction. TIG 14(6):248-250.

Lin JJ, Jiang H, Fisher PB (1998) Melanoma differentiation associated gene-9, mda-9, is a human gamma interferon responsive gene. Gene 207(2):105-110.

Lüking A, Stahl U, Schmidt U (1998) The protein family of RNA helicases. Crit. Rev. Biochem. Mol. Biol. 33(4):259-296.

Hofmann K, Bucher P, Tschopp J (1997) The CARD domain: a new apoptotic signalling motif. Trends Biochem. Sci. 22(5):155-156.

Su ZZ, Shi Y, Fisher PB (1997) Subtraction hybridization identifies a progression elevated gene PEG-3 with sequence homology to a growth arrest and DNA damage inducible gene. Proc. Natl. Acad. Sci. USA 94:9125-9130.

Jiang H, Lin J, Su ZZ, Fisher PB (1996) The melanoma differentiation associated gene-6 (mda-6), which encodes the cyclin-dependent kinase inhibitor p21, may function as a negative regulator of human melanoma growth and progression. Mol. Cell. Different. 4:67-89.

Jiang H, Su ZZ, Lin JJ, Goldstein NI, Young CSH, Fisher PB (1996) The melanoma differentiation associated gene mda-7 suppresses cancer cell growth. Proc. Natl. Acad. Sci. USA 93:9160-9165.

Rani MR, Foster GR, Leung S, Leaman D, Stark GR, Ransohoff RM (1996) Characterization of beta-R1, a gene that is selectively induced by inteferon beta (IFN-beta) compared with IFN-alpha. J. Biol. Chem. 271(37):22878-22884.

Jiang H, Lin J, Su ZZ, Herlyn M, Kerbel RS, Weissman BE, Welch DR, Fisher PB (1995) The melanoma differentiation-associated gene mda-6, which encodes the cyclin-dependent kinase inhibitor p21, is differentially expressed during growth, differentiation, and progression in human melanoma cells. Oncogene 10:1855-1864.

Jiang H, Lin JJ, Su ZZ, Goldstein NI, Fisher PB (1995) Subtraction hybridization identifies a novel melanoma differentiation associated gene, mda-7, modulated during human melanoma differentiation, growth, and progression. Oncogene 11: 2477-2486.

Waxman, S., ed. (1995) Differentiation Therapy (Ares Serono Symposia Publications, Rome). vol. 10, pp. 1-531. (Table of Contents Only).

Ikeda RA, Ligman CM, Warshamana S. (1992). T7 promoter contacts essential for promoter activity in vivo. Nucleic Acids Res. May 25, 1992; 20(10):2517-24.

Felgner PL, Gadek TR, Holm M, Roman R, Chan HW, Wenz M, Northrop JP, Ringold GM, Danielson M (1987). Lipofection: a high efficient, lipid mediated DNA-transfection procedure, Proc. Natl. Acad. Sci. USA 84:7413-7417.

Rossi P, de Crombrugghe B (1987). Identification of a cell-specific transcriptional enhancer in the first intron of the mouse alpha 2 (type I) collagen gene. Proc. Natl. Acad. Sci. USA 84:5590-5594.

Ghosh-Choudhury G, Haj-Ahmad Y, Brinkley P, Rudy, J, Graham FL (1986). Human adenovirus cloning vectors based on infectious bacterial plasmids. Gene 50:161-171.

Kang DC, Gopalkrishnan RV, Jiang H, Wu Q, Fisher PB (2000). Melanoma differentation associated gene 5 (MDA-5): A novel interferon-inducible putative RNA helicase involved in cell survival. Proceedings of the American Association for Cancer Research 41:509-510 (Abstract #3250).

Bult CJ (1998). Putative ATP-dependent RNA helicase MJ1505. SwissProt Acc. No. Q58900.

Wood V et al. (1996). Putative helicase C188.13c. SwissProt Acc. No. Q09884.

Algate PA, Steelman LS, Mayo MW, Miyajima, A, McCubrey JA (1994). Regulation of the interleukin-3 (IL-3) receptor by IL-3 in the fetal liver-derived FL5.12 cell line. Blood 83:2459-2468.

Cluitmans FH, Esendam BH, Ladegent JE, Willemze R, Falkenburg JH (1994). IL-4 down-regulates IL-2, IL-3-, and GM-CSF-induced cytokine gene expression in peripheral blood monocytes. Ann. Hematol. 68:293-298.

de Wit H, Esselink MT, Halie MR, Vellenga E (1994). Differential regulation of M-CSF and IL-6 gene expression in monocytic cells. Br. J. Haematol. 86:259-264.

Jiang H, Lin J, Fisher PB (1994). A molecular definition of terminal differentiation in human melanoma cells. Mol. Cell. Different. 2:221-239.

Lagoo AS, Lagoo-Deenadayalan S, Lorenz HM, Byrne J, Barber WH, Hardy KJ (1994). IL-2, IL-4, and IFN-gamma gene expression versus secretion in superantigen-activated T cells. Distinct requirement for costimulatory signals through adhesion molecules. J. Immunol. 152;1641-1652.

Pang G, Couch L, Batey R, Clancy R, Cripps A (1994). GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. Clin. Exp. Immunol. 96:437-443.

Shimane M, Tani K, Maruyama K, Takahashi S, Ozawa K, Asano S (1994). Molecular cloning and characterization of G-CSF induced gene cDNA. Biochem. Biophys. Res. Commun. 199:26-32.

Wilson R et al. (1994). Endoribonuclease der-1. SwissProt Acc. No. P34529.

Martinez OM, Villanueva JC, Lake J, Roberts JP, Ascher NL, Krams SM (1993). IL-2 and IL-5 gene expression in response to alloantigen in liver allograft recipients 10 and in vitro. Transplantation 55:1159-1166.

Pizarro TT, Malinowska K, Kovacs EJ, Clancy J Jr, Robinson JA, Piccinini LA (1993). Induction of TNF alpha and TNF beta gene expression in rat cardiac transplants during allograft rejection. Transplantation 56:399-404.

Anderson WF (1992). The June RAC meeting. Hum. Gene Ther. 3:459-460.

Berkner KL (1992). Expression of heterologous sequences in adenoviral vectors. Curr. Top. Microbiol. Immunol. 158:39-66.

Breviario F, d'Aniello EM, Golay J, Peri G, Bottazzi B, Bairoch A, Saccone S, Marzella R, Predazzi V, Rocchi M, et al. (1992). Interleukin-1-inducible genes in endothelial cells. Cloning of a new gene related to C-reactive protein and serum amyloid P component. J. Biol. Chem. 267:22190-22197.

Espinoza-Delgado I, Longo, DL, Gusella GL, Varesio L (1992). Regulation of IL-2 receptor subunit genes in human monocytes. Differential effects of IL-2 and IFN-gamma. J. Immunol. 149:2961-2968.

LI YP, Stashenko P (1992). Proinflammatory cytokines tumor necrosis factor-alpha and IL-6, but not IL-1, down-regulate the osteocalcin gene promoter. J. Immunol. 148:788-794.

Mauviel A, Reitamo S, Remitz A, Lapiere JC, Ceska M, Baggiolini M, Walz, A, Evans CH, Uitto J (1992). Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. J. Immunol. 149:2969-2976.

Sprecher E, Becker Y (1992). Detection of IL-1 beta, TNF-alpha, and IL-6 gene transcription by the polymerase chain reaction in keratinocytes, Langerhans cells and peritoneal exudate cells during infection with herpes simplex virus-1. Arch. Virol. 126:253-269.

Canonico AE, Conary JT, Christman BW, Meyrick BO, Brigham KL (1991). Expression of a CMV promoter driven human α-1 antitrypsin gene in cultured lung endothelial cells and in the lungs of rabbits. Clin. Res. 39:219A (abstract).

Culver KW, Anderson WF, Blaese RM (1991). Lymphocyte gene therapy, Hum. Gene Ther. 2:107-109. Hazinski TA, Ladd PA, DeMatteo CA (1991). Localization and induced expression of fusion genes in the rat lung. Am. J. Respir. Cell Mol. Biol. 4:206-209.

Hazinski TA, Ladd PA, DeMatteo CA (1991). Localization and induced expression of fusion genes in the rat lung. Am. J. Respir. Cell Mol. Biol. 4:206-209.

Kay AB, Ying S, Varney V, Gaga M, Durham SR, Moqbel R, Wardlaw AJ, Hamid Q (1991). Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. J. Exp. Med. 173:775-778.

Rosenfeld MA, Siegfried W, Yoshimura K, Yoneyama K, Fukayama M, Stier LE, Paakko PK, Gilardi P, Stratford-Perricaudet LD, Perricaudet M, et al. (1991). Adenovirus-mediated transfer of a recombinant alpha 1-antitrypsin gene to the lung epithelium in vivo. Science 252:431-434.

Ulich TR, Guo KZ, Remick D, del Castillo J, Yin SM (1991). Endotoxin-induced cytokine gene expression in vivo. III. IL-6 mRNA and serum protein expression and the in vivo hematologic effects of IL-6. J. Immunol. 146:2316-2323.

Fisher PB, Rowley PT (1991). Regulation of growth, differentiation, and antigen expression in human tumor cells by recombinant cytokines: applications for the differentiation therapy of human cancer. In: Waxman S, Rossi GB, Takaku F, Eds. The Status of Differentiation Therapy of Cancer, vol. 2. *Serono Symposia Pubs.*, Raven Press, New York, pp. 201-214.

Anderson WF, Blaese RM, Culver K (1990). The ADA human gene therapy clinical protocol: Points to Consider response with clinical protocol, Jul. 6, 1990. Hum. Gene Ther. 1:331-362.

Geller AI, Keyomarsi K, Bryan J, Pardee AB (1990). An efficient deletion mutant packaging system for a defective herpes simplex virus vectors: potential applications to human gene therapy and neuronal physiology. Proc. Natl. Acad. Sci. USA 87:8950-8954.

Horisberger MA, McMaster GK, Zeller H, Wathelet MG, Dellis J, Content J (1990). Cloning and sequence analyses of cDNAs for interferon-beta and virus-induced human Mx proteins reveal that they contain putative guanine nucleotide-binding sites: functional study of the corresponding gene promoter. J. Virol. 64:1171-1181.

Kaufman RJ (1990). Vectors used for expression in mammalian cells. Meth. Enzymol. 185:487-511.

Nabel EG, Plautz G, Nabel GJ (1990). Site-specific gene expression in vivo by direct gene transfer into the arterial wall. Science 249:1285-1288.

Wolff JA, Malone RW, Williams P, Chong W, Acsadi G, Jani A, Felgner PL (1990). Direct gene transfer into mouse muscle in vivo. Science 247:1465-1468.

Brigham KL, Meyrick B, Christman B, Magnuson M, King G, Berry LC Jr (1989). In vivo transfection of murine lungs with a functioning prokaryotic gene using a liposome vehicle. Am. J. Med. Sci. 298:278-281.

Felgner PL, Holm M (1989). Cationic-liposome mediated transfection. Focus 11:21-25.

Felgner PL, Holm M, Chan H (1989). Cationic liposome mediated transfection. Proc. West. Pharmacol. Soc. 32: 115-121.

Berkner KL (1988). Development of adenovirus vectors for the expression of heterologous genes. BioTechniques 6:616-629.

DePamphilis ML, Herman SA, Martinez-Salas E, Chalifour LE, Wirak DO, Cupo DY, Miranda M (1988). Microinjecting DNA into mouse ova to study DNA replication and gene expression and to produce transgenic animals. BioTechniques 6:662-680.

Guild BC, Finer MH, Housman DE, Mulligan RC (1988). Development of retrovirus vectors useful for expressing genes in cultured murine embryonic cells and hematopoietic cells in vivo. J. Virol. 62:3795-3801.

McGrory WJ. Bautista DS, Graham FL (1988). A simple technique for the rescue of early region I mutations into infectious human adenovirus type 5. Virology 163(2):614-617.

Waxman, S., G. B. Rossi, and T. F., The Status of Differentiation Therapy of Cancer, in The Status of Differentiation Therapy of Cancer, S. Waxman, G.B. Rossi, and T. F., Editors. 1988, Raven Press: New York, NY. p. 1-422 (Table of Contents only).

Ghosh-Choudhury G, Graham FL (1987). Stable transfer of a mouse dihydrofolate reductase gene into a deficient cell line using human adenovirus vector. Biochem. Biophys. Res. Commun. 147(3):964-973.

Ghosh-Choudhury G, Haj-Ahmad Y, Brinkley P, Rudy J, Graham FL (1986). Human adenovirus cloning vectors based on infectious bacterial plasmids. Gene 50:161-171.

Haj-Ahmad Y, Graham FL (1986). Development of a helper-independent human adenovirus vector and its use in the transfer of the herpes simplex virus thymidine kinase gene. J. Virol. 57:257-274.

Hock RA, Miller AD, (1986). Retrovirus mediated transfer and expression of drug resistance genes in human hemopoietic progenitor cells. Nature 320:275-277.

Stavridis JC, Deliconstantinos G, Psallidopoulos MC, Armenakas NA, Hadjiminas DJ, Hadjiminas J (1986). Construction of trans ferrin-coated liposomes for in vivo transport of exogenous DNA to bone marrow erythroblasts in rabbits. Exp. Cell Res. 164:568-572.

Wigand R, Adrian T (1986). Classification and epidemiology of adenoviruses. In: Adenovirus DNA. Doerfler W, ed. Martinus Niijhoff Pub., Boston. pp. 408-441.

Fisher PB, Prignoli DR, Hermo H Jr, Weinstein IB, Pestka S (1985). Effects of combined treatment with interferon and mezerein on melanogenesis and growth in human melanoma cells. J. Interferon Res. 5:11-22.

Kaufman RJ (1985). Identification of the component necessary for adenovirus translational control and their utilization in cDNA expression vectors. Proc. Natl. Acad. Sci. USA 82:689-693.

Schmidt A, Setoyama C, de Crombrugghe B (1985). Regulation of a collagen gene promoter by the product of viral mos oncogene. Nature 314:286-289.

Wong GG, Witek JS, Temple PA, Wilkens KM, Leary AC, Luxenberg DP, Jones SS, Brown EL, Kay RM, Orr EC, Shoemaker C, Golde DW Kaufman RJ, Hewick RM, Wang EA, Clark SC (1985). Human GM-CSF: Molecular cloning of the complementary DNA and purification of the natural and recombinant proteins. Science 228:810-815.

Van Doren K, Gluzman Y (1984). Efficient transformation of human fibroblasts by adenovirus-simian virus 40 recombinants. Mol. Cell. Biol. 4(8):1653-1656.

Berkner KL, Sharp PA (1983). Generation of adenovirus by transfection of plasmids. Nucleic Acids Res. 11(17):6003-6020.

Capecchi MR, Luciw PA, Bishop JM, Varmus HE (1983). Location and function of retroviral and SV40 sequences that enhance biochemical transformation after microinjection of DNA. In: Enhancer and Eukaryotic Gene Expression. Gluzman Y, Shenk T, eds. Cold Spring Harbor Laboratories. pp. 101-102.

Jolly, DJ, Esty AC, Subramani S, Friedmann T, Verma IM (1983). Elements in the long terminal repeat of murine retroviruses enhance stable transformation by thymidine kinase gene. Nucleic Acids Res. 11:1855-1872.

Panicali D, Paoletti E (1983). Construction of poxvirus as cloning vectors: Insertion of the thymidine kinase gene from herpes simplex virus into the DNA of infectious vaccine virus. Proc. Natl. Acad. Sci. USA 79:4927-4931.

Smith GL, Mackett M, Moss B (1983). Infectious vaccinia virus recombinants that express hepatitis B virus surface antigens. Nature 302:490-495.

Gorman CM, Moffat LF, Howard BH (1982). Recombinant genomes which express chloramphenicol acetyltransferase in mammalian cells. Mol. Cell. Biol. 2(9):1044-1051.

Gluzman Y, Reichl H, Solnick D (1982). Helper-free adenovirus type-5 vectors. In: Eukaryotic Viral Vectors. Gluzman Y, ed. Cold Spring Harbor Laboratories. pp. 187-192.

Schaefer-Ridder M, Wang Y, Hofschneider PH (1982). Liposomes as gene carriers: Efficient transduction of mouse L cells by thymidine kinase gene. Science 215: 166-168.

Breathnach R, Chambon P (1981). Organization and expression of eucaryotic split genes coding for proteins. Ann. Rev. Biochem. 50:349-383.

Colbere-Garapin F, Horodniceanu F, Kourilsky P, Garapin AC (1981) A new dominant hybrid selective marker for higher eukaryotic cells. J. Mol. Biol. 150:1-14.

Mulligan RC, Berg P (1981). Selection for animal cells that express the *Escherichia coli* gene coding for xanthine-guanine phosphoribosyltransferase. Proc. Natl. Acad. Sci. USA 78:2072-2076.

Ringold G, Dieckmann B. Lee F (1981). Co-expression and amplification of dihydrofolate reductase cDNA and the *Escherichia coli* XGPRT gene in Chinese hamster ovary cells. J. Mol. Appl. Genet. 1:165-175.

Sarver N, Gruss P, Law MF, Khoury G, Howley PM (1981). Bovine papilloma virus DNA: a novel eukaryotic cloning vector. Mol. Cell Biol. 1:486-496.

Corden J, Wasylyk B, Buckwalder A, Sassone-Corsi P, Kedinger C, Chambon P (1980). Promoter sequences of eukaryotic protein-coding genes. Science 209:1406-1414.

Maxam AM, Gilbert W (1980). Sequencing end-labeled DNA with base-specific chemical cleavages. Methods Enzymol. 65:499-560.

Urlaub G, Chasin LA (1980). Isolation of Chinese hamster cell mutants deficient in dihydrofolate reductase activity. Proc. Natl. Acad. Sci. USA 77:4216-4220.

Bacchetti S, Graham FL (1977). Transfer of gene for thymidine kinase-deficient human cells by purified herpes simplex viral DNA. Proc. Natl. Acad. Sci. USA 74:1590-1594.

Fowler AV, Zabin I (1977). The amino acid sequence of beta-galactosidase of *Escherichia coli*. Proc. Natl. Acad. Sci. USA 74(4):1507-1510.

Tu SC, Waters CA, Hastings JW (1975). Photoexcited bacterial bioluminescence. Identity and properties of the photoexcitable luciferase. Biochemistry 14(9):1970-1974.

Armelin HA (1973). Pituitary extracts and steroid hormones in the control of 3T3 cell growth. Proc. Natl. Acad. Sci. USA 70:2702-2706.

Graham, FL, van der Eb AJ (1973). A new technique for the assay of infectivity of human adenovirus 5 DNA. Virology 5:456-467.

Freireich EJ, Gehan EA, Rall DP, Schmidt LH, Skipper HE (1966). Quantitative comparison of toxicity of anticancer agents in mouse, rat, hamster, dog, monkey, and man. Cancer Chemother. Rep. 50:219-244.

Waxman, S., ed. Differentiation Therapy (Ares Serono Symposia Publications, Rome). vol. 10. 1995. pp. 1-531 (Table of Contents only).

Lin JJ, Jiang H, Fisher PB (1998). Melanoma differentiation associated gene-9, mda-9, is a human gamma interferon responsive gene. Gene 207:105-110.

Jiang H, Lin JJ, Su ZZ, Goldstein NL, Fisher PB (1995). Subtraction hybridization identifies a novel melanoma differentiation associated gene, mda-7, modulated during human melanoma differentiation, growth, and progression. Oncogene 11: 2477-2486.

Jiang H, Lin J, Su ZZ, Herlin M, Kerbel RS, Weissman BE, Welch DR, Fisher PB (1995). The melanoma differentiation-associated gene mda-6, which encodes the cyclin-dependent kinase inhibitor p21, is differentially expressed during growth, differentiation, and progression in human melanoma cells. Oncogene 10:1855-1864.

* cited by examiner

FIGURE 1A-1

```
GCG CGG CCT GAG AGC CCT GTG GAC AAC CTC GTC ATT GTC AGG CAC AGA GCG GTA GAC
CCT GCT TCT CTA AGT GGG CAG CGG ACA GCG GCA CGC CTG TTT CAC CTG TCC CGC AGA CAA
CAG CAC CAT CTG GGG AGA ACC CTC TCC CTC TGA GAA AGA AAG ATG TCG AAT GGG
 Y   S   T   D   V   E   S   P   E   N   F   R   Y   L   I   S   M   S   N   G
TAT TCC ACA GAC GAG AAT TTC CGC TAT CTC ATC TCG TGC TTT CTC AGG CAC AGG GTG AAA ATG
 Y   I   Q   V   E   P   V   D   Y   L   T   F   L   P   A   E   R   V   K   M
TAC ATC CAG GTG GAG CCT GTG GAC TAC CTG ACC TTT CTG CCT GCA GAA AGA GTG AAG GAG
CAG ATT CAG AGG ACA GTC GCC TCC GGG AAC ATG CAG GCA GTT TTC GAA CTG CTG AGC
 Q   I   Q   R   T   V   A   S   G   N   M   Q   A   V   F   E   L   L   S
ACC TTG GAG AAG GGA GTC TGG CAC CTT GGT ACT CGG GAA GTG GAG GCC CTC CGG
 T   L   E   K   G   V   W   H   L   G   W   T   R   E   V   E   A   L   R
AGA ACC GGC AGC CCT CTG GCC CGC TAC ATG AAC CCT GAG CTC ACG GAC TTG CCC TCT
 R   T   G   S   P   L   A   R   Y   M   N   P   E   L   T   D   L   P   S
CCA TCG TTT GAG AAC GCT CAT GTT CTC TAT CTC CAA CTG CTG CTC AAC CTC CAG CCC ACT
 P   S   F   E   N   A   H   V   L   Y   L   Q   L   L   N   L   Q   P   T
CTG GTG GAC AAG AAG CTT CTA GTT AGA GAC GTC TTG AAG TGG ATG TCT GGA GAA CTG TTG
 L   V   D   K   K   L   L   V   R   D   V   L   K   W   M   S   G   E   L   L
ACA ATT GAA GAC CTA AAA AGG ATT GTG GCT GCT AAA GAA AAC TTC TCT GCA TTT CTG
 T   I   E   D   L   K   R   I   V   A   A   K   E   N   F   S   A   F   L
AGA GAG CTA CTA ACA AGG GAA AAC AAC GAG CAA CTT GTC TGT TCT GAT GTG TCA AAT GTT
 R   E   L   L   T   R   E   N   N   E   Q   L   V   C   S   D   V   S   N   V
CTT CGT CAA CTT ACA GGA ATT TTA TCA CAA GTT CCT CAA GAG GAA TCA GAA
 L   R   Q   L   T   G   I   L   S   Q   V   P   Q   E   E   S   E
AGC AAT GCA GAG ATT GAG AAT TTA TCA CAA GGT GAT GGT CCT CAA GTG GAA CAA CTT
 S   N   A   E   I   E   N   L   S   Q   V   D   G   P   Q   V   E   Q   L
```

```
CAC ATT TTA AAA CTA TGT GCC AAT CTT GAT GCA TTT ACT ATT AAA ACT GTT AAA GAA AAC
 H   I   L   K   L   C   A   N   L   D   A   F   T   I   K   T   V   K   E   N
CTT GAT CAA CTG AAA GAT CCA CAA ATA CAG GAG CCA CTA CTT ACT TGC AAG ATA ATG GAT GCA
 L   D   Q   L   K   D   P   Q   I   Q   E   P   L   L   T   C   K   I   A   D   A
ACC AGA GAA ATG AGT CCA AAA GAT CCA CTA AAA GAG AAA TTT GAA ATA ATG CAA ATT CAA ACT TAT
 T   R   E   M   S   P   K   D   P   L   K   E   K   F   E   I   M   Q   I   Q   T   Y
TGT CAA ATG AGT CCA ATG TCA GAT TTT GGA ACT TAT TTT CAA GAA ATA TGG CAA TGG GCC ATT CAA
 C   Q   M   S   P   M   S   D   F   G   T   Y   F   Q   E   I   W   Q   W   A   I   Q
ATG GAA AAA AAA GCT GCA AAA GGA AAT AAT CGC CAA AAA GAA CGT GTT GCA GAA GAA CAT TTG
 M   E   K   K   A   A   K   G   N   N   R   Q   K   E   R   V   A   E   E   H   L
AGG AAG TAC AAT GAG GCC CTA CAA ATT GAC ACA ATT CGA ATG GCA GAT GCG TAT GAT ACT
 R   K   Y   N   E   A   L   Q   I   D   T   I   R   M   A   D   A   Y   D   T
CAT CTT GAA ACT TTC TAT AAT GAG GAA AAG TTT GCA GAT GAG ATA GTC GAA GAT TTA GAT AAG
 H   L   E   T   F   Y   N   E   E   K   F   A   D   E   I   V   E   D   L   K
AGT GAT GAG GGT GAT GAT TAT GAT ACA ATG AAT GAT GAG ACT TTT TTT GAA AAC AAT
 S   D   E   G   D   D   Y   D   T   M   N   D   E   T   L   F   F   E   N   N
AAA CCT TTG AAA CTG CTG GAT AAC CCA GAA ACT AGG CTT ATT AAT TCA GCA CTG GGA ACC ATA TTA
 K   P   L   K   L   L   D   N   P   E   T   R   L   I   N   S   A   L   G   T   I   L
AAA ATG TTG AAA AGG ATG GAG TAT GCT CAA TAT ACT GCG GAG ACT TCC TGG ATT ACT GAA ATC ATC
 K   M   L   K   R   M   E   Y   A   Q   Y   T   A   E   T   S   W   I   T   E   I   I
AGA AAT ACC ATA ACG CAG ATG GAG TAT GCA TAT GCG CTT TCC CAG ATT ACT GAA AAT GAA ATA AAA TTT
 R   N   T   I   T   Q   M   E   Y   A   Y   A   L   S   Q   I   T   E   N   E   I   K   F
ACA AAA ACA CGA CAG GTC AAA GCC CAC CAC ATT GGA GCT CAC AGC AGT GAG TTC AAA
 T   K   T   R   Q   V   K   A   H   H   I   G   A   H   S   S   E   F   K
GCT GAA GTA GGA GTC AAA GCC CAT CAT ATT GGA GCT CAC AGC AGT GAG TTC AAA
 A   E   V   G   V   K   A   H   H   I   G   A   H   S   S   E   F   K
```

FIGURE 1A-4

```
CCC ATG ACA CAG AAT GAA CAA AAA GAA GTC ATT AGT AAA TTT CGC ACT GGA AAA ATC AAT
 P   M   T   Q   N   E   Q   K   E   V   I   S   K   F   R   T   G   K   I   N
CTG CTT ATC GCT ACA ACA GTG GCA GAA GAA ATA GGT GAT CTG GAT ATT AAA GAA ATT GTT
 L   L   I   A   T   T   V   A   E   E   I   G   D   L   D   I   K   E   I   V
ATC CGT TAT GGT CTC GTC ACC AAT GAA ATA GCC ATG GTC CAG ATG GCC CGT GGT GCC AGA
 I   R   Y   G   L   V   T   N   E   I   A   M   V   Q   M   A   R   G   A   R
GCT GAT GAG AGC TAC CTG GTT GCT CAC AGT GGT TCA ATC GTT GGA ATC GAA CAT GAG
 A   D   E   S   Y   L   V   A   H   S   G   S   I   V   G   I   E   H   E
ACA GTT AAT GAT TTC CGA GAG AAG ATG TAT AAA ATA CAG TGT GTT CAA AAT ATG
 T   V   N   D   F   R   E   K   M   Y   K   I   Q   C   V   Q   N   M
AAA CCA GAG TAT GCT CAT AAG ATT TTG GAA CAG ATG AGT ATA ATG GAA AAG
 K   P   E   Y   A   H   K   I   L   E   Q   M   S   I   M   E   K
AAA ATG AAA ACC AAG AGA AAT GCC CTA CAA AAC CCA ATC TCA CTA ATA ACT
 K   M   K   T   K   R   N   A   L   Q   N   P   I   S   L   I   T
TTC CTT TGC AAA AAC CAC AGT ATG GTG ACC GAA TTC CAA GCC TGT CAT ATT GAG
 F   L   C   K   N   H   S   M   V   T   E   F   Q   A   C   H   I   E
AAA ATG CAT GTC AAT GTC AAT ATG TGT TGT CAA TTC GAA CTT GTA AGA GAA AAC
 K   M   H   V   N   V   N   M   C   C   Q   F   E   L   V   R   E   N
AAA GCA CTG CAA AAG AAG ATG GTG CAC AAT CTT GAC AAA TAC AAA ATC TGC AAA TGT
 K   A   L   Q   K   K   M   V   H   N   L   D   K   Y   K   I   C   K   C
GGC CAG GCT TGG GGA ACA GTT TTC CCC TTA GAA AAG CAA TGC TTG CTC AAA AAG TGG GTA
 G   Q   A   W   G   T   V   F   P   L   E   K   Q   C   L   L   K   K   W   V
AGG AAT TTT GTA GTG ACA TTT CCC AAT CTT TTT TCA GAA TGC TGT AAA AAT TGG GAT GAG
 R   N   F   V   V   T   F   P   N   L   F   S   E   C   C   K   N   W   D   E
GAA TTA CAC TTG ATT GAA GAT TCT AAA ATA CTA ATA AGA ACT ATG ATT GTT TTA
 E   L   H   L   I   E   D   S   K   I   L   I   R   T   M   I   V   L
GAT TAG
 D   *
TGA TTA ATG TAT TCA TTA TGC TAC AGA ACT TGC
CTC TG
```

FIGURE 1B

```
CATTGAACTC TTTTTAAGAA CACAATATAT TANGCATTAT CCATCTTATT
GTTGGGCAGA GGTAAGGAAA ATNTACCAAT AATTTTCATT AGTGTGGAGC
ATTATANTCC TGTGGAAAGA ATGCTGAAGT ACAAATGAGA ATCCAAAGTA
CCAGTCTCAG TTCTGTCACT AATTTTCAGA ATAAAATTAG GCAAATCAGT
TC
```

FIGURE 1C

```
ICH-2     -MAEGNHRKKPLKVLESLGKDFLTGVLDNLVEQNVLNWKEEKKKYYD-AKTEDKVRVMA  58
ICE       -MADKVLKEKRKLFIRSMGEGTINGLLDELLQTRVLNKEEMEKVKREN-ATVMDKTRALI  58
IAP1-453  MASDDLSLIRKNRMALFQQLTCVLPILDNLLIKANVINKQEHDIIKQK--TQIPLQARELI  58
IAP2-439  -ESNDLLLIRKNRMALFQHLTCVIPILDSLLTAGIINRQEHDVIKQK--TQTSLQARELI  57
ICH-1     -MiPHHQETLKKNRVVLAKQLLLSELLEHLIEKDIITLEMRELIQAK--VGSFSQNVELL  57
mda5-125  ------------LVDKLLVRDVLDKCMEEELLTIEDRNRIAAAENNGNESGVRELL  44
RAIDD     MEARDKQVLRSLRLELGAEVLVEGLVLQLYQEGILTENHIQRINAQ--TTGLRKTMLLL  58
                                   :*:          :: .  :               :

ICH-2     DSMQEKQRMAGQMLLQTFFNIDQISP-------NKKAHPNMEAGPPESGESTDALKLCPHR  112
ICE       DSVIPKGAQACQICITYICEEDSYLAGTLGLSAAPQAVQDNPAMPTSSGSEGNVKLCSLR  118
IAP1-453  DTiLVKGNAAANIFKNCLKEIDSTLY------KNLFVDKNMKYIP----TEDVSGLSLRE  108
IAP2-439  DTILVKGNIAATVFRNSLQEAEAVLY------EHLFVQQDIKYIP----TEDVSDLPVER  107
ICH-1     NLLPKRGPQAFDAFCEALRETKQGHLED--MLLTTLSGLQHVLPPLSCDYDLSLPFPVCE  115
mda5-125  KRIVQK------------------------------------------------------  50
RAIDD     DILPSRGPKAFDTFLDSLQEFPPWVREK------LKKAREEAMTDLP-----AGDRLTGIPSH  109
                                                                   :
```

FIGURE 1D-1

```
eIF4A1         ------------------------------------------------------------   --
p68RNAhelicase ------------------------------MSASQDSRSRDNGP----------------   14
Mda-5          ------------------------------MSGYSSDRDRGRDRGFGAPRFGG---------   23
               LLLSTLEKGVWHLGWTREFVEALRRTGSPLAARYMNPELTDLPSPSFENAHDEYLQLINL  120
                                              . . .     .

eIF4A1         ----------------------------------DGME----------PEGVIESNWN--   28
p68RNAhelicase ----------------SRAGPLSGKKFGNP----------GEKLVKKKWNLD         49
Mda-5          LQPTLVDKLLVRDVLDKCMEEELLTIEDRNRIAAAENNGNESGVRELLKRIVQKENWFSA 180
                                              *                 . :.* eIF4A1         -----------PKFEKNFYQEHPDLARRTAQEVETYRRSKEITVRGH               87
p68RNAhelicase EL---------------------------------------------               --
Mda-5          FLNVLRQTGNNELVQELTGSDCSESNAEIENLSQVDGPQVEEQLLSTTVQPNLEKEVWGM 240
                                                                  .

eIF4A1         ---EIVDSFDDMNLS---------------------------------ESLLRGIYAYG   51
p68RNAhelicase NCPKPVLNFYEANFP---------------------------------ANVMDVIARQN  113
Mda-5          ENNSSESSFADSSVVSESDTSLAEGSVSCLDESLGHNSNMGSDSGTMGSDSDEENVAARA 300
                       *    .                                   :   .

eIF4A1         FEKP----SAIQQRAILPCIKGYDVIAQAQSGTGKTATFAISILQQIELD-----LKATQ  102
p68RNAhelicase FTEP----TAIQAQGWPVALSGLDMVGVAQTGSGKTLSYLLPAIVHINHQPFLERGDGPI  169
Mda-5          SPEPELQLRPYQMEVAQPALEGKNIIICLPTGSGKTRVAVYIAKDHLDKKK--KASEPGK  358
               :*            .     .:.*.    *   **:**  : .     :::

eIF4A1         ALVLAPTRELAQQIQ---------------------------------------------  117
p68RNAhelicase CLVLAPTRELAQQVQ---------------------------------------------  184
Mda-5          VIVLVNKVLLVEQLFRKEFQPFLKKWYRVIGLSGDTQLKISFPEVVKSCDIIISTAQILE  418
               :**. . *.:*:
```

FIGURE 1D-2

```
eIF4A1          ------------------------------------------------------------KVV  120
p68RNAhelicase  ------------------------------------------------------------QVA  187
Mda-5           NSLLNLENGEDAGVQLSDFSLIIIDECHHTNKEAVYNNIMRHYLMQKLNNRLKKENKPV       478 eIF4A1          MALGDYMGASCHACIGGTNVRAEVQKLQMEAPHIIVGTPGRVFDMLNRRYLSPKYIKMFV  180
p68RNAhelicase  AEYCRACRLKSTCIYGGAPKGPQIRDLERG--VEICIATPGRLIDFLECGKTNLRRTTYLV  246
Mda-5           IPLPQILGLTASPGVGGATKQAKAEEHILKLCANLDAFTIKTVKENLDQLKNQIQEPCKK   538 eIF4A1          LDEADEMLSRGFKDQIYDIFQKLNSNTQVVLLSATMPSDVLEVTKKFMRDPIRILVKKEE  240
p68RNAhelicase  LDEADRMLDMGFEPQIRKIVDQIRPDRQTLMWSATWPKEVRQLAEDFLKDYIHINIGALE  306
Mda-5           FAIADATREDPFKEKLLEIMTRIQTYCQMSPMSDFGTQPYEQWAIQMEKKAAKKGNRKER   598 eIF4A1          ------------------------------------------YINVEREEWKLDTLCD---  265
p68RNAhelicase  ------------------------------------------IVDVCHDVEKDEKLIR---  331
Mda-5           VCAEHLRKYNEALQINDTIRMIDAYTHLETFYNEEKDKKFAVIEDDSDEGGDDEYCDGDE  658 eIF4A1          ------------------------------------------LYETLTIT---  273
p68RNAhelicase  ------------------------------------------LMEEIMSEKE-  341
Mda-5           DEDDLKKPLKLDETDRFLMTLFFENNKMLKRLAENPEYENEKLTKLRNTIMEQYTRTEES  718 eIF4A1          -QAVIFINTRR----KVDWLTEKMHARDFTVSAMHGD--------MDQKERDVIMREF  318
p68RNAhelicase  NKTIVFVETKR----RCDELTRKMRRDGWPAMGIHGD--------KSQQERDWVLNEF  387
Mda-5           ARGIIFTKTRQSAYALSQWITENEKFAEVGVKAHHLIGAGHSSEFKPMTQNEQKEVISKF   778
```

FIGURE 1D-3

```
eIF4A1         RSGSSRVLITTDLLARGIDVQQVSLVINYDLPTNRENYIHRIGRG------GRFGRKGV 371
p68RNAhelicase KHGKAPILIATDVASRGLDVEDVKFVINYDYPNSSEDYIHRIGRT------ARSTKTGT 440
Mda-5          RTGKINLLIATTVAEEGLDIKECNIVIRYGLVTNEIAMVQARGRARADESTYVLVAHSGS 838
                  *.  :**:*  . :**.*.   .:**.*:  .       : * eIF4A1         AINMVTEEDKRTLRDIETFYNTSIEEMPLNVADLI-------------------------- 406
p68RNAhelicase AYTFFTPNNIKQVSDLISVLREANQAINPKLLQLVEDRGSGRSRGRGGMKDDRRDRYSAG 500
Mda-5          GVIEHETVNDFREKMMVKAIHCVQNMKPEEYAHKILELQMQSIMEKKMKTKRNIAKHYKN 898
                  :         :           ::    ::       .
```

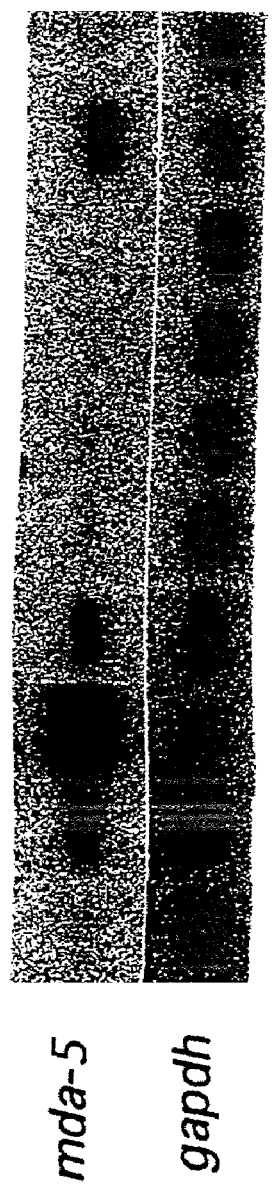
FIGURE 4A
FIGURE 4B

FIGURE 10

```
       GCACATTTTGGCCTACAAAGGACCTTATTGTTAAGGCAGAACCTGCTGGGAAAACAAAAT
   1   ---------+---------+---------+---------+---------+---------+   60

EcoRI
                                                      |
       ATCCGCCGGAGGAGCTTTGTAGAGCGTTGGTCTTGGTGTCAGAGAGAATTCGCTTTCCTT
  61   ---------+---------+---------+---------+---------+---------+  120

TTCTGTTTCCCGCGGTGTCCTTAACCAAAGGCCTCCTCTCTTCACCCGCCCCGACCAAAA
 121   ---------+---------+---------+---------+---------+---------+  180

GGTGGCGTCTCCCTGAGGAAACTCCCTCCCCGCCAGGCAGATTACGTTTACAAAGTCCTG
 181   ---------+---------+---------+---------+---------+---------+  240

AGAAGAGAATCGAAACAGAAACCAAAGTCAGGCAAACTCTGTAAGAACTGCCTGACAGAA
 241   ---------+---------+---------+---------+---------+---------+  300

AGCTGGACTCAAAGCTCCTACCCGAGTGTGCAGCAGGATCGCCCCGGTCCGGGACCCCAG
 301   ---------+---------+---------+---------+---------+---------+  360

GCGCACACCGCAGAGTCCAAAGTGCCGCGCCTGCCGGCCGCACCTGCCTGCCGCGGCCCC
 361   ---------+---------+---------+---------+---------+---------+  420

GCGCGCCGCCCCGCTGCCCACCTGCCCGCCTGCCCACCTGCCCAGGTGCGAGTGCAGCCC
 421   ---------+---------+---------+---------+---------+---------+  480

CGCGCGCCGGCCTGAGAGCCCTGTGGACAACCTCGTCATTGTCAGGCACAGAGCGGTAGA
 481   ---------+---------+---------+---------+---------+---------+  540

CCCTGCTTCTNTAAGTGGGCAGCGGACAGCGGCACGCACATTTCACCTGTCCCGCAGACA
 541   ---------+---------+---------+---------+---------+---------+  600

[BstXI]
            |
       ACAGCACCATCTGCTTGGGAGAACCCTCTCCCTTCTCTGAGAAAGAAAG ATG TCGAATGG
 601   ---------+---------+---------+---------+---------+---------+  660

GTATTCCACAGACGAGAATTTCCGCTATCTCATCTCGTGCTTCAGGGCCAGGGTGAAAAT
 661   ---------+---------+---------+---------+---------+---------+  720

GTACATCCAGGTGGAGCCTGTGCTGGACTACCTGACCTTTCTGCCTGCAGAGGTGAAGGA
 721   ---------+---------+---------+---------+---------+---------+  780

GCAGATTCAGAGGACAGTCGCCACCTCCGGGAACATGCAGGCAGTTGAACTGCTGCTGAG
 781   ---------+---------+---------+---------+---------+---------+  840

EcoRI
                                          |
       CACCTTGGAGAAGGGAGTCTGGCACCTTGGTTGGACTCGGGAATTCGTGGAGGCCCTCCG
 841   ---------+---------+---------+---------+---------+---------+  900

SacI
                                          |
       GAGAACCGGCAGCCCTCTGGCCGCCCGCTACATGAACCCTGAGCTCACGGACTTGCCCTC
 901   ---------+---------+---------+---------+---------+---------+  960

TCCATCGTTTGAGAACGCTCATGATGAATATCTCCAACTGCTGAACCTCCTTCAGCCCAC
 961   ---------+---------+---------+---------+---------+---------+ 1020

HindIII
       [BstXI]   |
       TCTGGTGGACAAGCTT
1021   ---------+------  1036
```

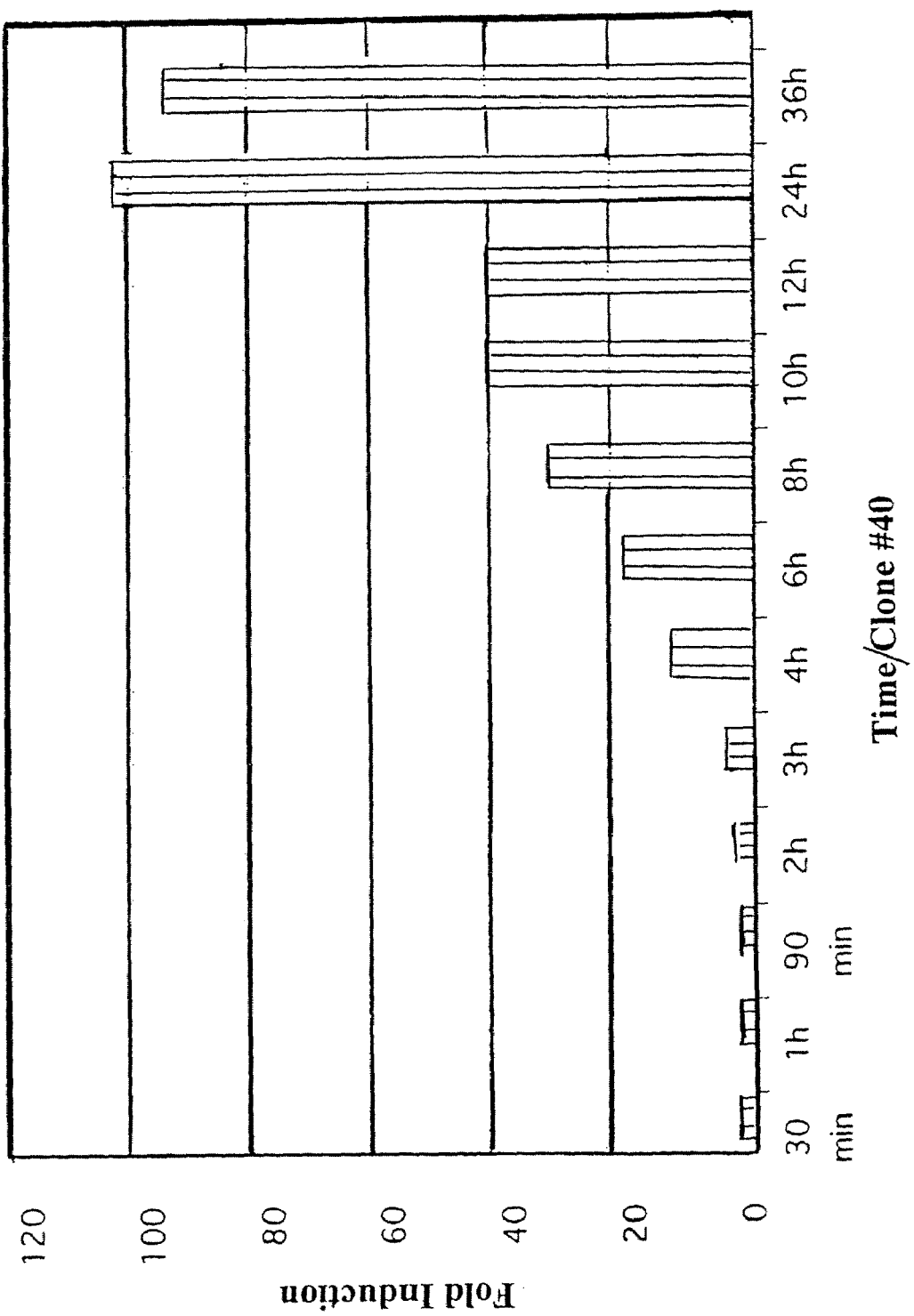

US 7,229,822 B1

MELANOMA DIFFERENTIATION ASSOCIATED GENE-5 AND VECTORS AND CELLS CONTAINING SAME

The invention disclosed herein was made with Government support under National Institutes of Health Chernow Endowment No. CA 74468-01 from the U.S. Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately preceding the claims. All patents, patent applications and publications cited herein, whether supra or infra, are hereby incorporated by reference in their entirety. The disclosures of these publications in their entireties are hereby incorporated by reference into this application in order to more fully describe the state of the art as known to those skilled therein as of the date of the invention described and claimed herein.

Abnormalities in differentiation are common occurrences in human cancers ((1) Fisher and Grant, 1985; (2) Waxman, 1995). Moreover, as cancer cells evolve, ultimately developing new phenotypes or acquiring a further elaboration of preexisting transformation-related properties, the degree of expression of differentiation-associated traits often undergo a further decline. These observations have been exploited as a novel means of cancer therapy in which tumor cells are treated with agents that induce differentiation and a loss of cancerous properties, a strategy called 'differentiation therapy' ((2–4) Waxman et al., 1988, 1991; Jiang et al., 1994; Waxman, 1995). In principle, differentiation therapy may prove less toxic than currently employed chemotherapeutic approaches, including radiation and treatment with toxic chemicals. The ability to develop rational schemes for applying differentiation therapy clinically require appropriate in vitro and in vivo model systems for identifying and characterizing the appropriate agent or agents that can modulate differentiation in cancer cells without causing undue toxicity to normal cells.

SUMMARY OF THE INVENTION

The invention provides for an isolated nucleic acid encoding Mda-5 polypeptide as shown in SEQ ID NO:1. A polypeptide having the sequence shown in SEQ ID NO:2.

The present invention provides for an isolated Mda-5 promoter capable of directing transcription of a heterologous coding sequence positioned downstream therefrom, wherein the promoter is selected from the group consisting of: (a) a promoter comprising the nucleotide sequence shown in SEQ ID NO:3; (b) a promoter comprising a nucleotide sequence functionally equivalent to the nucleotide sequence shown in SEQ ID NO: 3; and (c) a promoter comprising a nucleotide sequence that hybridizes to a sequence complementary to the promoter of (a) or (b) in a Southern hybridization reaction performed under stringent conditions. The invention provides for a host cell comprising the recombinant expression construct as described herein. The invention provides for a method for expressing foreign DNA in a host cell comprising: introducing into the host cell a gene transfer vector comprising an Mda-5 promoter nucleotide sequence operably linked to a foreign DNA encoding a desired polypeptide or RNA, wherein said foreign DNA is expressed. The invention further provides for a method for treating cancer in a subject suffering therefrom which comprises administering to the subject an effective amount of a pharmaceutical composition which comprises a recombinant expression construct comprising: (a) a nucleic acid molecule that encodes a selected polypeptide; and (b) an Mda-5 promoter nucleotide sequence operably linked to the nucleic acid molecule of element (a), wherein the coding sequence will be transcribed and translated when in a host cell to produce the selected polypeptide, and the Mda-5 promoter is heterologous to the coding sequence and a pharmaceutically acceptable carrier.

BRIEF DESCRIPTION OF THE FIGURES

FIGS. 1A–1D. Sequence of mda-5 and alignment with CARD and RNA helicases. FIG. 1A. Nucleotide sequence (SEQ ID NO:1) and corresponding amino acid sequence (SEQ ID NO:2) of mda-5. Underlined sequences are AUUUA sequences. Bold face sequence is the poly A signal. FIG. 1B. Additional nucleotide sequence of mda-5p (SEQ ID NO:4). Poly A signal is bold faced. FIG. 1C. Alignment of CARD proteins with 50 amino acids near the N-terminal region of MDA-5 (a.a. 125–174 correspond to 1–50). (SEQ ID NOS:5–11) FIG. 1D. Alignment of the RNA helicase conserved motif of mda-5 with eIF-4A (SEQ ID NO:12) and p68 RNA helicases-2E (SEQ ID NO:13).

FIG. 2A. HO-1 human melanoma cells. FIG. 2B. Early passage human skin fibroblast cells. Northern hybridization was performed as in Materials and Methods. Abbreviations and concentration of the indicated reagents are as follows: ctl, control; DMSO, 0.1% dimethyl sulfoxide; EtOH, 0.25% final concentration of ethanol; Mez, mezerein 10 ng/ml; IFN-β, 2,000 U/ml interferon-β; IFN-β+Mez, 2,000 U/ml interferon-β plus mezerein 10 ng/ml; IFN-γ, interferon-γ 100 U/ml; IFN-γ+Mez, interferon-γ 100 U/ml plus mezerein 10 ng/ml; RA, all-trans-retinoic acid 2.5 B5M (dissolved in EtOH): MPA, mycophenolic acid 3 B5M; TPA, 12-O-tetradecanoylphorbol-13-acetate 16 nM; cAMP, 3'-5' cyclic adenosine monophosphate 1 mM; 8-Br-cAMP, 8-bromo-3'-5' cyclic adenosine monophosphate 1 mM; MMS, methylmethane sulfonate 10 ng/ml; poly IC 10 µg/ml.

FIGS. 4A–4B. Northern blot analysis of mda-5 expression by ligands for various membrane receptors. RNA samples were extracted from cells treated as indicated for 24 hr. FIG. 4A. HO-1 human melanoma cells. FIG. 4B. Early passage human skin fibroblast cells. Northern hybridization was performed as in Materials and Methods. Abbreviations and concentrations of indicated reagents are as follows: ctl, control; IFN-α, 1,000 U/ml interferon-α IFN-β, 1,000 U/ml interferon-β IFN-γ, 1,000 U/ml interferon-γ, IL-6, interleukin-6, 1 ng/ml; EGF, epidermal growth factor, 10 ng/ml; TGF-α, transforming growth factor α, 10 ng/ml; TGF-β transforming growth factor β, 2.5 ng/ml; TNF-α, tumor necrosis factor α, 10 ng/ml; PDGF, platelet-derived growth factor, 10 ng/ml.

FIG. 7B. Nuclear run-on assays for determining mda-5 transcription rates. Nuclei were prepared from HO-1 melanoma cells treated with the indicated reagent(s) for 4 hr. Blots were prepared and hybridized as described in Materials and Methods. Abbreviations and concentrations of the indicated reagents are as follows: mda-5 5' and 3' fragment of mda-5 cDNA, respectively; ctl, control; Mez, mezerein 10 ng/ml; IFN-β, 2,000 U/ml interferon-β; IFN-β+Mez, 2,000 U/ml interferon-β plus mezerein 10 ng/ml. FIG. 7C. Northern blot analysis of mda-5 expression after blocking protein synthesis by cycloheximide (CHX). RNA samples were extracted from HO-1 melanoma cells pretreated with 50 µg/ml cycloheximide for 30 min and treated with the indicated reagents for 8 hr. Abbreviations and concentrations of indicated reagents are as in FIG. 4.

FIG. 8A. Autoradiogram of 9% SDS-PAGE of in vitro translated mda-5 cDNA. β-galactosidase was used as a positive control. FIG. 8B. Western blot analysis of mda-5 fusion protein resolved in 9% SDS-PAGE. Protein extracts were prepared from 293T cells transiently transfected with the indicated expression vector. Details of transfection and immunoblot can be found in Materials and Methods. FIG. 8C. Intracellular localization of mda-5 protein. Transiently transfected 293T cells with the indicated fusion protein constructs were mounted and observed by fluorescent confocal microscopy (400×).

FIG. 10. The sequence of the proximal promoter region of the mda-5 (SEQ ID NO:3) gene showing landmark restriction sites. The initiator Methionine codon is highlighted by an open box as are the BstXI sites used to perform an internal deletion that removed the ATG as described in the text.

FIG. 14A. HO-1 cells transiently transfected with the mda-5 reporter and treated for 48 h with equivalent units of IFNs α, β and γ and TNF-α and poly IC:IC. The luciferase activity was expressed as fold increase over untreated control cells. FIG. 14B. Clone #40 was treated with equivalent units of the indicated IFNs for 48 h and luciferase activity expressed as fold activation over untreated cells determined.

DETAILED DESCRIPTION OF THE INVENTION

Figure 2A:
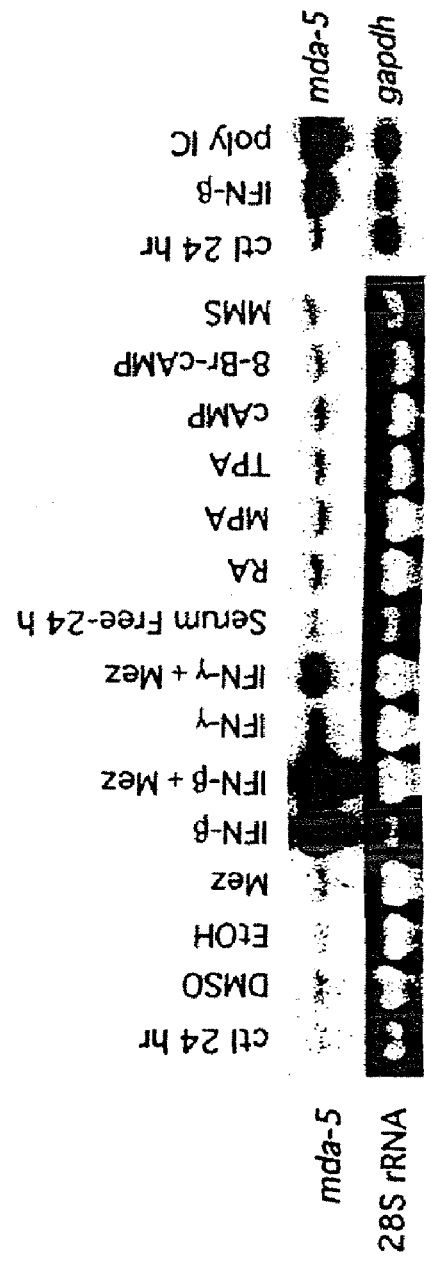
FIGS. 2A–2B. Northern blot analysis of mda-5 expression by various compounds inducing differentiation in HO-1 human melanoma cells. RNA samples were extracted from cells treated as indicated for 24 hr.

The following abbreviations are used herein: Mda-5—Melanoma differentiation associated gene-5, CMV—cytomegalovirus, The invention provides for an isolated nucleic acid comprising the sequence shown in SEQ ID NO: 1 encoding a Melanoma Differentiation Associated Gene-5 (Mda-5) polypeptide.

In one embodiment, the invention provides for an isolated nucleic acid comprising a derivative of the sequence of SEQ ID NO:1 encoding a polypeptide which is functionally equivalent to Mda-5.

The present invention also provides for a fragment of the isolated nucleic acid aforementioned, wherein the fragment encodes a polypeptide having Mda-5 biological activity.

The invention provides for a nucleic acid which hybridizes to the DNA shown in SEQ ID NO:1 or the complementary strand thereof, wherein the nucleic acid or the complementary strand thereof, encodes a polypeptide having Mda-5 activity.

The invention further provides for a vector comprising any of the nucleic acids described herein. In one embodiment, the vector is a replicable vector, a gene transfer vector, an expression vector, or a vector capable of driving expression of a gene of interest in a host cell.

The invention provides for a host cell comprising the aforementioned vector.

The invention provides a method for identifying a compound as an agonist or antagonist of interferon-β, interferon-α or interferon γ which comprises: (a) contacting a cell with the compound, wherein the cell comprises a nucleic acid having the sequence shown in SEQ ID NO:2, or a functional equivalent thereof, operably linked to a reporter gene; (b) measuring the level of reporter gene expressed by the cell in the presence of the compound; (c) comparing the expression level of the reporter gene measured in step (b) with the expression level of reporter gene measured in the absence of the compound, so as to identify whether the compound is an interferon agonist or antagonist; wherein a higher level of reporter gene expression measured in step (b) is indicative of the compound being an interferon agonist, and wherein a lower level of reporter gene expression measured in step (b) is indicative of the compound being an interferon antagonist.

In one embodiment, the compound is a small organic molecule having a weight of about 5 kilodaltons or less.

In another embodiment, the cell is a HO-1 human melanoma cell. In another embodiment of the invention, the level of reporter gene expression measured which is indicative of an agonist is from 10 to 1000 fold higher than the level of reporter gene expression measured in the absence of the compound.

In another embodiment of the invention, the reporter gene is luciferase.

The invention provides for an isolated polypeptide having the amino acid sequence shown in SEQ ID NO:2 encoding Mda-5.

The invention also provides for an isolated antibody which specifically binds to the polypeptide having the sequence shown in SEQ ID NO:2.

In one embodiment, the antibody is a monoclonal antibody.

The invention provides for an isolated Mda-5 promoter capable of directing transcription of a heterologous coding sequence positioned downstream therefrom, wherein the promoter is selected from the group consisting of: (a) a promoter comprising the nucleotide sequence shown in SEQ ID NO:3; (b) a promoter comprising a nucleotide sequence functionally equivalent to the nucleotide sequence shown in SEQ ID NO: 3; and (c) a promoter comprising a nucleotide sequence that hybridizes to a sequence complementary to the promoter of (a) or (b) in a Southern hybridization reaction performed under stringent conditions.

In one embodiment, the promoter comprises the nucleotide sequence shown in SEQ ID NO:3.

The invention provides for a recombinant expression construct effective in directing the transcription of a selected coding sequence which comprises: (a) an Mda-5 promoter nucleotide sequence according to claim 15; and (b) a coding sequence operably linked to the promoter, whereby the coding sequence can be transcribed and translated in a host cell, and the promoter is heterologous to the coding sequence.

In one embodiment, the Mda-5 promoter comprises a human Mda-5 promoter.

In another embodiment, the human Mda-5 promoter comprises the nucleotide sequence shown in SEQ ID NO:3.

In another embodiment, the coding sequence encodes a tumor suppressor polypeptide.

In another embodiment, the tumor suppressor polypeptide is p21, retinoblastoma protein or p53.

The invention provides for a host cell comprising the recombinant expression construct described herein. In one embodiment the host cell is stably transformed with the recombinant expression construct.

In another embodiment, the host cell is a tumor cell.
In another embodiment, the host cell is a melanocyte.
In another embodiment, the cell is an immortalized cell.
In another embodiment, the tumor cell is a melanoma cell, a neuroblastoma cell, an astrocytoma cell, a glioblastomoa multifore cell, a cerival cancer cell, a breast cancer cell, a lung cancer cell or a prostate cancer cell.

The invention provides for an isolated Mda-5 promoter capable of directing the transcription of a heterologous coding sequence positioned downstream therefrom, wherein the promoter is selected from the group consisting of (a) a promoter comprising the nucleotide sequence shown in SEQ ID NO:3; (b) a promoter comprising a nucleotide sequence functionally equivalent to the promoter in element (a); and (c) a promoter comprising a nucleotide sequence that hybridizes to a sequence complementary to the promoter of element (a) or element (b) in a Southern hybridization reaction performed under stringent conditions.

The invention also provides for a method for treating cancer in a subject suffering therefrom which comprises administering to the subject an effective amount of a pharmaceutical composition which comprises a recombinant expression construct comprising:
(a) a nucleic acid molecule that encodes a polypeptide of interest; and
(b) an Mda-5 promoter nucleotide sequence operably linked to the nucleic acid molecule of element (a), and wherein the Mda-5 promoter is heterologous to the nucleic acid molecule,
and a pharmaceutically acceptable carrier.

In one embodiment, the cancer is melanoma, neuroblastoma, astrocytoma, glioblastoma multiforme, cervical cancer, breast cancer, colon cancer, prostate cancer, osteoscarcoma, or chrondosarcoma.

In one embodiment, the cancer is a cancer of the central nervous system of the subject.

In one embodiment, the administering is carried out via injection, oral administration, topical administration, adenovirus infection, liposome-mediated transfer, topical application to the cells of the subject, or microinjection.

In one embodiment, the carrier is an aqueous carrier, a liposome, or a lipid carrier.

```
mda-5 cDNA (SEQ ID NO:1)
GCGCGCCGGC CTGAGAGCCC TGTGGACAAC CTCGTCATTG

TCAGGCACAG AGCGGTAGAC CCTGCTTCTC TAAGTGGGCA

GCGGACAGCG GCACGCACAT TTCACCTGTC CCGCAGACAA

CAGCACCATC TGCTTGGGAG AACCCTCTCC CTTCTCTGAG

AAAGAAAGAT GTCGAATGGG TATTCCACAG ACGAGAATTT

CCGCTATCTC ATCTCGTGCT TCAGGGCCAG GGTGAAAATG

TACATCCAGG TGGAGCCTGT GCTGGACTAC CTGACCTTTC

TGCCTGCAGA GGTGAAGGAG CAGATTCAGA GGACAGTCGC

CACCTCCGGG AACATGCAGG CAGTTGAACT GCTGCTGAGC

ACCTTGGAGA AGGGAGTCTG GCACCTTGGT TGGACTCGGG

AATTCGTGGA GGCCCTCCGG AGAACCGGCA GCCCTCTGGC

CGCCCGCTAC ATGAACCCTG AGCTCACGGA CTTGCCCTCT

CCATCGTTTG AGAACGCTCA TGATGAATAT CTCCAACTGC

TGAACCTCCT TCAGCCCACT CTGGTGGACA AGCTTCTAGT

TAGAGACGTC TTGGATAAGT GCATGGAGGA GGAACTGTTG

ACAATTGAAG ACAGAAACCG GATTGCTGCT GCAGAAAACA

ATGGAAATGA ATCAGGTGTA AGAGAGCTAC TAAAAAGGAT

TGTGCAGAAA GAAAACTGGT TCTCTGCATT TCTGAATGTT

CTTCGTCAAA CAGGAAACAA TGAACTTGTC CAAGAGTTAA

CAGGCTCTGA TTGCTCAGAA AGCAATGCAG AGATTGAGAA

TTTATCACAA GTTGATGGTC CTCAAGTGGA AGAGCAACTT
```

-continued

```
CTTTCAACCA CAGTTCAGCC AAATCTGGAG AAGGAGGTCT
GGGGCATGGA GAATAACTCA TCAGAATCAT CTTTTGCAGA
TTCTTCTGTA GTTTCAGAAT CAGACACAAG TTTGGCAGAA
GGAAGTGTCA GCTCCTTAGA TGAAAGTCTT GGACATAACA
GCAACATGGG CAGTGATTCA GGCACCATGG GAAGTGATTC
AGATGAAGAG AATGTGGCAG CAAGAGCATC CCCGGAGCCA
GAACTCCAGC TCAGGCCTTA CCAAATGGAA GTTGCCCAGC
CAGCCTTGGA AGGGAAGAAT ATCATCATCT GCCTCCCTAC
AGGGAGTGGA AAAACCAGAG TGGCTGTTTA CATTGCCAAG
GATCACTTAG ACAAGAAGAA AAAAGCATCT GAGCCTGGAA
AAGTTATAGT TCTTGTCAAT AAGGTACTGC TAGTTGAACA
GCTCTTCCGC AAGGAGTTCC AACCATTTTT GAAGAAATGG
TATCGTGTTA TTGGATTAAG TGGTGATACC CAACTGAAAA
TATCATTTCC AGAAGTTGTC AAGTCCTGTG ATATTATTAT
CAGTACAGCT CAAATCCTTG AAAACTCCCT CTTAAACTTG
GAAAATGGAG AAGATGCTGG TGTTCAATTG TCAGACTTTT
CCCTCATTAT CATTGATGAA TGTCATCACA CCAACAAAGA
AGCAGTGTAT AATAACATCA TGAGGCATTA TTTGATGCAG
AAGTTGAAAA ACAATAGACT CAAGAAAGAA AACAAACCAG
TGATTCCCCT TCCTCAGATA CTGGGACTAA CAGCTTCACC
TGGTGTTGGA GGGGCCACGA AGCAAGCCAA AGCTGAAGAA
CACATTTTAA AACTATGTGC CAATCTTGAT GCATTTACTA
TTAAAACTGT TAAAGAAAAC CTTGATCAAC TGAAAAACCA
AATACAGGAG CCATGCAAGA AGTTTGCCAT TGCAGATGCA
ACCAGAGAAG ATCCATTTAA AGAGAAACTT CTAGAAATAA
TGACAAGGAT TCAAACTTAT TGTCAAATGA GTCCAATGTC
AGATTTTGGA ACTCAACCCT ATGAACAATG GGCCATTCAA
ATGGAAAAAA AAGCTGCAAA AAAAGGAAAT CGCAAAGAAC
GTGTTTGTGC AGAACATTTG AGGAAGTACA ATGAGGCCCT
ACAAATTAAT GACACAATTC GAATGATAGA TGCGTATACT
CATCTTGAAA CTTTCTATAA TGAAGAGAAA GATAAGAAGT
TTGCAGTCAT AGAAGATGAT AGTGATGAGG GTGGTGATGA
TGAGTATTGT GATGGTGATG AAGATGAGGA TGATTTAAAG
AAACCTTTGA AACTGGATGA AACAGATAGA TTTCTCATGA
CTTTATTTTT TGAAACAATA AAATGTTGA AAAGGCTGGC
TGAAAACCCA GAATATGAAA ATGAAAAGCT GACCAAATTA
AGAAATACCA TAATGGACCA ATATACTAGG ACTGAGGAAT
CAGCACGAGG AATAATCTTT ACAAAAACAC GACAGAGTGC
ATATGCGCTT TCCCAGTGGA TTACTGAAAA TGAAAAATTT
GCTGAAGTAG GAGTCAAAGC CCACCATCTG ATTGGAGCTG
```

-continued

```
GACACAGCAG TGAGTTCAAA CCCATGACAC AGAATGAACA
AAAAGAAGTC ATTAGTAAAT TTCGCACTGG AAAAATCAAT
CTGCTTATCG CTACCACAGT GGCAGAAGAA GGTCTGGATA
TTAAAGAATG TAACATTGTT ATCCGTTATG GTCTCGTCAC
CAATGAAATA GCCATGGTCC AGGCCCGTGG TCGAGCCAGA
GCTGATGAGA GCACCTACGT CCTGGTTGCT CACAGTGGTT
CAGGAGTTAT CGAACATGAG ACAGTTAATG ATTTCCGAGA
GAAGATGATG TATAAAGCTA ACATTGTGT TCAAAATATG
AAACCAGAGG AGTATGCTCA TAAGATTTTG GAATTACAGA
TGCAAAGTAT AATGGAAAAG AAAATGAAAA CCAAGAGAAA
TATTGCCAAG CATTACAAGA ATAACCCATC ACTAATAACT
TTCCTTTGCA AAAACTGCAG TGTGCTAGCC TGTTCTGGGG
AAGATATCCA TGTAATTGAG AAAATGCATC ACGTCAATAT
GACCCCAGAA TTCAAGGAAC TTTACATTGT AAGAGAAAAC
AAAGCACTGC AAAAGAAGTG TGCCGACTAT CAAATAAATG
GTGAAATCAT CTGCAAATGT GGCCAGGCTT GGGGAACAAT
GATGGTGCAC AAAGGCTTAG ATTTGCCTTG TCTCAAAATA
AGGAATTTTG TAGTGGTTTT CAAAAATAAT TCAACAAAGA
AACAATACAA AAAGTGGGTA GAATTACCTA TCACATTTCC
CAATCTTGAC TATTCAGAAT GCTGTTTATT TAGTGATGAG
GATTAGCACT TGATTGAAGA TTCTTTTAAA ATACTATCAG
TTAAACATTT AATATGATTA TGATTAATGT ATTCATTATG
CTACAGAACT GACATAAGAA TCAATAAAAT GATTGTTTTA
CTCTG
```

Mda-5 potein sequence (SEQ ID NO:2)
```
MSNGYSTDEN FRYLISCFRA RVKMYIQVEP VLDYLTFLPA
EVKEQIQRTV ATSGNMQAVE LLLSTLEKGV WHLGWTREFV
EALRRTGSPL AARYMNPELT DLPSPSFENA HDEYLQLLNL
LQPTLVDKLL VRDVLDKCME EELLTIEDRN RIAAAENNGN
ESGVRELLKR IVQKENWFSA FLNVLRQTGN NELVQELTGS
DCSESNAEIE NLSQVDGPQV EEQLLSTTVQ PNLEKEVWGM
ENNSSESSFA DSSVVSESDT SLAEGSVSCL DESLGHNSNM
GSDSGTMGSD SDEENVAARA SPEPELQLRP YQMEVAQPAL
EGKNIIICLP TGSGKTRVAV YIAKDHLDKK KKASEPGKVI
VLVNKVLLVE QLFRKEFQPF LKKWYRVIGL SGDTQLKISF
PEVVKSCDTT ISTAQILENS LLNLENGEDA GVQLSDFSLI
IIDECHHTNK EAVYNNIMRH YLMQKLKNNR LKKENKPVIP
LPQILGLTAS PGVGGATKQA KAEEHILKLC ANLDAFTIKT
VKENLDQLKN QIQEPCKKFA IADATREDPF KEKLLEIMTR
```

```
                    -continued
IQTYCQMSPM SDFGTQPYEQ WAIQMEKKAA KKGNRKERVC

AEHLRKYNEA LQINDTIRMI DAYTHLETFY NEEKDKKFAV

IEDDSDEGGD DEYCDCDEDE DDLKKPLKLD ETDRFLMTLF

FENNKMLKRL AENPEYENEK LTKLRNTIME QYTRTEESAR

GIIFTKTRQS AYALSQWITE NEKFAEVGVK AHHLIGAGHS

SEFKPMTQNE QKEVTSKFRT GKINLLIATT VAEEGLDIKE

CNIVIRYGLV TNEIANVQAR GRARADESTY VLVAHSGSGV

IEHETVNDFR EKMMYKAIHC VQNMKPEEYA HKILELQMQS

IMEKKMKTKR NIAKHYKNNP SLITFLCKNC SVLACSGEDI

HVIEKMHHVN MTPEFKELYI VRENKALQKK CADYQINGEI

ICKCGQAWGT MMVHKGLDLP CLKIRNFVVV FKNNSTKKQY

KKWVELPITF PNLDYSECCL FSDED*
```

The practice of the present invention will employ, unless otherwise indicated, conventional techniques of molecular biology, microbiology, virology, recombinant DNA technology, and immunology, which are within the skill of the art. Such techniques are explained fully in the literature. See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I–IV (D. M. Weir and C. C. Blackwell eds., 1986, Blackwell Scientific Publications).

As used in this specification and the appended claims, the singular forms "a," "an" and "the" include plural references unless the content clearly dictates otherwise.

The present invention provides for an isolated Mda-5 promoter capable of directing transcription of a heterologous coding sequence positioned downstream therefrom, wherein the promoter is selected from the group consisting of: (a) a promoter comprising the nucleotide sequence shown in SEQ ID NO: 3; (b) a promoter comprising a nucleotide sequence functionally equivalent to the nucleotide sequence shown in SEQ ID NO: 3; and (c) a promoter comprising a nucleotide sequence that hybridizes to a sequence complementary to the promoter of (a) or (b) in a Southern hybridization reaction performed under stringent conditions.

In one embodiment of the invention, the promoter comprises the nucleotide sequence shown in SEQ ID NO:3.

The present invention also provides for a recombinant expression construct effective in directing the transcription of a selected coding sequence which comprises:

(a) an Mda-5 promoter nucleotide sequence as described herein; and (b) a coding sequence operably linked to the promoter, whereby the coding sequence can be transcribed and translated in a host cell, and the promoter is heterologous to the coding sequence. In another embodiment of the invention, the Mda-5 promoter comprises a human Mda-5 promoter.

In another embodiment of the invention, the human Mda-5 promoter comprises the nucleotide sequence shown in SEQ ID NO:3.

In another embodiment of the invention, the coding sequence encodes a tumor suppressor polypeptide.

In another embodiment of the invention, the tumor suppressor polypeptide is p21, retinoblastoma protein or p53.

The invention provides for a host cell comprising the recombinant expression construct as described herein.

In another embodiment of the invention, the host cell is stably transformed with the recombinant expression construct described herein.

In another embodiment of the invention, the host cell is a tumor cell.

In another embodiment of the invention, the host cell is a melanocyte.

In another embodiment of the invention, the cell is an immortalized cell.

In another embodiment of the invention, the tumor cell is a melanoma cell, a neuroblastoma cell, an astrocytoma cell, a glioblastomoa multifore cell, a cerival cancer cell, a breast cancer cell, a lung cancer cell or a prostate cancer cell.

The invention provides for a method for expressing foreign DNA in a host cell comprising: introducing into the host cell a gene transfer vector comprising an Mda-5 promoter nucleotide sequence operably linked to a foreign DNA encoding a desired polypeptide or RNA, wherein said foreign DNA is expressed.

In another embodiment of the invention, the gene transfer vector encodes and expresses a reporter molecule.

In another embodiment of the invention, the reporter molecule is selected from the group consisting of beta-galactosidase, luciferase and chloramphenicol acetyltransferase.

In another embodiment of the invention, the "introducing" is carried out by a means selected from the group consisting of adenovirus infection, liposome-mediated transfer, topical application to the cell, and microinjection.

The invention provides for an isolated Mda-5 promoter capable of directing the transcription of a heterologous coding sequence positioned downstream therefrom, wherein the promoter is selected from the group consisting of (a) a promoter comprising the nucleotide sequence shown in SEQ ID NO:3; (b) a promoter comprising a nucleotide sequence functionally equivalent to the promoter in element (a); and (c) a promoter comprising a nucleotide sequence that hybridizes to a sequence complementary to the promoter of element (a) or element (b) in a Southern hybridization reaction performed under stringent conditions.

The invention further provides for a method for treating cancer in a subject suffering therefrom which comprises administering to the subject an effective amount of a pharmaceutical composition which comprises a recombinant expression construct comprising: (a) a nucleic acid molecule that encodes a selected polypeptide; and (b) an Mda-5 promoter nucleotide sequence operably linked to the nucleic acid molecule of element (a), wherein the coding sequence will be transcribed and translated when in a host cell to produce the selected polypeptide, and the Mda-5 promoter is heterologous to the coding sequence and a pharmaceutically acceptable carrier.

In another embodiment of the invention, the cancer is melanoma, neuroblastoma, astrocytoma, glioblastoma multiforme, cervical cancer, breast cancer, colon cancer, prostate cancer, osteoscarcoma, or chrondosarcoma.

In another embodiment of the invention, the cancer is a cancer of the central nervous system of the subject.

In another embodiment of the invention, the administering is carried out via injection, oral administration, or topical administration.

In another embodiment of the invention, the carrier is an aqueous carrier, a liposome, or a lipid carrier.

A method for determining whether a compound is an inducer of Mda-5 gene expression in a cell and an inducer of terminal differentiation of such cell which comprises: (a) contacting a cell with the compound, wherein the cell comprises a nucleic acid encoding Mda-5 having the sequence shown in SEQ ID NO:1, or a functional equivalent thereof, operably linked to an Mda-5 promoter; (b) measuring the level of either (i) Mda-5 mRNA produced or (ii) Mda-5 polypeptide expressed by the cell in the presence of the compound; (c) comparing the expression level of Mda-5 mRNA or polypeptide measured in step (b) with the level measured in the absence of the compound, so as to determine whether the compound is an inducer of Mda-5 gene expression and an inducer of terminal differentiation of the cell.

A method for treating cancer in a subject suffering therefrom which comprises administering to the subject an effective amount of a compound identified by the method of identifying an inducer of Mda-5 gene expression described herein and a pharmaceutically acceptable carrier, so as to induce terminal differentiation of the cancer cells in the subject and thereby treat the cancer.

Definitions

As used herein "therapeutic gene" means DNA encoding an amino acid sequence corresponding to a functional protein capable of exerting a therapeutic effect on cancer cells or having a regulatory effect on the expression of a function in cells.

As used herein "nucleic acid molecule" includes both DNA and RNA and, unless otherwise specified, includes both double-stranded and single-stranded nucleic acids. Also included are hybrids such as DNA-RNA hybrids. Reference to a nucleic acid sequence can also include modified bases as long as the modification does not significantly interfere either with binding of a ligand such as a protein by the nucleic acid or Watson-Crick base pairing.

As used herein "Mda-5 promoter" means the promoter having about 1000 base pairs (bp) derived from the 5' flanking region of the Mda-5 gene as shown in FIG. 10. See SEQ ID NO:3 as follows.

Mda-5 cDNA (SEQ ID NO:1) and Mda-5 polypeptide (SEQ ID NO:2)

```
Mda-5 cDNA (SEQ ID NO:1)
GCGCGCCGGC CTGAGAGCCC TGTGGACAAC CTCGTCATTG

TCAGGCACAG AGCGGTAGAC CCTGCTTCTC TAAGTGGGCA

GCGGACAGCG GCACGCACAT TTCACCTGTC CCGCAGACAA

CAGCACCATC TGCTTGGGAG AACCCTCTCC CTTCTCTGAG

AAAGAAAGAT GTCGAATGGG TATTCCACAG ACGAGAATTT

CCGCTATCTC ATCTCGTGCT TCAGGGCCAG GGTGAAAATG

TACATCCAGG TGGAGCCTGT GCTGGACTAC CTGACCTTTC

TGCCTGCAGA GGTGAAGGAG CAGATTCAGA GGACAGTCGC

CACCTCCGGG AACATGCAGG CAGTTGAACT GCTGCTGAGC

ACCTTGGAGA AGGGAGTCTG GCACCTTGGT TGGACTCGGC

AATTCGTGGA GGCCCTCCGG AGAACCGGCA GCCCTCTGGC

CGCCCGCTAC ATGAACCCTG AGCTCACCGA CTTGCCCTCT

CCATCGTTTG AGAACGCTCA TGATGAATAT CTCCAACTGC

TGAACCTCCT TCAGCCCACT CTGGTGGACA AGCTTCTAGT

TAGAGACGTC TTGGATAAGT GCATGGAGGA GGAACTGTTG

ACAATTGAAG ACAGAAACCG GATTGCTGCT GCAGAAAACA

ATGGAAATGA ATCAGGTGTA AGAGAGCTAC TAAAAAGGAT

TGTGCAGAAA GAAAACTGGT TCTCTGCATT TCTGAATGTT

CTTCGTCAAA CAGGAAACAA TGAACTTGTC CAAGAGTTAA

CAGGCTCTGA TTGCTCAGAA AGCAATGCAG AGATTGACAA

TTTATCACAA GTTGATGGTC CTCAAGTGGA AGAGCAACTT

CTTTCAACCA CAGTTCAGCC AAATCTGGAG AAGGAGGTCT

GGGGCATGGA GAATAACTCA TCAGAATCAT CTTTTGCAGA

TTCTTCTGTA GTTTCAGAAT CAGACACAAG TTTGGCAGAA

GGAAGTGTCA GCTGCTTAGA TGAAAGTCTT GGACATAACA

GCAACATGGG CAGTGATTCA GGCACCATGG GAAGTGATTC

AGATGAAGAG AATGTGGCAG CAAGAGCATC CCCGGAGCCA

GAACTCCAGC TCAGGCCTTA CCAAATGGAA GTTGCCCAGC

CAGCCTTGGA AGGGAACAAT ATCATCATCT GCCTCCCTAC

AGGGAGTGGA AAAACCAGAG TGGCTGTTTA CATTGCCAAG

GATCACTTAG ACAAGAAGAA AAAAGCATCT GAGCCTGGAA

AAGTTATAGT TCTTGTCAAT AAGGTACTGC TAGTTGAACA

GCTCTTCCGC AAGGAGTTCC AACCATTTTT GAACAAATGG

TATCGTGTTA TTGGATTAAG TGGTGATACC CAACTGAAAA

TATCATTTCC AGAAGTTGTC AAGTCCTGTG ATATTATTAT

CAGTACAGCT CAAATCCTTG AAAACTCCCT CTTAAACTTG

GAAAATGGAG AAGATGCTGG TGTTCAATTG TCAGACTTTT

CCCTCATTAT CATTGATGAA TGTCATCACA CCAACAAAGA

AGCAGTGTAT AATAACATCA TGAGGCATTA TTTGATGCAG

AAGTTGAAAA ACAATAGACT CAAGAAAGAA AACAAACCAG

TGATTCCCCT TCCTCAGATA CTGGGACTAA CAGCTTCACC

TGGTGTTGGA GGGGCCACGA AGCAAGCCAA AGCTGAAGAA

CACATTTTAA AACTATGTGC CAATCTTGAT GCATTTACTA

TTAAAACTGT TAAAGAAAAC CTTGATCAAC TGAAAAACCA

AATACAGGAG CCATGCAAGA AGTTTGCCAT TGCAGATGCA

ACCAGAGAAG ATCCATTTAA AGAGAAACTT CTAGAAATAA

TGACAAGGAT TCAAACTTAT TGTCAAATGA GTCCAATGTC

AGATTTTGGA ACTCAACCCT ATGAACAATG GGCCATTCAA

ATGGAAAAAA AAGCTGCAAA AAAAGGAAAT CGCAAAGAAC

GTGTTTGTGC AGAACATTTG AGGAAGTACA ATGAGGCCCT
```

-continued

```
ACAAATTAAT GACACAATTC GAATGATAGA TGCGTATACT
CATCTTGAAA CTTTCTATAA TGAAGAGAAA GATAAGAAGT
TTGCAGTCAT AGAAGATGAT AGTGATGAGG GTGGTGATGA
TGAGTATTGT GATGGTGATG AAGATGAGGA TGATTTAAAG
AAACCTTTGA AACTGGATGA AACAGATAGA TTTCTCATGA
CTTTATTTTT TGAAAACAAT AAAATGTTGA AAAGGCTGGC
TGAAAACCCA GAATATGAAA ATGAAAAGCT GACCAAATTA
AGAAATACCA TAATGGAGCA ATATACTAGG ACTGAGGAAT
CAGCACGAGG AATAATCTTT ACAAAAACAC GACAGAGTGC
ATATGCGCTT TCCCAGTGGA TTACTGAAAA TGAAAAATTT
GCTGAAGTAG GAGTCAAAGC CCACCATCTG ATTGGAGCTG
GACACAGCAG TGAGTTCAAA CCCATGACAC AGAATGAACA
AAAAGAAGTC ATTAGTAAAT TTCGCACTGG AAAAATCAAT
CTGCTTATCG CTACCACAGT GGCAGAAGAA GGTCTGGATA
TTAAAGAATG TAACATTGTT ATCCGTTATG GTCTCGTCAC
CAATGAAATA GCCATGGTCC AGGCCCCTGG TCGAGCCAGA
GCTGATGAGA GCACCTACGT CCTGGTTGCT CACAGTGGTT
CAGGAGTTAT CGAACATGAG ACAGTTAATG ATTTCCGACA
GAAGATGATG TATAAAGCTA TACATTGTGT TCAAAATATG
AAACCAGAGG AGTATGCTCA TAAGATTTTG GAATTACAGA
TGCAAAGTAT AATGGAAAAG AAAATGAAAA CCAAGAGAAA
TATTGCCAAG CATTACAAGA ATAACCCATC ACTAATAACT
TTCCTTTGCA AAAACTGCAG TGTGCTAGCC TGTTCTGGGG
AAGATATCCA TGTAATTGAG AAAATGCATC ACGTCAATAT
GACCCCAGAA TTCAAGGAAC TTTACATTGT AAGAGAAAAC
AAAGCACTGC AAAAGAAGTG TGCCGACTAT CAAATAAATG
GTGAAATCAT CTGCAAATGT GGCCAGGCTT GGGCAACAAT
GATGGTGCAC AAAGGCTTAG ATTTGCCTTG TCTCAAAATA
AGGAATTTTG TAGTGGTTTT CAAAAATAAT TCAACAAAGA
AACAATACAA AAAGTGGGTA GAATTACCTA TCACATTTCC
CAATCTTGAC TATTCAGAAT GCTGTTTATT AGTGATGAG
GATTACCACT TGATTGAAGA TTCTTTTAAA ATACTATCAG
TTAAACATTT AATATCATTA TGATTAATGT ATTCATTATG
CTACAGAACT GACATAAGAA TCAATAAAAT GATTGTTTTA
CTCTG
```

MDA-5 potein sequence (SEQ ID NO:2)
MSNGYSTDEN FRYLISCFRA RVKMYIQVEP VLDYLTFLPA
EVKEQIQRTV ATSCNMQAVE LLLSTLEKCV WHLGWTREFV
EALRRTGSPL AARYMNPELT DLPSPSFENA HDEYLQLLNL LQPTLVDKLL VRDVLDKCME EELLTIEDRN RIAAAENNGN
ESGVRELLKR IVQKENWFSA FLNVLRQTGN NELVQELTGS
DCSESNAEIE NLSQVDGPQV EEQLLSTTVQ PNLEKEVWGM
ENNSSESSFA DSSVVSESDT SLAEGSVSCL DESLCHNSNM
GSDSGTMGSD SDEENVAARA SPEPELQLRP YQMEVAQPAL
EGKNIIICLP TGSGKTRVAV YIAKDHLDKK KKASEPGKVI
VLVNKVLLVE QLFRKEFQPF LKKWYRVIGL SGDTQLKISF
PEVVKSCDII ISTAQILENS LLNLENGEDA GVQLSDFSLI
IIDECHHTNK EAVYNNIMRH YLMQKLKNNR LKKENKPVIP
LPQILGLTAS PGVGGATKQA KAEEHILKLC ANLDAFTIKT
VKENLDQLKN QIQEPCKKFA IADATREDPF KEKLLEIMTR
IQTYCQMSPM SDFGTQPYEQ WAIQMEKKAA KKCNRKERVC
AEHLRKYNEA LQINDTIRMI DAYTHLETFY NEEKDKKFAV
IEDDSDEGGD DEYCDGDEDE DDLKKPLKLD ETDRELMTLF
FENNKMLKRL AENPEYENEK LTKLRNTIME QYTRTEESAR
GIIFTKTRQS AYALSQWITE NEKFAEVGVK AHHLIGAGHS
SEFKPMTQNE QKEVISKFRT GKINLLIATT VAEEGLDIKE
CNIVIRYGLV TNEIAMVQAR GRARADESTY VLVAHSGSGV
IEHETVNDFR EKMMYKAIHC VQNMKPEEYA HKILELQMQS
IMEKKMKTKR NIAKHYKNNP SLITFLCKNC SVLACSGEDI
HVIEKMHHVN MTPEFKELYI VRENKALQKK CADYQINGEI
ICKCGQAWGT MMVHKGLDLP CLKIRNFVVV FKNNSTKKQY
KKWVELPITF PNLDYSECCL FSDED•

Mda-5 promoter sequence (SEQ ID NO:3)
```
GCACATTTTG GCCTACAAAG GACCTTATTG TTAAGGCAGA
ACCTGCTGGG AAAACAAAAT ATCCGCCGGA GGAGCTTTGT
AGAGCGTTGG TCTTGGTGTC AGAGAGAATT CGCTTTCCTT
TTCTGTTTCC CGCGGTGTCC TTAACCAAAG GCCTCCTCTC
TTCACCCGCC CCGACCAAAA GGTGGCGTCT CCCTGAGGAA
ACTCCCTCCC CGCCAGGCAG ATTACGTTTA CAAAGTCCTG
AGAAGAGAAT CGAAACAGAA ACCAAAGTCA GGCAAACTCT
GTAAGAACTG CCTGACAGAA AGCTGGACTC AAAGCTCCTA
CCCGAGTGTG CAGCAGGATC GCCCCGGTCC GGGACCCCAG
GCGCACACCG CAGAGTCCAA AGTGCCGCGC CTGCCGGCCG
CACCTGCCTG CCGCGGCCCC GCGCGCCGCC CCGCTGCCCA
CCTGCCCGCC TGCCCACCTG CCCAGGTGCG AGTGCAGCCC
CGCGCGCCGG CCTGAGAGCC CTGTGGACAA CCTCGTCATT
GTCAGGCACA GAGCGGTAGA CCCTGCTTCT NTAAGTGGGC
```

```
                     -continued
AGCGGACAGC GGCACGCACA TTTCACCTGT CCCGCAGACA

ACAGCACCAT CTGCTTGGGA GAACCCTCTC CCTTCTCTGA

GAAAGAAAGA TGTCGAATGG GTATTCCACA GACGAGAATT

TCCGCTATCT CATCTCGTGC TTCAGGGCCA GGGTGAAAAT

GTACATCCAG GTGGAGCCTG TGCTGGACTA CCTGACCTTT

CTGCCTGCAG AGGTGAAGGA GCAGATTCAG AGGACAGTCG

CCACCTCCGG GAACATGCAG GCAGTTGAAC TGCTGCTGAG

CACCTTGGAG AAGGGAGTCT GGCACCTTGG TTGGACTCGG

GAATTCGTGG AGGCCCTCCG GAGAACCGGC AGCCCTCTGG

CCGCCCGCTA CATGAACCCT GAGCTCACGG ACTTGCCCTC

TCCATCGTTT GAGAACGCTC ATGATGAATA TCTCCAACTG

CTGAACCTCC TTCAGCCCAC TCTGGTGGAC AAGCTT
```

(See also FIG. 10 for the Mda-5 promoter sequence).

As used herein "enhancer element" is a nucleotide sequence that increases the rate of transcription of the therapeutic genes or genes of interest but does not have promoter activity. An enhancer can be moved upstream, downstream, and to the other side of a promoter without significant loss of activity.

Two DNA or polypeptide sequences are "substantially homologous" when at least about 80% (preferably at least about 90%, and most preferably at least about 95%) of the nucleotides or amino acids match over a defined length of the molecule. As used herein, "substantially homologous" also refers to sequences showing identity to the specified DNA or polypeptide sequence. DNA sequences that are substantially homologous can be identified in a Southern hybridization, experiment under, for example, stringent conditions, as defined for that particular system. Defining appropriate hybridization conditions is within the skill of the art. See, e.g., Sambrook et al., supra; DNA Cloning, vols I & II, supra; Nucleic Acid Hybridization, supra.

A sequence "functionally equivalent" to a Mda-5 promoter sequence is one which functions in the same manner as the Mda-5 promoter sequence. Thus, a promoter sequence "functionally equivalent" to the Mda-5 promoter described herein is one which is capable of directing transcription of a downstream coding sequence in substantially similar time-frames of expression and in substantially similar amounts and with substantially similar tissue specificity as the Mda-5 promoter.

In general terms, an "analog" is understood to be a functional equivalent of a given substance and can be a substitute for said substance, including as a therapeutic substitute. An analog also can be a structural equivalent. As used herein, a "Mda-5 analog" is a substance that mimics a biological effect induced and/or mediated by Mda-5. Any substance having such mimetic properties, regardless of the chemical or biochemical nature thereof, can be used as a Mda-5 analog herein. As used herein, an Mda-5 analog can be referred to as a "mimic" or a "mimetic".

A DNA "coding sequence" or a "nucleotide sequence encoding" a particular protein, is a DNA sequence which is transcribed and translated into a polypeptide in vivo or in vitro when placed under the control of appropriate regulatory sequences. The boundaries of the coding sequence are determined by a start codon at the 5'-(amino) terminus and a translation stop codon at the 3'-(carboxy) terminus. A coding sequence can include, but is not limited to, procaryotic sequences, cDNA from eucaryotic mRNA, genomic DNA sequences from eucaryotic (e.g., mammalian) sources, viral RNA or DNA, and even synthetic nucleotide sequences. A transcription termination sequence will usually be located 3' to the coding sequence.

DNA "control sequences" refers collectively to promoter sequences, polyadenylation signals, transcription termination sequences, upstream regulatory domains, enhancers, and the like, untranslated regions, including 5'-UTRs and 3'-UTRs, which collectively provide for the transcription and translation of a coding sequence in a host cell.

"Operably linked" refers to an arrangement of nucleotide sequence elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

A control sequence "directs the transcription" of a coding sequence in a cell when RNA polymerase will bind the promoter sequence and transcribe the coding sequence into mRNA, which is then translated into the polypeptide encoded by the coding sequence.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. In eucaryotic cells, a stably transformed cell is generally one in which the exogenous DNA has become integrated into the chromosome so that it is inherited by daughter cells through chromosome replication, or one which includes stably maintained extrachromosomal plasmids. This stability is demonstrated by the ability of the eucaryotic cell to establish cell lines or clones comprised of a population of daughter cells containing the exogenous DNA.

A "heterologous" region of a DNA construct is an identifiable segment of DNA within or attached to another DNA molecule that is not found in association with the other molecule in nature. For example, a sequence encoding a protein other than an Mda-5 is considered a heterologous sequence when linked to an Mda-5 promoter. Similarly, a sequence encoding an Mda gene (i.e., Mda-6, Mda-7) will be considered heterologous when linked to an Mda gene promoter with which it is not normally associated. Another example of a heterologous coding sequence is a construct where the coding sequence itself is not found in nature (e.g., synthetic sequences having codons different from the native gene). Likewise, a chimeric sequence, comprising a heterologous structural gene and a gene encoding an Mda or a portion of an Mda, linked to an Mda promoter, whether derived from the same or a different Mda gene, will be considered heterologous since such chimeric constructs are not normally found in nature. Allelic variation or naturally occurring mutational events do not give rise to a heterologous region of DNA, as used herein.

Vectors

Especially preferred are virus based vectors. In the case of eukaryotic cells, retrovirus or adenovirus based vectors are preferred. Such vectors contain all or a part of a viral genome, such as long term repeats ("LTRs"), promoters (e.g., CMV promoters, SV40 promoter, RSV promoter), enhancers, and so forth. When the host cell is a prokaryote, bacterial viruses, or phages, are preferred. Exemplary of such vectors are vectors based upon, e.g., lambda phage. In any case, the vector may comprise elements of more than one virus.

The resulting vectors are transfected or transformed into a host cell, which may be eukaryotic or prokaryotic.

The gene transfer vector of the present invention may additionally comprise a gene encoding a marker or reporter molecule to more easily trace expression of the vector.

Examples of such reporter molecules which can be employed in the present invention are well-known in the art and include beta-galactosidase (Fowler et al, Proc. Natl. Acad. Sci., USA, 74:1507 (1977)), luciferase (Tu et al, Biochem., 14:1970 (1975)), and chloramphenicol acetyltransferase (Gorman et al, Mol. Cell. Biol., 2:1044–1051 (1982)).

The gene transfer vector may contain more than one gene encoding the same or different foreign polypeptides or RNAs.

The gene transfer vector may be any construct which is able to replicate within a host cell and includes plasmids, DNA viruses, retroviruses, as well as isolated nucleotide molecules. Liposome-mediated transfer of the gene transfer vector may also be carried out in the present invention.

Examples of such plasmids which can be employed in the present invention include pGL3-based plasmids (Promega). An example of such DNA viruses which can be employed in the present invention are adenoviruses.

Adenoviruses have attracted increasing attention as expression vectors, especially for human gene therapy (Berkner, Curr. Top. Microbiol. Immunol., 158:39–66 (1992)).

Examples of such adenovirus serotypes which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408–441 (1986)). Ad5 of subgroup C is the preferred adenovirus employed in the present invention. This is because Ad5 is a human adenovirus about which a great deal of biochemical and genetic information is known, and it has historically been used for most constructions employing adenovirus as a vector. Also, adenoviral vectors are commercially available, e.g., pCA3 (Microbix Biosystems Inc.).

Methods for producing adenovirus vectors are well-known in the art (Berkner et al, Nucleic Acids Res., 11:6003–6020 (1983); van Doren et al, Mol. Cell. Biol., 4:1653–1656 (1984); Ghosh-Choudhury et al, Biochem. Biophys. Res. Commun., 147:964–973 (1987); McGrory et al, Virol., 163:614–617 (1988); and Gluzman et al, In: Eurkaryotic Viral Vectors, Ed. Gluzman, Y. pages 187–192, Cold Spring Harbor Laboratory (1982)).

Functionally Equivalent

Nucleic acid molecules which are "functionally equivalent" to Mda-5 promoter or Mda-5 cDNA retain the functional properties of the Mda-5 cDNA or MDA-5 promoter. The nucleic acid molecule may be a derivative of the Mda-5 cDNA or promoter such that there are substitutions, deletions, insertions or alterations in the nucleotide sequence which do not alter substantially the function of the nucleic acid. For example, a promoter molecule which is a functional equivalent of Mda-5 promoter having such substitutions will still permit the tissue specific expression of a gene of interest operably linked thereto and expressed in an organism.

Modification is permitted so long as the derivative molecules retain its increased potency compared to Mda-5 promoter alone and its tissue specificity. A functional equivalent of Mda-5 cDNA will encode a protein which retains substantially the same biological functions which are characteristic of Mda-5.

The promoter of the present invention in one embodiment is operably linked to a gene of interest. Such a gene of interest is preferably a therapeutic gene. Examples of therapeutic genes include suicide genes, envisioned for the treatment of cancer, for example. These are genes sequences the expression of which produces a protein or agent that inhibits tumor cell growth or induces tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill cancer cells or produce cytokines or other cytotoxic agents which directly or indirectly inhibit the growth of or kill the cancer cell.

Suitable enzymes include thymidine kinase (TK), xanthine-guanine phosphoribosyltransferase (GPT) gene from *E. coli* or *E. coli* cytosine deaminase (CD), or hypoxanthine phosphoribosyl transferase (HPRT).

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include *Pseudomonas* exotoxin A and S; diphtheria toxin (DT); *E. coli* LT toxins, Shiga toxin, Shiga-like toxins (SLT-1, -2), ricin, abrin, supporin, and gelonin.

In one embodiment, the gene of interest is a cytokine. Suitable cytokines include interferons, GM-CSF interleukins, tumor necrosis factor (TNF) (Wong G, et al., Human GM-CSF: Molecular cloning of the complementary DNA and purification of the natural and recombinant proteins. Science 1985; 228:810); WO9323034 (1993); Horisberger M. A., et al., Cloning and sequence analyses of cDNAs for interferon-beta and virus-induced human Mx proteins reveal that they contain putative guanine nucleotide-binding sites: functional study of the corresponding gene promoter. Journal of Virology, 1990 March, 64(3):1171–81; Li Y P et al., Proinflammatory cytokines tumor necrosis factor-alpha and IL-6, but not IL-1, down-regulate the osteocalcin gene promoter. Journal of Immunology, Feb. 1, 1992, 148(3): 788–94; Pizarro T. T., et al. Induction of TNF alpha and TNF beta gene expression in rat cardiac transplants during allograft rejection. Transplantation, 1993 August, 56(2): 399–404). (Breviario F., et al., Interleukin-1-inducible genes in endothelial cells. Cloning of a new gene related to C-reactive protein and serum amyloid P component. Journal of Biological Chemistry, Nov. 5, 1992, 267(31):22190–7; Espinoza-Delgado I., et al., Regulation of IL-2 receptor subunit genes in human monocytes. Differential effects of IL-2 and IFN-gamma. Journal of Immunology, Nov. 1, 1992, 149(9):2961–8; Algate P. A., et al., Regulation of the interleukin-3 (IL-3) receptor by IL-3 in the fetal liver-derived FL5.12 cell line. Blood, 1994 May 1, 83(9):2459–68; Cluitmans F. H., et al., IL-4 down-regulates IL-2-, IL-3-, and GM-CSF-induced cytokine gene expression in peripheral blood monocytes. Annals of Hematology, 1994 June, 68(6): 293–8; Lagoo, A. S., et al., IL-2, IL-4, and IFN-gamma gene expression versus secretion in superantigen-activated T cells. Distinct requirement for costimulatory signals through adhesion molecules. Journal of Immunology, Feb. 15, 1994, 152(4):1641–52; Martinez O. M., et al., IL-2 and IL-5 gene expression in response to alloantigen in liver allograft recipients and in vitro. Transplantation, 1993 May, 55(5):1159–66; Pang G, et al., GM-CSF, IL-1 alpha, IL-1 beta, IL-6, IL-8, IL-10, ICAM-1 and VCAM-1 gene expression and cytokine production in human duodenal fibroblasts stimulated with lipopolysaccharide, IL-1 alpha and TNF-alpha. Clinical and Experimental Immunology, 1994 June, 96(3):437–43; Ulich T. R., et al., Endotoxin-induced cytokine gene expression in vivo. III. IL-6 mRNA and serum protein expression and the in vivo hematologic effects of IL-6. Journal of Immunology, Apr. 1, 1991, 146(7):2316–23; Mauviel A., et al., Leukoregulin, a T cell-derived cytokine, induces IL-8 gene expression and secretion in human skin fibroblasts. Demonstration and secretion in human skin fibroblasts. Demonstration of enhanced NF-kappa B binding and NF-kappa B-driven promoter activity. Journal of Immunology, Nov. 1, 1992, 149(9):2969–76).

The gene of interest is a growth factor in one embodiment. Growth factors include Transforming Growth Factor-alpha (TGF-alpha) and beta (TGF-beta), cytokine colony stimulating factors (Shimane M., et al., Molecular cloning and characterization of G-CSF induced gene cDNA. Biochemical and Biophysical Research Communications, Feb. 28, 1994, 199(1):26–32; Kay A. B., et al., Messenger RNA expression of the cytokine gene cluster, interleukin 3 (IL-3), IL-4, IL-5, and granulocyte/macrophage colony-stimulating factor, in allergen-induced late-phase cutaneous reactions in atopic subjects. Journal of Experimental Medicine, Mar. 1, 1991, 173(3):775–8; de Wit H, et al., Differential regulation of M-CSF and IL-6 gene expression in monocytic cells. British Journal of Haematology, 1994 February, 86(2):259–64; Sprecher E., et al., Detection of IL-1 beta, TNF alpha, and IL-6 gene transcription by the polymerase chain reaction in keratinocytes, Langerhans cells and peritoneal exudate cells during infection with herpes simplex virus-1. Archives of Virology, 1992, 126(1–4):253–69).

Preferred vectors for use in the methods of the present invention are viral including adenoviruses, retroviral, vectors, adeno-associated viral (AAV) vectors.

The viral vector selected should meet the following criteria: 1) the vector must be able to infect the tumor cells and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells. These vectors have very broad host and cell type ranges, express genes stably and efficiently. The safety of these vectors has been proved by many research groups. In fact many are in clinical trials.

Other virus vectors that may be used for gene transfer into cells for correction of disorders include retroviruses such as Moloney murine leukemia virus (MoMuLV); papovaviruses such as JC, SV40, polyoma, adenoviruses; Epstein-Barr Virus (EBV); papilloma viruses, e.g. bovine papilloma virus type I (BPV); vaccinia and poliovirus and other human and animal viruses.

Adenoviruses have several properties that make them attractive as cloning vehicles (Bachettis et al.: Transfer of gene for thymidine kinase-deficient human cells by purified herpes simplex viral DNA. PNAS USA, 1977 74:1590; Berkner, K. L.: Development of adenovirus vectors for expression of heterologous genes. Biotechniques, 1988 6:616; Ghosh-Choudhury G., et al., Human adenovirus cloning vectors based on infectious bacterial plasmids. Gene 1986; 50:161; Hag-Ahmand Y., et al., Development of a helper-independent human adenovirus vector and its use in the transfer of the herpes simplex virus thymidine kinase gene. J Virol 1986; 57:257; Rosenfeld M., et al., Adenovirus-mediated transfer of a recombinant .alpha..sub.1-antitrypsin gene to the lung epithelium in vivo. Science 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period up to 4 weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; identification of the component necessary for adenovirus translational control and their utilization in cDNA expression vectors. PNAS USA, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. an efficient deletion mutant packaging system for a defective herpes simplex virus vectors: Potential applications to human gene therapy and neuronal physiology. PNAS USA, 1990 87:8950).

Another vector for mammalian gene transfer is the bovine papilloma virus-based vector (Sarver N, et al., Bovine papilloma virus DNA: A novel eukaryotic cloning vector. Mol Cell Biol 1981; 1:486). Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. Proc Natl Acad Sci USA 1982; 79:4927; Smith et al. infectious vaccinia virus recombinants that express hepatitis B virus surface antigens. Nature, 1983 302:490.)

Retroviruses are packages designed to insert viral genes into host cells (Guild B, et al., Development of retrovirus vectors useful for expressing genes in cultured murine embryonic cells and hematopoietic cells in vivo. J Virol 1988; 62:795; Hock R. A., et al., Retrovirus mediated transfer and expression of drug resistance genes in human hemopoietic progenitor cells. Nature 1986; 320:275).

The basic retrovirus consists of two identical strands of RNA packaged in a proviral protein. The core surrounded by a protective coat called the envelope, which is derived from the membrane of the previous host but modified with glycoproteins contributed by the virus.

Markers and amplifiers can also be employed in the gene transfer vectors of the invention. A variety of markers are known which are useful in selecting for transformed cell lines and generally comprise a gene whose expression confers a selectable phenotype on transformed cells when the cells are grown in an appropriate selective medium. Such markers for mammalian cell lines include, for example, the bacterial xanthine-guanine phosporibosyl transferase gene, which can be selected for in medium containing mycophenolic acid and xanthine (Mulligan et al. (1981) Proc. Natl. Acad. Sci. USA 78:2072–2076), and the aminoglycoside phosphotransferase gene (specifying a protein that inactivates the antibacterial action of neomycin/kanamycin derivatives), which can be selected for using medium containing neomycin derivatives such as G418 which are normally toxic to mammalian cells (Colbere-Garapin et al. (1981) J. Mol. Biol. 150:1–14). Useful markers for other eucaryotic expression systems, are well known to those of skill in the art.

Infection of cells can be carried out in vitro or in vivo. In vitro infection of cells is performed by adding the gene transfer vectors to the cell culture medium. When infection is carried out in vivo, the solution containing the gene transfer vectors may be administered by a variety of modes, depending on the tissue which is to be infected. Examples of such modes of administration include injection of gene transfer vectors into the skin, topical application onto the skin, direct application to a surface of epithelium, or instillation into an organ (e.g., time release patch or capsule below the skin or into a tumor), oral administration, injection into the cerebro-spinal fluid, intranasal application, application into eye by dropper, etc.

Expression can be amplified by placing an amplifiable gene, such as the mouse dihydrofolate reductase (dhfr) gene adjacent to the coding sequence. Cells can then be selected for methotrexate resistance in dhfr-deficient cells. See, e.g. Urlaub et al. (1980) Proc. Natl. Acad. Sci. USA 77:4216–4220; Rungold et al. (1981) J. Mol. and Appl. Genet. 1:165–175.

The above-described system can be used to direct the expression of a wide variety of procaryotic, eucaryotic and viral proteins, (genes of interest) including, for example, viral glycoproteins suitable for use as vaccine antigens, immunomodulators for regulation of the immune response, hormones, cytokines and growth factors, as well as proteins useful in the production of other biopharmaceuticals.

It may also be desirable to produce mutants or analogs of the proteins of interest. See description of "functionally equivalent" nucleic acids hereinabove. Such mutants or analogs of the proteins of interest in one embodiment are expressed from functionally equivalent nucleic acids of the gene of interest or of Mda-5 cDNA.

Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

For purposes of the present invention, it may be desirable to further engineer the coding sequence to effect secretion of the polypeptide from the host organism. This enhances clone stability and prevents the toxic build up of proteins in the host cell so that expression can proceed more efficiently. Homologous signal sequences can be used for this purpose with proteins normally found in association with a signal sequence. Additionally, heterologous leader sequences which provide for secretion of the protein can be added to the constructs. Preferably, processing sites will be included such that the leader fragment can be cleaved from the protein expressed therewith. (See, e.g., U.S. Pat. No. 4,336,246 for a discussion of how such cleavage sites can be introduced). The leader sequence fragment typically encodes a signal peptide comprised of hydrophobic amino acids.

In one embodiment of the invention, a heterologous gene sequence, i.e., a therapeutic gene, is inserted into the nucleic acid molecule of the invention. Other embodiments of the isolated nucleic acid molecule of the invention include the addition of a single enhancer element or multiple enhancer elements which amplify the expression of the heterologous therapeutic gene without compromising tissue specificity.

The transformation procedure used depends upon the host to be transformed. Mammalian cells can conveniently be transformed using, for example, DEAE-dextran based procedures, calcium phosphate precipitation (Graham, F. L. and Van der Eb, A. J. (1973) Virology 52:456–467), protoplast fusion, liposome-mediated transfer, polybrene-mediated transfection and direct microinjection of the DNA into nuclei. Bacterial cells will generally be transformed using calcium chloride, either alone or in combination with other divalent cations and DMSO (Sambrook, Fritsch & Maniatis, Molecular Cloning: A Laboratory Manual, Second Edition (1989)). DNA can also be introduced into bacterial cells by electroporation. Methods of introducing exogenous DNA into yeast hosts typically include either the transformation of spheroplasts or transformation of intact yeast cells treated with alkali cations.

The constructs can also be used in gene therapy or nucleic acid immunization, to direct the production of the desired gene product in vivo, by administering the expression constructs directly to a subject for the in vivo translation thereof. See, e.g. EPA Publication No. 336,523 (Dreano et al., published Oct. 11, 1989). Alternatively, gene transfer can be accomplished by transfecting the subject's cells or tissues with the expression constructs ex vivo and reintroducing the transformed material into the host. The constructs can be directly introduced into the host organism, i.e., by injection (see International Publication No. WO/90/11092; and Wolff et al., (1990) Science 247:1465–1468). Liposome-mediated gene transfer can also be accomplished using known methods. See, e.g., Hazinski et al., (1991) Am. J. Respir. Cell Mol. Biol. 4:206–209; Brigham et al. (1989) Am. J. Med. Sci. 298:278–281; Canonico et al. (1991) Clin. Res. 39:219A; and Nabel et al. (1990) Science 249:1285–1288. Targeting agents, such as antibodies directed against surface antigens expressed on specific cell types, can be covalently conjugated to the liposomal surface so that the nucleic acid can be delivered to specific tissues and cells for local administration.

Human Gene Therapy and Diagnostic Use of Vector

There are several protocols for human gene therapy which have been approved for use by the Recombinant DNA Advisory Committee (RAC) which conform to a general protocol of target cell infection and administration of transfected cells (see for example, Blaese, R. M. et al., 1990; Anderson, W. F., 1992; Culver, K. W. et al., 1991). In addition, U.S. Pat. No. 5,399,346 (Anderson, W. F. et al., Mar. 21, 1995, U.S. Ser. No. 220,175) describes procedures for retroviral gene transfer. The contents of these support references are incorporated in their entirety into the subject application. Retroviral-mediated gene transfer requires target cells which are undergoing cell division in order to achieve stable integration hence, cells are collected from a subject often by removing blood or bone marrow. It may be necessary to select for a particular subpopulation of the originally harvested cells for use in the infection protocol. Then, a retroviral vector containing the gene(s) of interest would be mixed into the culture medium. The vector binds to the surface of the subject's cells, enters the cells and inserts the gene of interest randomly into a chromosome. The gene of interest is now stably integrated and will remain in place and be passed to all of the daughter cells as the cells grow in number. The cells may be expanded in culture for a total of 9–10 days before reinfusion (Culver et al., 1991). As the length of time the target cells are left in culture increases, the possibility of contamination also increases, therefore a shorter protocol would be more beneficial.

This invention provides for the construction of retrovirus vectors containing the Mda-5 cDNA in a replicable gene transfer vector or Mda-5 promoter linked to a gene of interest for use in gene therapy or for diagonistic uses. The efficiency of transduction of these vectors can be tested in cell culture systems.

USES OF THE COMPOSITIONS OF THE INVENTION

This invention involves targeting a gene-of-interest to the a cancer cell so that the protein encoded by the gene is expressed and directly or indirectly ameliorate the diseased state.

After infecting a susceptible cell, the transgene driven by a specific promoter in the vector expresses the protein encoded by the gene. The use of the highly specific gene vector will allow selective expression of the specific genes in cancer cells.

In one embodiment, the present invention relates to a process for administering modified vectors into the skin to treat skin cancer or disorders associated with the skin. More particularly, the invention relates to the use of vectors carrying functional therapeutic genes to produce molecules that are capable of directly or indirectly affecting cells in the skin to repair damage sustained by the cells from defects, disease or trauma.

Preferably, for treating cancer or for treating defects, disease or damage of cells in the skin, vectors of the invention include a therapeutic gene or transgenes, for example a gene encoding TK. The genetically modified vectors are administered into the skin to treat defects, disease such as skin cancer by introducing a therapeutic gene product or products into the skin that enhance the production of endogenous molecules that have ameliorative effects in vivo.

The basic tasks in the present method of the invention are isolating the gene of interest, selecting the proper vector vehicle to deliver the gene of interest to the body, administering the vector having the gene of interest into the body, and achieving appropriate expression of the gene of interest. The present invention provides packaging the cloned genes, i.e. the genes of interest, in such a way that they can be injected directly into the bloodstream or relevant organs of patients who need them. The packaging will protect the foreign DNA from elimination by the immune system and direct it to appropriate tissues or cells.

In one embodiment of the invention, the gene of interest (desired coding sequence) is a tumor suppressor gene. The tumor suppressor gene may be p21, RB (retinoblastoma) or p53. One of skill in the art would know of other tumor suppressor genes. Recent U.S. Pat. Nos. 6,025,127 and 5,912,236 are hereby incorporated by reference to more explicitly describe the state of the art as to tumor suppressor genes.

Along with the human or animal gene of interest another gene, e.g., a selectable marker, can be inserted that will allow easy identification of cells that have incorporated the modified retrovirus. The critical focus on the process of gene therapy is that the new gene must be expressed in target cells at an appropriate level with a satisfactory duration of expression.

The methods described below to modify vectors and administering such modified vectors into the skin are merely for purposes of illustration and are typical of those that might be used. However, other procedures may also be employed, as is understood in the art.

Most of the techniques used to construct vectors and the like are widely practiced in the art, and most practitioners are familiar with the standard resource materials which describe specific conditions and procedures. However, for convenience, the following paragraphs may serve as a guideline.

General Methods for Vector Construction

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes (See, e.g. New England Biolabs Product Catalog). In general, about 1 μg of plasmid or DNA sequences is cleaved by one unit of enzyme in about 20 μl of buffer solution. Typically, an excess of restriction enzyme is used to insure complete digestion of the DNA substrate.

Incubation times of about one hour to two hours at about 37 degree. C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods in Enzymology 65:499–560 (1980). Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20.degree. C. to 25.degree. C. in 50 mM Tris (pH 7.6) 50 mM NaCl, 6 mM $MgCl_2$, 6 mM DTT and 5–10.mu.M dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 10–50 µl volumes under the following standard conditions and temperatures using T4 DNA ligase. Ligation protocols are standard (D. Goeddel (ed.) Gene Expression Technology: Methods in Enzymology (1991)). In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Alternatively, religation can be prevented in vectors which have been double digested by additional restriction enzyme digestion of the unwanted fragments.

Suitable vectors include viral vector systems e.g. ADV, RV, and AAV (R. J. Kaufman "Vectors used for expression in mammalian cells" in Gene Expression Technology, edited by D. V. Goeddel (1991).

Many methods for inserting functional DNA transgenes into cells are known in the art. For example, non-vector methods include nonviral physical transfection of DNA into cells; for example, microinjection (DePamphilis et al., Bio-Technique 6:662–680 (1988)); liposomal mediated transfection (Felgner et al., Proc. Natl. Acad. Sci. USA, 84:7413–7417 (1987), Felgner and Holm, Focus 11:21–25 (1989) and Felgner et al., Proc. West. Pharmacol. Soc. 32: 115–121 (1989)) and other methods known in the art.

Administration of Modified Vectors into Subject

One way to get DNA into a target cell is to put it inside a membrane bound sac or vesicle such as a spheroplast or liposome, or by calcium phosphate precipitation ($CaPO_4$) (Graham F. and Van der Eb, A., Virology 52:456 1973; Schaefer-Ridder M., et al., Liposomes as gene carriers: Efficient transduction of mouse L cells by thymidine kinase gene. Science 1982; 215:166; Stavridis J. C., et al., Construction of transferrin-coated liposomes for in vivo transport of exogenous DNA to bone marrow erythroblasts in rabbits. Exp Cell Res 1986; 164:568–572).

A vesicle can be constructed in such a way that its membrane will fuse with the outer membrane of a target cell. The vector of the invention in vesicles can home into the cancer cells.

The spheroplasts are maintained in high ionic strength buffer until they can be fused through the mammalian target cell using fusogens such as polyethylene glycol.

Liposomes are artificial phospholipid vesicles. Vesicles range in size from 0.2 to 4.0 micrometers and can entrap 10% to 40' of an aqueous buffer containing macromolecules. The liposomes protect the DNA from nucleases and facilitate its introduction into target cells. Transfection can also occur through electroporation. Before administration, the modified vectors are suspended in complete PBS at a selected density for injection. In addition to PBS, any osmotically balanced solution which is physiologically compatible with the subject may be used to suspend and inject the modified vectors into the host.

For injection, the cell suspension is drawn up into the syringe and administered to anesthetized recipients. Multiple injections may be made using this procedure. The viral suspension procedure thus permits administration of genetically modified vectors to any predetermined site in the skin, is relatively non-traumatic, allows multiple administrations simultaneously in several different sites or the same site using the same viral suspension. Multiple injections may consist of a mixture of therapeutic genes.

Survival of the Modified Vectors so Administered

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, N.Y. (1982)).

Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)).

The present invention provides methods for maintaining and increasing expression of therapeutic genes using a tissue specific promoter.

In addition to using viral and non-viral promoters to drive therapeutic gene expression, an enhancer sequence may be used to increase the level of therapeutic gene expression. Enhancers can increase the transcriptional activity not only of their native gene but also of some foreign genes (Armelor, Proc. Natl. Acad. Sci. USA 70:2702 (1973)).

For example, in the present invention, CMV enhancer sequences are used with the Mda-5 promoter to increase therapeutic gene expression. Therapeutic gene expression may also be increased for long term stable expression after injection using cytokines to modulate promoter activity.

The methods of the invention are exemplified by preferred embodiments in which modified vectors carrying a therapeutic gene are injected intracerebrally into a subject.

The most effective mode of administration and dosage regimen for the molecules of the present invention depends upon the exact location of the melanoma being treated, the severity and course of the cancer, the subject's health and response to treatment and the judgment of the treating physician. Accordingly, the dosages of the molecules should be titrated to the individual subject. The molecules may be delivered directly or indirectly via another cell, autologous cells are preferred, but heterologous cells are encompassed within the scope of the invention.

The interrelationship of dosages for animals of various sizes and species and humans based on $mg/m^2$ of surface area is described by Freireich, E. J., et al. Cancer Chemother., Rep. 50 (4):219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation).

It would be clear that the dose of the molecules of the invention required to achieve cures may be further reduced with schedule optimization.

ADVANTAGES OF THE INVENTION

The Mda-5 promoter of the invention exhibits melanocyte tissue specificity. Since the Mda-5 promoter of the invention is tissue-specific it can only be activated in the targeted tissue, i.e., the skin. Therefore, the genes of interest driven by the Mda-5 promoter will be differentially expressed in these cells, minimizing systemic toxicity.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Melanoma Differentiation Associated Gene-5, Mda-5, a Novel Interferon Inducible Gene with Structural Similarities to RNA Helicases and CARD Motif Containing Proteins Abstract Melanoma differentiation associated gene-5, mda-5, is induced during terminal differentiation in human melanoma cells treated with the combination of recombinant fibroblast interferon (IFN-) and the antileukemic compound mezerein (MEZ). The complete open reading frame of the mda-5 cDNA and its promoter region has now been identified and characterized. Mda-5 encodes a 116.7-kDa protein that contains a caspase recruitment domain (CARD) and an RNA helicase motif. Treatment of HO-1 human melanoma and human skin fibroblast cells with IFN-α, IFN-β, IFN-γ, TNF-α and poly IC induce mda-5 expression. IFN-β and poly IC are the most potent single inducers of mda-5 expression, resulting in a $\geq$5-fold higher induction than with other inducers. Induction of mda-5 expression by IFN-β is also apparent in normal and tumor cell lines of diverse origin. Thus, mda-5 is a novel IFN-β-responsive gene. MEZ, which reversibly induces specific markers of differentiation in HO-1 cells, does not induce mda-5 expression, whereas it increases both the level of steady-state mda-5 mRNA and mda-5 RNA transcription. The finding that most organs, except brain and lung, contain low levels of mda-5 transcripts suggest that the biological role of mda-5 may be closely related to its induction by exogenous agents. Nuclear run-on assays indicate that the level of regulation of mda 5 occurs transcriptionally. The half-life of mda-5 following treatment with IFN-β (or IFN-β+MEZ is between 5~6 hr, confirming that the primary regulation of mda-5 by these agents occurs by enhanced RNA transcription rates. Isolation and characterization of the promoter region of mda 5, provides further documentation that the primary mode of regulation of this gene involves changes in RNA transcription. MDA-5 protein was detected at the predicted size by in vitro translation and Western blot analysis of transiently expressed fusion proteins. GFP-mda-5 fusion proteins were produced and found to localize in the cytoplasm where mda-5 may effects on mRNA translation, mRNA sequestration and decay of specific messages. Ectopic expression of mda-5 reduces the colony-forming efficiency of HO-1 melanoma cells by ~70%, which suggests a growth inhibitory or a pro-apoptotic role of mda-5. In these contexts, mda-5 may play a key role in growth inhibition induced by IFN-β and may also function in apoptotic signaling.

Introduction

Abnormalities in differentiation are common occurrences in human cancers ((1) Fisher and Grant, 1985; (2) Waxman, 1995). Moreover, as cancer cells evolve, ultimately developing new phenotypes or acquiring a further elaboration of preexisting transformation-related properties, the degree of expression of differentiation-associated traits often undergo a further decline. These observations have been exploited as a novel means of cancer therapy in which tumor cells are treated with agents that induce differentiation and a loss of cancerous properties, a strategy called 'differentiation therapy' ((2–4) Waxman et al., 1988, 1991; Jiang et al., 1994; Waxman, 1995). In principle, differentiation therapy may prove less toxic than currently employed chemotherapeutic approaches, including radiation and treatment with toxic chemicals. The ability to develop rational schemes for applying differentiation therapy clinically require appropriate in vitro and in vivo model systems for identifying and characterizing the appropriate agent or agents that can modulate differentiation in cancer cells without causing undue toxicity to normal cells.

Treatment of human melanoma cells with a combination of recombinant human fibroblast interferon (IFN-β) and the antileukemic compound mezerein (MEZ) results in a rapid and irreversible suppression of growth and the induction of terminal cell differentiation ((5) Fisher et al., 1985). This process is associated with a number of changes in cellular phenotype and gene expression ((3, 6–7) Jiang et al., 1993, Jiang et al., 1994). To define the molecular basis of terminal differentiation in human melanoma cells subtraction hybridization has been employed ((8) Jiang and Fisher, 1993). In brief, cDNA libraries were prepared from temporal RNA samples obtained from HO-1 human melanoma cells treated with IFN-β+MEZ and control untreated HO-1 cells and control cDNAs were subtracted away from differentiation-inducer treated cDNAs ((8) Jiang and Fisher, 1993). This approach resulted in an enrichment of genes displaying elevated expression as a function of treatment with the different inducers and the induction of irreversible growth suppression and terminal cell differentiation. Screening of the subtracted differentiation inducer treated HO-1 cDNA library identified both known and novel cDNAs displaying elevated expression in differentiation inducer treated HO-1 cells ((3, 6, 8–14) Jiang and Fisher, 1993; Jiang et al., 1994, 1995, 1996; Lin et al., 1994, 1996; Huang et al., 1999a, 1999b). Four classes of genes, called melanoma differentiation associated (mda) genes, have been cloned using this approach ((8) Jiang and Fisher, 1993). These include genes displaying elevated expression as a function of treatment with: IFN-β and IFN-β+MEZ (Type I mda genes); MEZ and IFN-β+MEZ (Type II mda genes); IFN-β, MEZ and IFN-β+MEZ (Type III mda genes); and predominantly with IFN-β+MEZ ((3,8) Jiang and Fisher, 1993; Jiang et al., 1994). This approach has resulted in the cloning of both known and novel genes involved in important cellular processes, including cell cycle control (mda-6/p21), interferon signaling (ISG-15, ISG-54), cancer growth control (mda-7), immune interferon response (mda-9), transcription control (c-jun, jun-B), immune recognition (HLA Class I) and cell membrane processes (α5 integrin, βa integrin, fibronectin) ((3, 8–15) Jiang and Fisher, 1993; Jiang et al., 1994; Jiang et al., 1995a, 1995b, 1996, 1996; Lin et al., 1994, 1996).

Subtraction hybridization initially identified a small EST named mda-5. Expression of mda-5 was elevated in HO-1 cells treated with IFN-β+MEZ and to a lesser extend by IFN β+IFN-γ. A complete mda-5 cDNA has now been cloned and its properties determined. This gene is a novel early IFN responsive gene, whose activity is increased maximally by treatment with IFN-β and dsRNA. Moreover, the combination of IFN-β+MEZ synergistically induces mda-5 expression in HO-1 and additional cell types, both normal and cancer. The protein structure of MDA-5 indicates potential relationships to RNA helicases and genes containing CARD domains. However, based on the structure of the MDA-5 protein this gene may represent a new member of the helicase gene family. Ectopic expression of mda-5 induces growth suppression, as indicated by a reduction in colony formation, in HO-1 human melanoma cells. Identification, cloning and analysis of upstream genomic sequences have confirmed that the mda-5 gene is responsive at a transcriptional to induction primarily by IFN-β and dsRNA. A potential role for mda-5 in growth suppression induced by IFN and as a molecule involved in the cellular defense mechanism against viral infection is suggested.

Materials and Methods

Cell Culture and Treatment Protocol: HO-1 human melanoma cells, early passage human skin fibroblast (purchased from ATCC) and 293T cells were grown in Dulbecco's modified Eagle's medium supplemented with 10 fetal bovine serum at 37° C. in a 5% CO2/95% air humidified incubator. Prior to treatment, cells were refed with fresh medium and exposed to the indicated compound(s) at the concentrations specified in the figure legends.

Cloning and Sequencing of mda-5: The full length of the mda-5 cDNA was cloned by using the complete open reading frame (C-ORF) technology based on the partial mda-5 EST sequence ((16) Kang and Fisher, 2000). Sequencing was performed by the dye-conjugated dideoxy chain termination method. The ORF of mda-5 was cloned into the SmaI site of pcDEF3 in which mda-5 expression was regulated by the EF-1α promoter. Deletion mutant DN7 (D310-484 spanning the ATPase motif) was constructed by ligation of BamHI-StuI fragment with Klenow-filled AlwNI-NotI fragment into pcDEF3. Antisense mda-5 expression vector was constructed by cloning the 1–1830 bp mda-5 cDNA fragment in an antisense orientation into pcDEF3. GFP-mda-5 fusion expression vector was constructed by ligation of the mda-5 cDNA into the SmaI site of pEGFP-C2. The sequences of the expression vectors were verified as described above.

Northern Blot Analyses and Nuclear Run-On Assays: Total cellular RNA samples were prepared by guanidium isothiocyanate/phenol extraction followed by isopropanol precipitation. Ten 10 μg of total RNA were resolved in 1% agarose gels with formaldehyde and were transferred to Nylon membranes. EcoRI fragment of mda-5 cDNA (2.5 kb) was labeled with 32P using a multiprime labeling kit (Boehringer Mannheim) and used to probe the transferred membrane. Nuclear run-on assays were performed as previously described ((17) Su et al., 1993, 1999). Probes used for nuclear run-on assays were prepared by RT-PCR and included the mda-5 5', 9–837 bp; mda-5 3', 2531–3365 bp; and GAPDH fragment.

In vitro translation: In vitro translation of mda-5 was performed with Novagen's STP3 kit using T7 RNA polymerase with 35S-Methionine as described in the manufacture's protocol. Template for transcription and translation was prepared by BamH1 digestion followed by phenol/chloroform extraction of pGEM-7Zf(+)-mda-5. Proteins that were in vitro translated were resolved in 9% SDS-PAGE and detected by autofluorography.

Transient Transfection Assays: 293T cells were plated 1 day prior to transfection and grown to ~70% confluency. For intracellular localization, sterilized cover slips were placed in culture dishes and cells were seeded at 1×105 cells/6 cm tissue culture plate.

Transient transfection assays were performed using SuperFect from Qiagen as described in the manufacturer's protocol. Ten μg of supercoiled plasmid DNA was transfected into 10 cm-tissue culture dish and cells were harvested two days after transfection.

Western Blot Analysis and Fluorescent Confocal Microscopy: Protein samples were prepared from transiently transfected cells by lysis in RIPA buffer supplemented with protease inhibitors. Twenty μg of protein was resolved in 9 SDS-PAGE and transferred to nitrocellulose membranes. MDA-5 fusion proteins were probed with either α-HA antibody (Boehringer Mannheim) or α-GFP antibody (ClonTech) and HRP-conjugated anti-Mouse IgG (Sigma) and detected by ECL (Amersham). For Fluorescence microscopy, cover glass containing transfected cells were washed with PBS and mounted onto glass slides with mounting medium. Cells were observed with fluorescent confocal microscopy.

Colony-Forming Assays: HO-1 melanoma cells were plated at 8×105 in a 6 cm dish one day prior to transfection. Five μg of supercoiled expression vector DNA was transfected into cells with SuperFect (Qiagen) as described above (18). Two days after transfection, cells were harvested by trypsinization and replated at 10 cells/6-cm dish with complete medium containing 750 μg G418/ml. From each transfection, three dishes were plated. The G418-containing media was replaced once a week for three week. Cells were stained with Giemsa and colonies containing more than 50 cells were counted.

Results

Figure 1A-2:
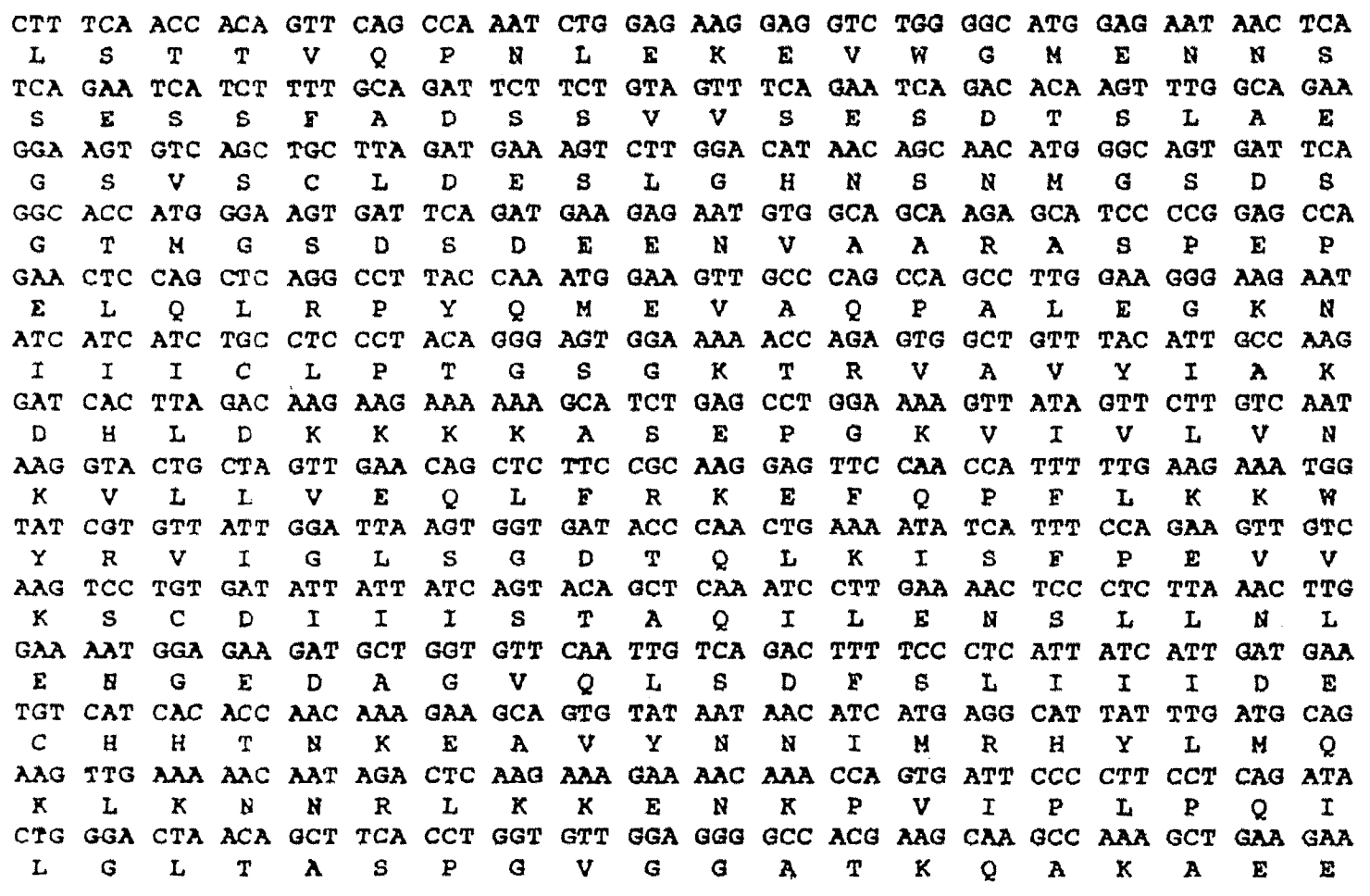

Cloning and Sequence Analysis of mda-5: Subtraction hybridization between a temporally spaced differentiation inducer, IFN-β+mezerein (MEZ), treated HO-1 human melanoma cDNA library and a temporally spaced untreated control HO-1 cDNA library identified a differentially expressed 0.3 kb EST, melanoma differentiation associated gene-5 (mda-5) ((8) Jiang and Fisher, 1993). Northern blotting analysis indicated that the mda-5 EST hybridized with a mRNA species of ~3.8 kb in IFN-β+MEZ treated HO-1 cells ((8) Jiang and Fisher, 1993; Jiang et al., 1994). A full length mda-5 cDNA containing the complete open reading frame (ORF) was obtained using the C-ORF technique (FIG. 1A) ((16) Kang and Fisher, 2000). The ORF of the mda-5 cDNA (3,362 bp excluding the poly A tail) extends from 169 to 3,246 bp and encodes a predicted protein of 1,025 amino acids with a molecular mass of 116.7 kDa. Two ATTTA motifs, which are commonly found in rapid turn-over RNA species, are present at positions 3,225 and 3,284. A poly A signal (AATAAA) is located 23 bp upstream of the poly A tail. A variant of mda-5, named mda-5p which contains an additional 202 bp attached to the 3' end of mda-5 was also identified by screening a placental cDNA library. Since the poly A signal for mda-5p is also located 23 bp upstream of its poly A tail, while the ORF remains constant, mda-5p is possibly an alternatively polyadenylated variant of mda-5. The existence and tissue specific distribution of the two variant forms of mda-5 remains to be determined. However, RT-PCR analysis using HO-1 melanoma cells identified only mda-5 and not mda-5p.

Electronic sequence analysis of the MDA-5 protein using motif and profile scans of proteins presently in the protein database identified two conserved domains, a caspase recruitment domain (CARD) and an RNA helicase domain. The CARD domain which was defined by generalized profile alignment within the RAIDD and ICH-1 amino terminal regions, is present in various apoptotic molecules such as Mch6, ICE, ICH-2, c-IAP1, c-IAP2 and Ced-3. Current evidence suggests that the biological role of CARD is the recruitment of caspase to apoptotic signaling receptor complexes (19). The sequence alignment of N-terminal 50 amino acids (aa 125–174) of MDA-5 with other CARD-proteins reveals significant sequence homology at conserved amino acids of CARD (FIG. 1B). MDA-5 displays the highest homology to the CARD region of RAIDD, which is involved in TNF-R1-mediated apoptotic signal transduction (FIG. 1C) (19). The C-terminal 100 amino acids (aa 722–823) of MDA-5 also show significant sequence homology to the RNA helicase C-terminal conserved domain, which is involved in RNA binding and unwinding of double-stranded RNA (FIG. 1D) (20). In addition, as with other RNA helicases MDA-5 also contains an ATPase A and B motif (331-TGSGKT; SEQ ID NO:14 and 443-DECH; SEQ ID NO:15) (FIG. 1D) (20). However, MDA-5 has unique features in its helicase C-terminal motif and ATPase A motif. MDA-5 has ARGRA (SEQ ID NO:16) instead of the well-conserved YIHRIGRXXR (SEQ ID NO:17) motif, which is critical for RNA binding in other RNA helicases (20). The ATPase A motif of MDA-5 (LPTGSGKT; SEQ ID NO:18) is also different from the consensus sequence motif (A/GXXGXGKT; SEQ ID NO:19) found in other RNA helicases (20). Moreover, MDA-5 is the first putative RNA helicase that retains both an altered RNA binding motif and an ATPase A motif. Screening of the SwissProt database for homologous sequences containing both of these motifs identified three yeast hypothetical ORFs encoding putative helicases (Gen Bank Accession Number Q09884, Q58900 and P34529). The unique features conserved in MDA-5 and these yeast proteins may signify that MDA-5 is a member of a new family of helicases. RNA helicases are known to be involved in diverse cellular processes including RNA splicing, RNA editing, RNA nuclear cytosolic transport, translation and viral replication by ATP-dependent unwinding of dsRNA (20). However, based on the unique structure of MDA-5, it is not possible at present to ascribe a biological role for this new molecule and new family of helicases.

Figure 2B:
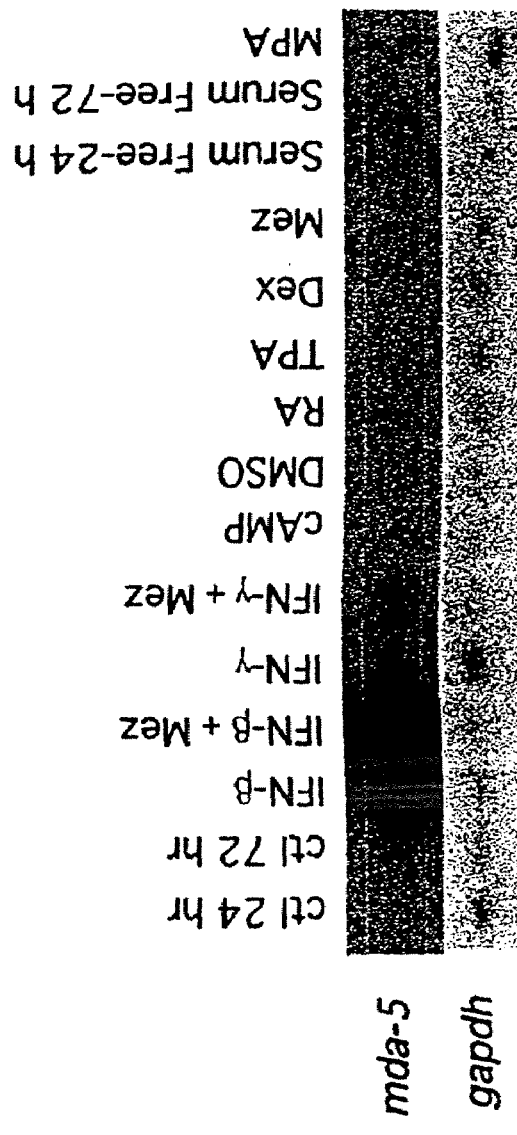

Expression Pattern of mda-5: Since the mda-5 EST was cloned from differentiating HO-1 melanoma cells treated with IFN-β+MEZ, further studies were performed to define the type of molecules capable of regulating mda-5 expression. For this purpose, HO-1 cells were treated with a spectrum of agents affecting growth and differentiation in melanoma cells, including retinoic acid, mycophenolic acid, 12-O-tetradecanoylphobol-13-acetate (TPA) and 3'-5' cyclic AMP. The effect of different types of IFNs and dsRNA (poly IC) and the effect of growth in serum-free medium on mda-5 expression was also evaluated by Northern blotting analyses. As seen in FIG. 2A, steady-state mda-5 message level dramatically increases after treatment with IFN-β or dsRNA. IFN-α (FIG. 4A) and IFN-γ also Increase mda-5 transcript levels, but the magnitude of this effect is less than with IFN-β or dsRNA. Since the other reagents tested ware not effective inducers of mda-5 expression, mda-5 may represent an interferon-responsive, primarily IFN-β-responsive, gene. Although MEZ treatment by itself does not induce mda-5 expression, it can augment mda-5 expression when used in combination with IFN-β and IFN-γ by approximately 3- to 5-fold, respectively (FIG. 2A). A similar expression pattern of mda-5 as seen in HO-1 cells also occurs in human skin fibroblasts treated with IFN-β, IFN-γ or MEZ alone, or in combination (FIG. 2B). Since MEZ co-treatment does not prolong the half-life of the mda-5 transcript (FIG. 7A), augmentation of IFN-β or IFN-γ-induced mda-5 expression might occur at a transcriptional level, possibly by cross-talk between IFN and MEZ signaling pathways.

Figure 3A:
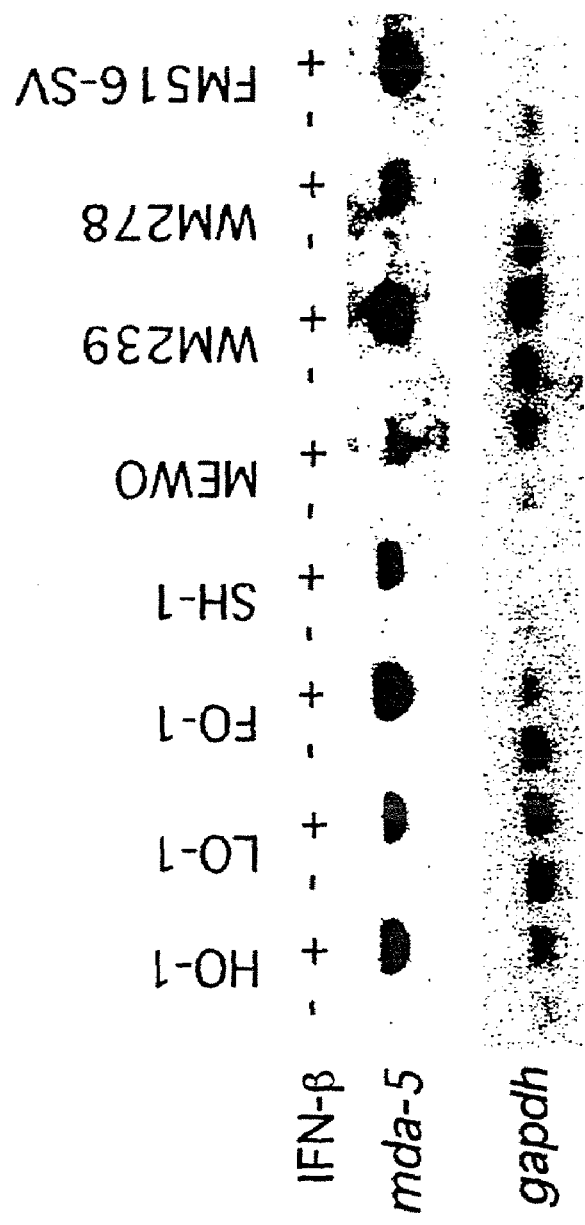
FIGS. 3A–3B. Northern blot analysis of mda-5 expression induced by IFN-β in normal and tumor cell lines. RNA samples were extracted from the indicated cells treated with 2,000 U/ml of interferon-β for 24 hr. Northern hybridization was performed as in Materials and Methods.
Figure 3B:
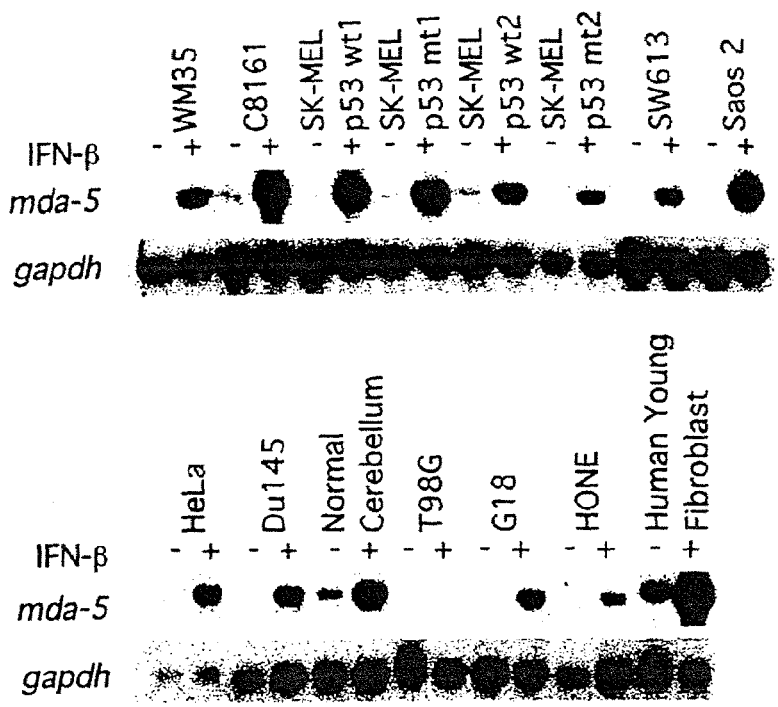

The induction of mda-5 expression by IFN-β also occurs in additional human melanoma cells and in normal and tumor cell lines of diverse origin treated with IFN-β (FIGS. 3A and 3B). The induction of mda-5 expression by IFN-β is independent of the status of p53 and RB. In this context, mda-5 is a bona fide IFN-β-responsive gene that can be induced in a broad spectrum of normal and tumor cell types irrespective of genetic variations present in the different tumor cell lines.

Since IFN signals through membrane receptor associated tyrosine kinases, the inducibility of mda-5 in HO-1 melanoma cells by ligands of other membrane tyrosine kinase receptors including IL-6, EGF, TGF-α, TGF-, TNF-α and PDGF was studied by Northern blotting (FIGS. 4A and 4B). A direct comparison of the potency of induction of mda-5 between different sub-types of IFN was also evaluated (FIGS. 4A and 4B). IFN-β displayed at least a 10-fold higher potency in mda-5 induction than IFN-α or IFN-γ (FIG. 4A) 2E Among the other ligands of membrane receptors, TNF-α induced mda-5 expression at comparable levels as seen with IFN-α (FIG. 4A). A similar pattern of induction of mda-5 expression was also apparent in early passage human skin fibroblasts (FIG. 4B). Therefore, induction of mda-5 expression by IFN-α, IFN-β, IFN-γ and TNF-α is not unique to HO-1 cells, but rather may represent a general response of this gene in diverse cellular contexts. Considering that these agents can produce apoptotic signals in specific target cells, a possible role for MDA-5 in this process, through its CARD domain, is a possibility.

Figure 5:
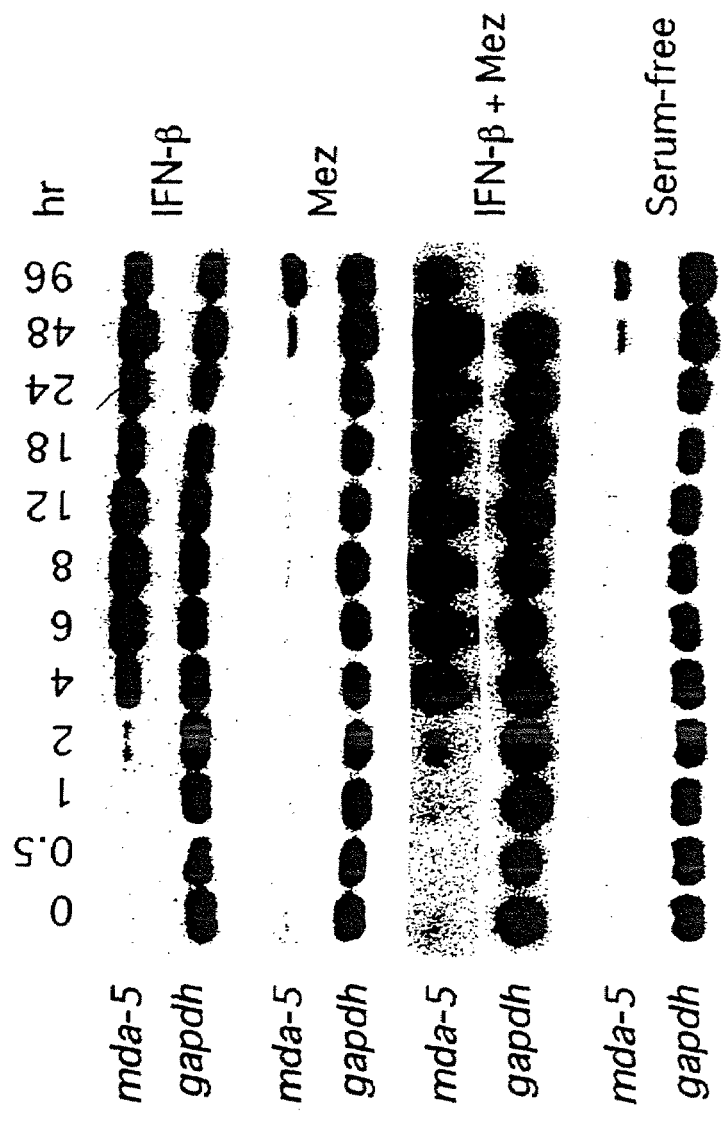
FIG. 5. Northern blot analysis and time course of mda-5 expression. RNA samples were extracted from HO-1 cells treated with the indicated reagents and harvested at the indicated time after treatment. Northern blotting was performed as in Materials and Methods. Abbreviations and concentrations of the indicated reagents are as follows: Mez, mezerein 10 ng/ml; IFN-β, 2,000 U/ml interferon-β; IFN-β+Mez, 2,000 U/ml interferon-β plus mezerein 10 ng/ml.

Treatment of HO-1 cells with IFN-β+MEZ results in terminal differentiation and a concomitant irreversible loss in cellular proliferation (Fisher et al., 1985). Terminal differentiation in the majority of inducer-treated cells occurs within 24 hr of treatment. In this context, the timing of mda-5 expression can provide a clue to the involvement of mda-5 in the induction of differentiation or in the maintenance of the differentiated phenotype. The timing of response to treatment can also provide insights into the mechanism of induction of mda-5. The timing of mda-5 expression was studied by Northern blotting and mda-5 message level began increasing within 2 hr of treatment with IFN-β or IFN-β+MEZ (FIG. 5). The mda-5 message level peaks between 6–8 hr and the elevated level remains elevated over a 96 hr period. Although MEZ further increases mda-5 message level above that observed with IFN-β alone, it does not effect the timing of mda-5 expression. The fast kinetics of mda-5 induction suggested that mda-5 could be an early IFN-β-responsive gene and a major component mediating IFN-β induced growth inhibition and antiviral potency. In contrast, MEZ alone or serum-starvation induced lower levels of mda-5 expression and the timing of induction was delayed (first apparent after 48 hr)(FIG. 5). Judging from the delayed kinetics of mda-5 induction by MEZ treatment and serum-deprivation, this induction could be indirect resulting from the production of a cellular product(s) during the prolonged duration of treatment.

Figure 6:
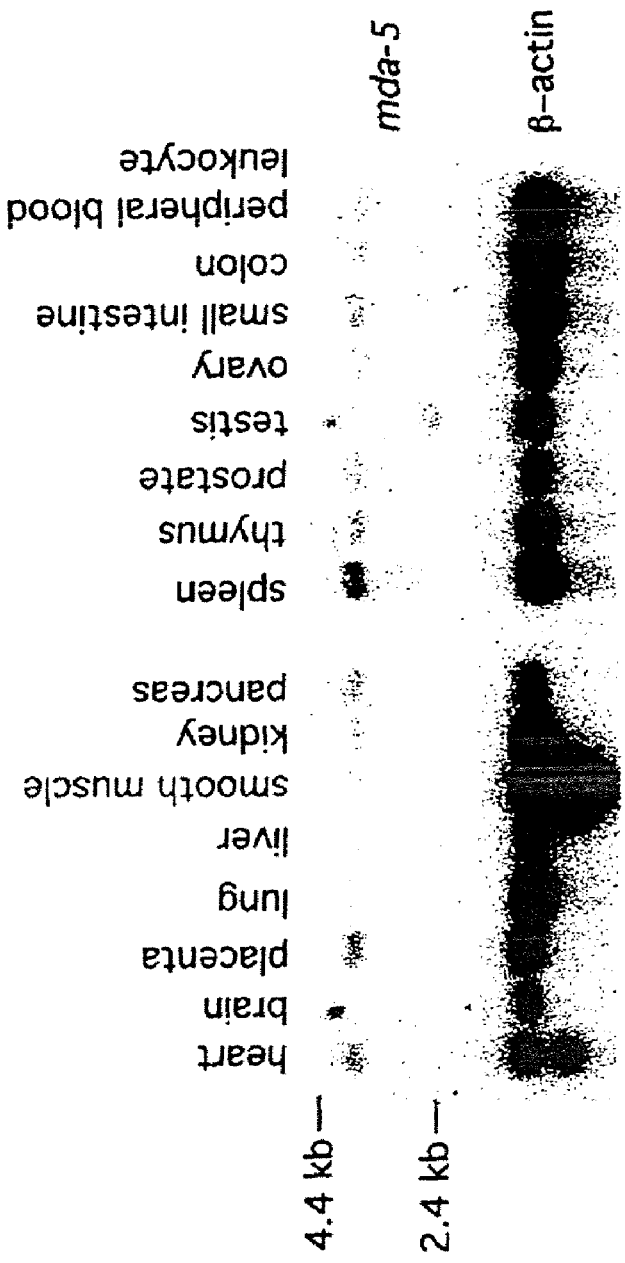
FIG. 6. Northern blot analysis of mda-5 expression in different organs. Multiple tissue Northern blots were purchased from ClonTech. Each lane contains 2 µg of poly A+ RNA. Northern hybridization was performed as described in Materials and Methods.

Organ-Specificity of mda-5 Expression: The organ-specific expression pattern of mda-5 was determined by hybridization of this gene with Poly A+ RNA from different organs immobilized on multiple tissue Northern blots (ClonTech) (FIG. 6). Most organs expressed mda-5 at low levels except in the brain and lung in which expression was barely detectable. In testes, a 2.4 kb band instead of a 3.8 kb band present in the other organs was detected using the mda-5 probe. However, no organ showed noticeably higher levels of expression of mda-5. The highly inducible nature of mda-5 expression by IFNs, especially IFN-β, and TNF-α in diverse cell types and the relatively low basal message level in various organs strongly suggest that mda-5 could play a role in responses that are specific for IFN signaling, but less critical during normal physiological processes.

Figure 7A:
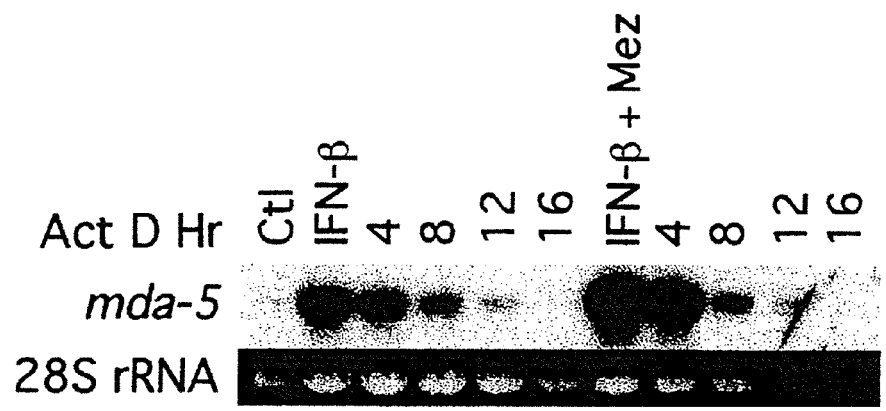
FIGS. 7A–7C. Mechanism of induction of mda-5 expression. A. Northern blot analysis of mda-5. HO-1 melanoma cells were treated with 5 µg/ml actinomycin D 24 hr after incubation with 2,000 U/ml IFN-β or 2,000 U/ml IFN-β+10 ng/ml Mez. Cells were harvested at the indicated time after actinomycin D treatment. Northern hybridization was performed as in Materials and Methods.
Figure 7B:
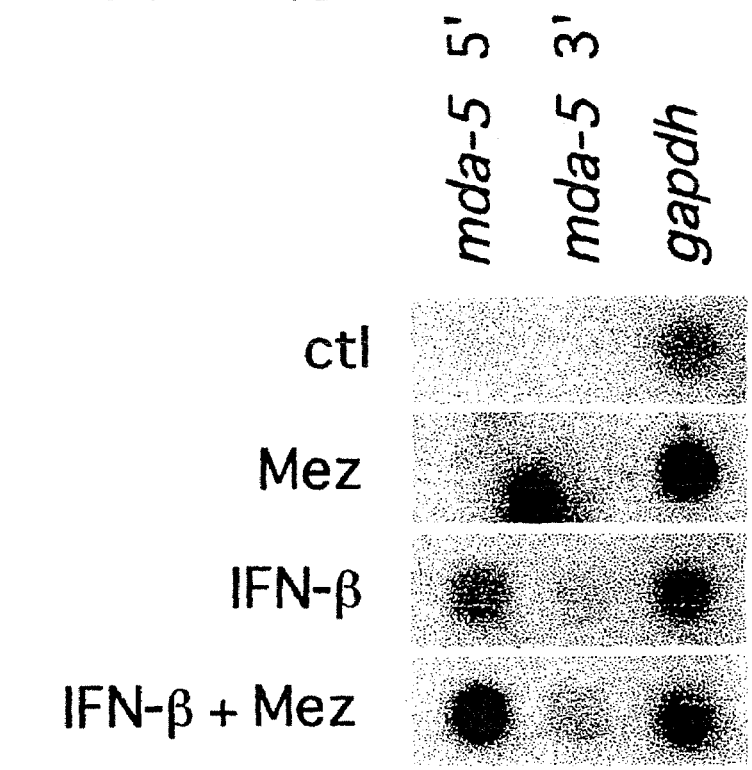

Mechanistic Aspects of mda-5 Induction: Steady state transcript levels of mda-5 were greatly increased during induction of terminal differentiation in HO-1 melanoma cells. The increased mda-5 message level could result from post-transcriptional control, such as message stabilization, or from enhanced transcription. The time course of decay in IFN-β and IFN-β+MEZ induced mda-5 mRNA levels were determined by blocking transcription with actinomycin D. A gradual temporal decrease in mda-5 transcript level after actinomycin D treatment was observed in both IFN-β and IFN-β+MEZ treated cells (FIG. 7A). The half-life of mda-5 transcript in inducer treated HO-1 cells was approximately 5–6 hr. Since the basal level of mda-5 mRNA is too low to monitor quantitatively, effects of IFN-β and IFN-β+MEZ on posttranscriptional control of mda-5 message stability could not be determined. However, since actinomycin D treatment resulted in a decrease in mda-5 message level the induction of mda-5 by IFN-β and IFN-β+MEZ could result from changes in the rate of transcription of this gene. In addition, the fact that the rate of decay in mda-5 message level is not markedly different in IFN-β and IFN-β+MEZ treated cells, mda-5 may also be controlled at a transcriptional level by MEZ when used in combination with IFN-β. Direct evidence for transcriptional control of mda-5 expression by IFN-β and IFN-β+MEZ treatment was provided by nuclear run-off assays (FIG. 7B). Treatment of HO-1 cells with IFN-β greatly increased mda-5 transcription compared with only negligible levels of transcription in untreated or MEZ treated cells. IFN-β+MEZ treatment further enhanced the transcription level of mda-5 $~^{3}$ fold above that of IFN-β alone. These results document that the increased steady state levels of mda-5 message that result from IFN-β and IFN-β+MEZ treatment are the primarily the result of increased mda-5 transcription. As indicated above, MEZ does not increase transcription significantly, but MEZ in combination with IFN-β potentiates mda-5 transcription. Thus, the ability of MEZ+IFN-β to potentiate mda-5 mRNA levels most likely results from a synergistic increase in mda-5 transcription. Since MEZ is recognized as a weak activator of the enzyme protein kinase C (PKC), it is possible that a PKC-dependent augmentation of mda-5 transcription that is initiated by IFN-β signaling occurs following MEZ treatment.

Figure 7C:
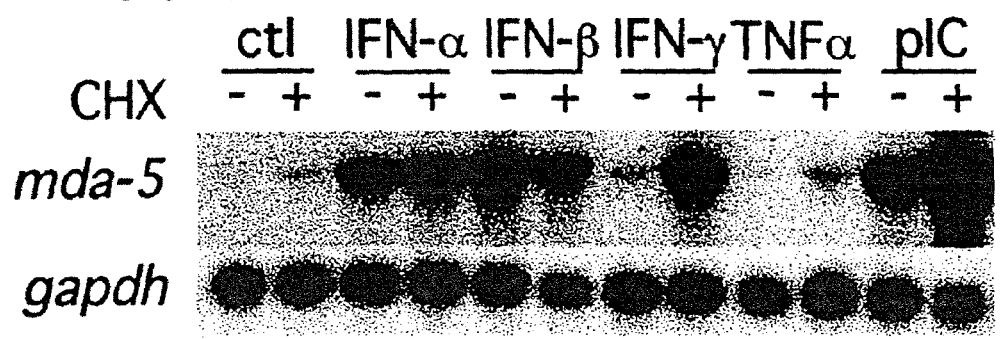

Specific gene expression changes can be altered in response to a signaling event with or without prior protein synthesis. Certain gene expression changes (early response genes) including transcription factors and key signaling molecules do not require protein synthesis prior to their expression. By blocking protein synthesis with cycloheximide, a translation inhibitor, it is possible to determine whether induction of mda-5 expression by appropriate inducer treatment requires or is independent of prior protein synthesis (FIG. 7C). Cycloheximide pre-treatment does not inhibit mda-5 steady-state mRNA levels induced by IFN-α, IFN-β, IFN-γ, TNF-γ and poly IC. Thus, mda-5 is primary response gene that is regulated by IFN-α, IFN-β, IFN-γ, TNF-γ and poly IC treatment. In fact, in certain situations cycloheximide treatment further increased the level of induction of the mda-5 message. This finding suggests that cycloheximide treatment may inhibit the synthesis of a protein(s) that destabilizes mda-5 mRNA.

Figure 8A:
FIGS. 8A–8C. Protein expression of mda-5.
Figure 8B:
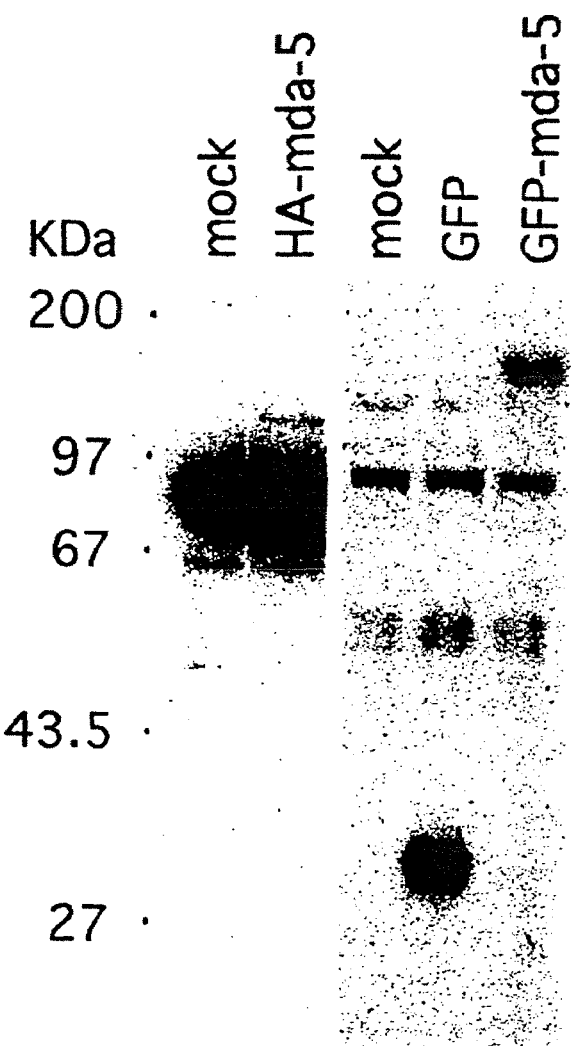
Figure 8C:
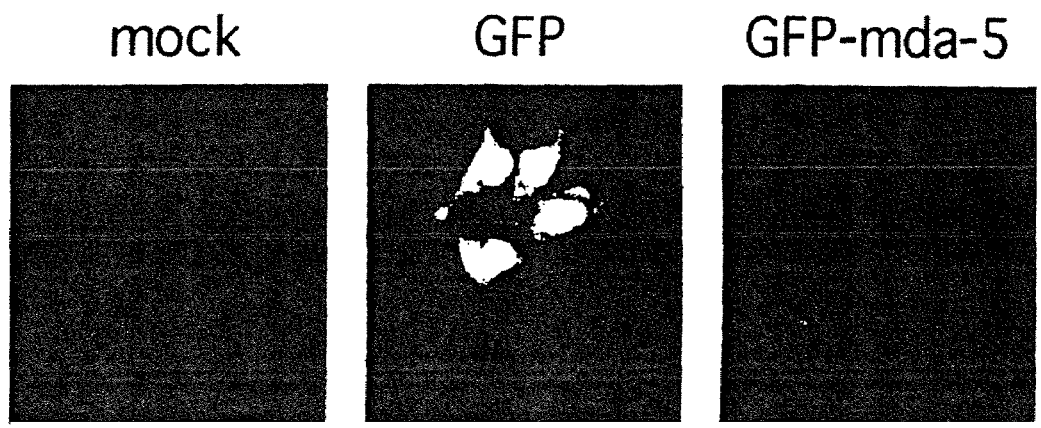

Expression of MDA-5 Protein and Intracellular Localization of MDA-5: To verify the authenticity of the mda-5 cDNA clone, in vitro translation experiments were performed. Expression of the mda-5 cDNA in an in vitro translation assay results in an encoded protein of ~120 kDa, close to the predicted size of the MDA-5 protein which is 116.7 kDa (FIG. 8A). The MDA-5 protein was tagged with either green fluorescent protein (GFP) or hemaglutinnin (HA) and transiently transfected into 293 cells. Western blot analyses of cell lysates specifically detected an ~120 kDa protein (HA-tagged) and an ~160 kDa protein (GFP-tagged) in mda-5 cDNA transfected cells. These findings indicate that the cloned mda-5 cDNA does encode a protein of the expected size for this gene. Confocal fluorescence microscopy of 293T cells transiently transfected with GFP-mda-5 fusion protein demonstrated that the protein localizes in the cytosol (FIG. 8C). A specific localization pattern within the cytoplasm of the GFP-mda-5 fusion protein was not observed. It is conceivable that the MDA-5 protein in the cytoplasm may play a role in the translation of specific mRNAs.

Figure 9:
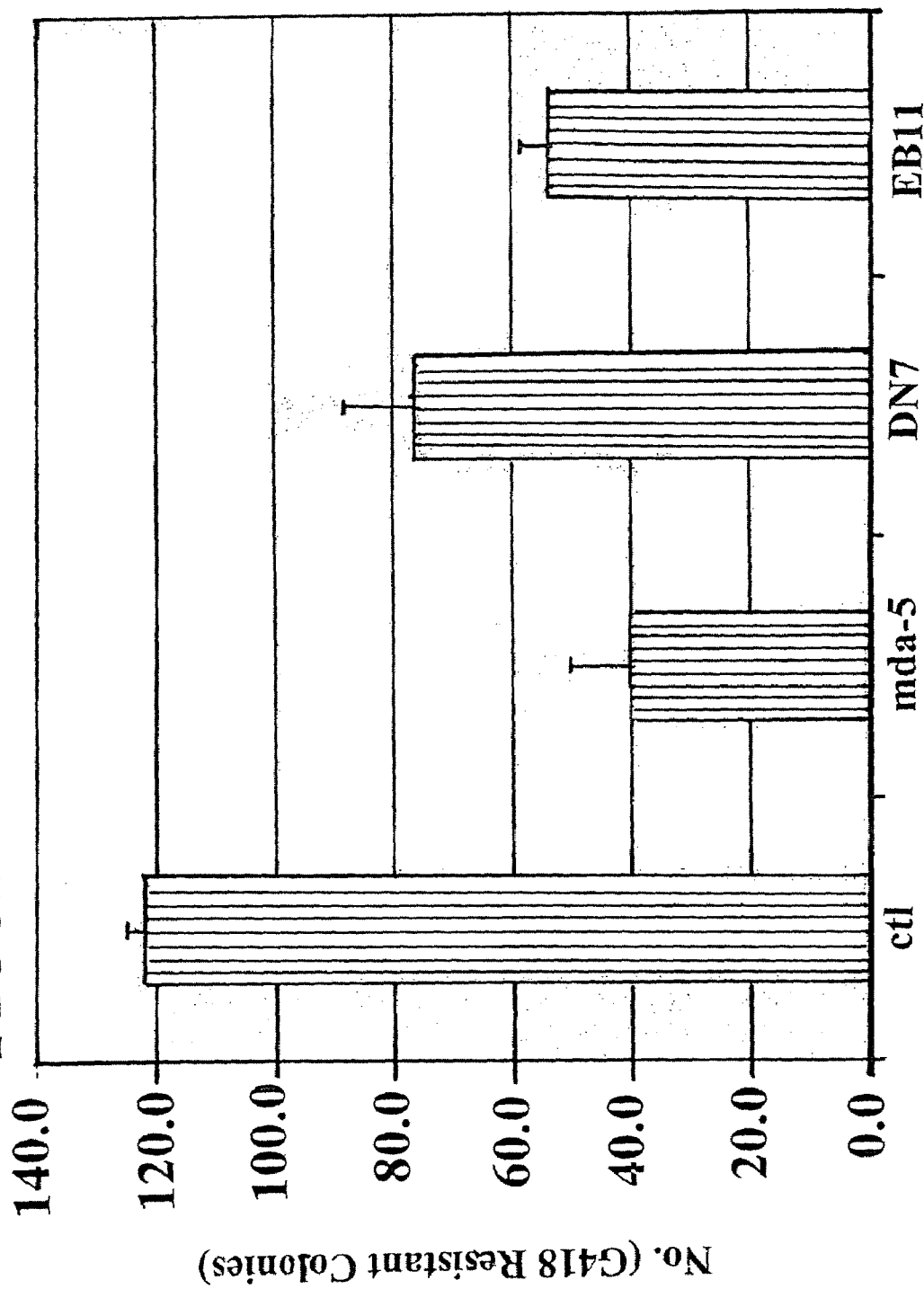
FIG. 9. The effect of ectopic expression of mda-5 on G418-resistant colony formation of HO-1 melanoma cells. HO-1 melanoma cells were transfected and selected with G418 as in Materials and Methods. Giemsa-stained colonies containing more than about 50 cells were counted. The results are mean ±standard error from three independent transfections (three plates for each transfection) with two different plasmid batches.

Effect of mda-5 on Colony Forming Ability of HO-1 Cells: HO-1 cells treated with IFN-β grow slower and display a noticeable enlargement in size in comparison with untreated cells. Since mda-5 is induced primarily by IFN-β, ectopic expression of mda-5 could mimic the effect IFN-β treatment and decrease proliferation. It is also conceivable that the CARD region of mda-5 could induce apoptotic signals and that ectopic expression of mda-5 could affect cell survival. To test for growth inhibitory or pro-apoptotic effects of mda-5 this gene was transfected and ectopically expressed in HO-1 cells and colony forming ability was determined (FIG. 9). Compared with parental vector transfected cells, the number of G418-resistant colonies in mda-5 expression-vector transfected cells was reduced by ~70%. A reduction in colony numbers that was less dramatic than the full coding frame of mda-5 versus parental vector transfected cells was also apparent when HO-1 cells were transfected with a deletion mutant of mda-5. Ectopic expression of the mda-5 deletion mutant (DN7, D310-484 including both ATPase motifs) caused a 47% reduction and transfection with a 2 kb antisense mda-5 (EB11) resulted in a 56% reduction in colony formation versus vector transfected controls. It appears that antisense mda-5 does not effectively block mda-5 expression. In fact, endogenous mda-5 expression was observed in cells transfected with antisense mda-5. It is possible that antisense mda-5 expression induces intracellular dsRNA formation and the dsRNA, in turn, induces endogenous mda-5 expression. In this way, ectopic expression of antisense mda-5 may affect colony-forming efficiency of HO-1 cells by directly altering the level of mda-5 in these cells. This is only one hypothetical explanation for this apparently paradoxical observation. Further studies are necessary to define the precise mechanism(s) by which ectopic expression of mda-5 exerts its effect on colony formatting ability of HO-1 cells.

Mda-5 Promoter Isolation and Characterization: Induction of mda-5 mRNA subsequent to treatment of human HO-1 melanoma cells with IFN-β indicated the strong likelihood of transcriptional regulation of gene expression based on Northern blot studies. To determine if the primary level of regulation was indeed transcriptional, a nuclear run-on experiment was performed (FIG. 7). Induction of mda-5 gene expression, as detected by a positive hybridization signal occurred in HO-1 samples that had been treated with IFN-β as opposed to a much lower signal in untreated cells, thereby validating the above hypothesis.

Having confirmed that induction of Mda-5 mRNA occurred primarily at the transcriptional level, it was decided that regulatory genomic DNA sequences involved in this process should be isolated and characterized. To achieve this goal, a human genomic DNA library constructed in a Bacterial Artificial Chromosome vector (BAC, Genome Systems Inc.) was screened using the mda-5 cDNA as a probe. Two rounds of screening were performed to obtain two overlapping clones that spanned the entire mda-5 genomic locus including several thousand bp of sequence upstream of the translational initiation codon. Mapping of the BAC clone containing the upstream region by restriction enzyme digestion, Southern blotting and sequence analysis permitted the identification of DNA fragments that contained potentially important regulatory sequences, which in the case of most protein coding genes lie upstream of the transcription initiation site. An approximately 7 kb HindIII fragment containing a partial first exon (including the initiator methionine) and approximately 6 kb of upstream sequence (FIG. 10) was subcloned into the HindIII site of the promoterless luciferase reporter vector, pGL3 (Promega). Transfection of this construct into HO-1 cells in the presence or absence of IFN-β did not result in the production of Luciferase enzyme as determined by luminometric quantitation assays, necessitating a re-examination of the cloned DNA sequence. Conceptual translation of the cloned sequence when initiated from the mda-5 translation initiation ATG site (FIG. 10) indicated that it would cause translational misreading and premature truncation of the Luciferase open reading frame with subsequent loss of enzymatic activity. To circumvent this problem, a small deletion of DNA sequences containing the mda-5 initiator methionine was carried out using a BstXI restriction digestion (FIG. 10) followed by blunt ending the incompatible end overhangs and recircularization of plasmid by ligation.

Figure 11A:
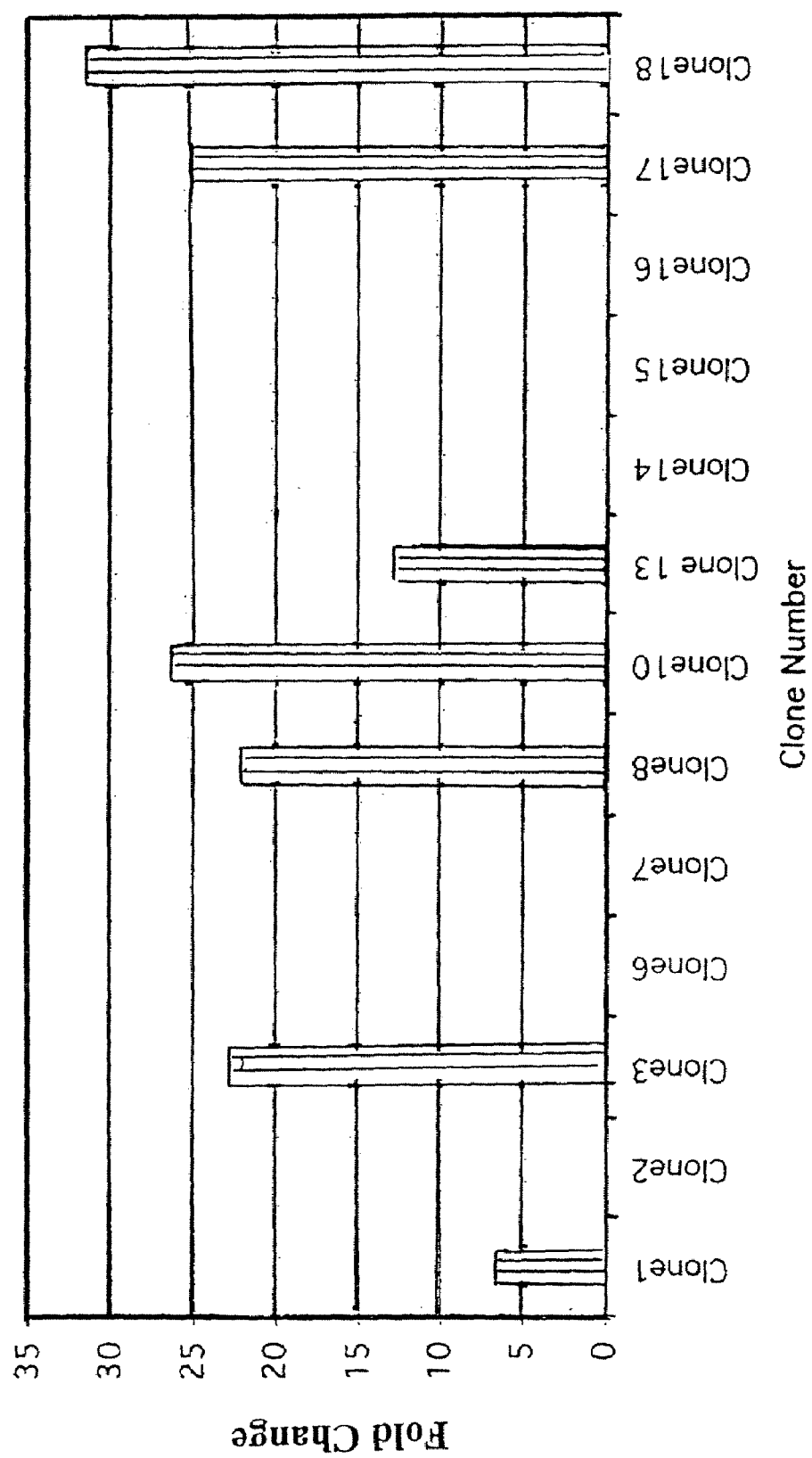
FIG. 11: Screening of stable human HO-1 melanoma clones for promoter activity of stably integrated mda-5 reporter construct. Transfected HO-1 cells were selected by Puromycin drug selection and individual colonies analyzed for induction of luciferase activity in the presence of IFN-β. Values are expressed as fold change against uninduced values of luciferase activity.
Figure 11B:
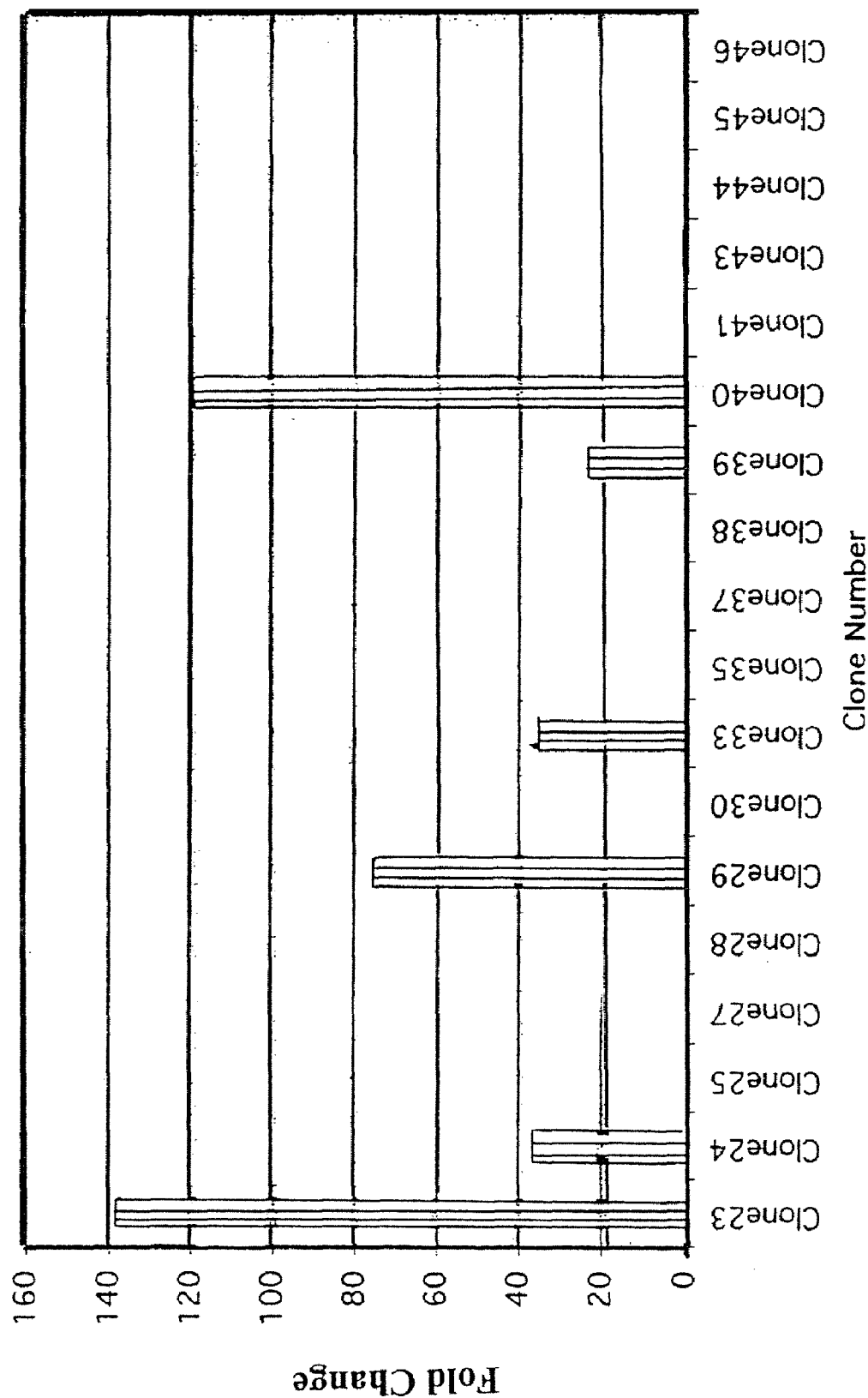
Figure 12A:
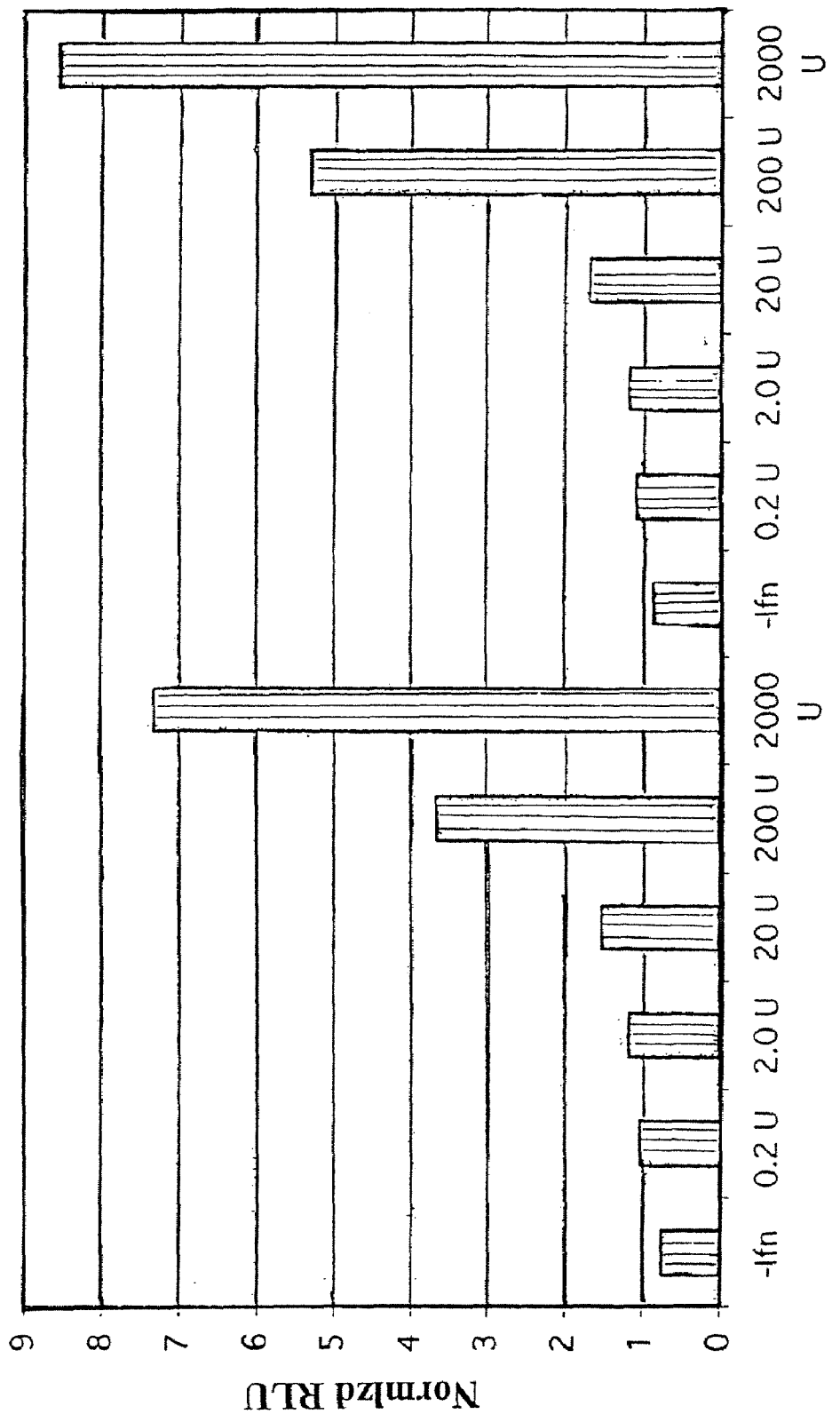
FIG. 12: Induction kinetics of mda-5 promoter activity. Stable clones #20 and #40 were treated with IFN-β and samples were harvested and analyzed for luciferase activity at the times indicated.
Figure 12B:
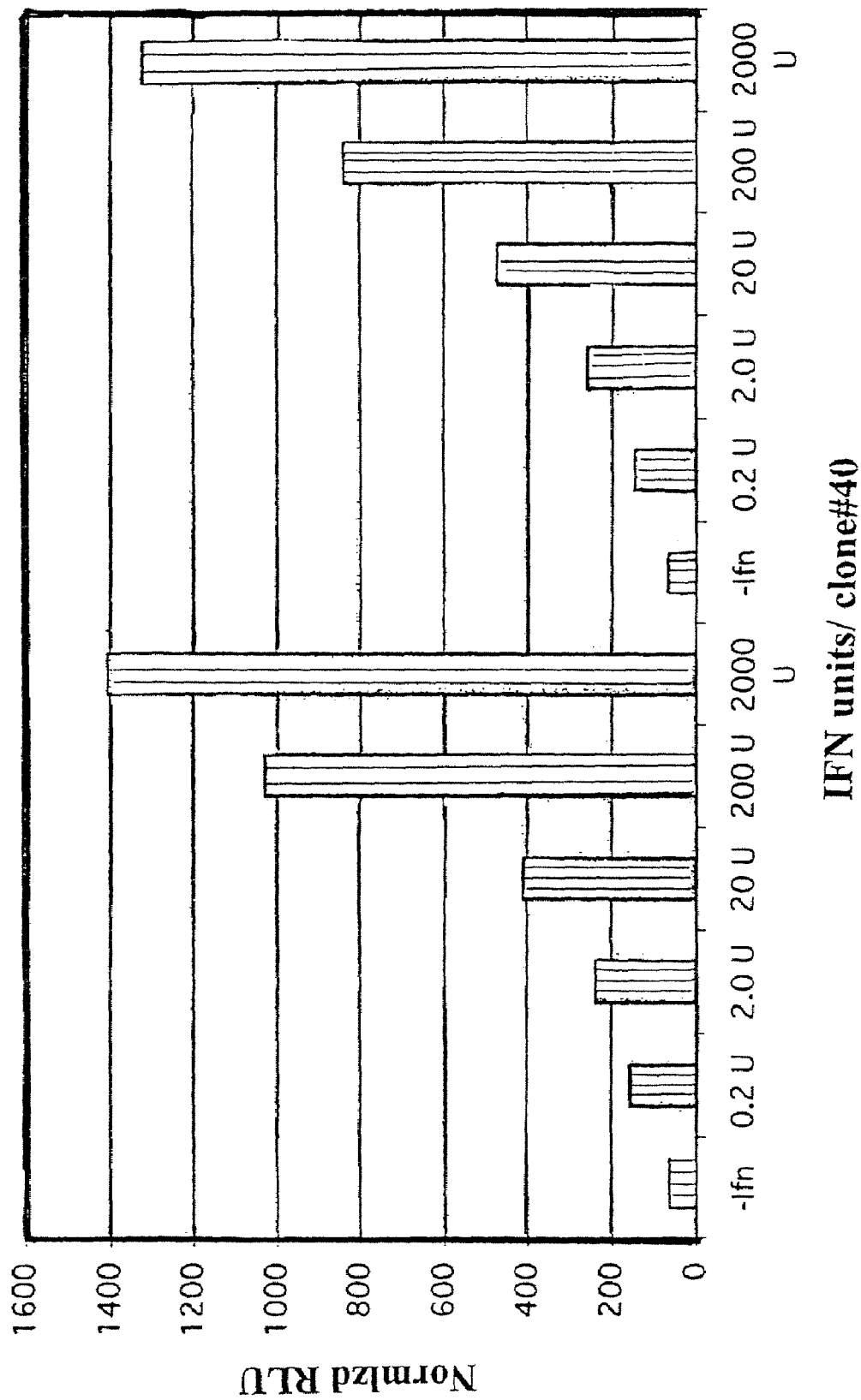
Figure 13A:
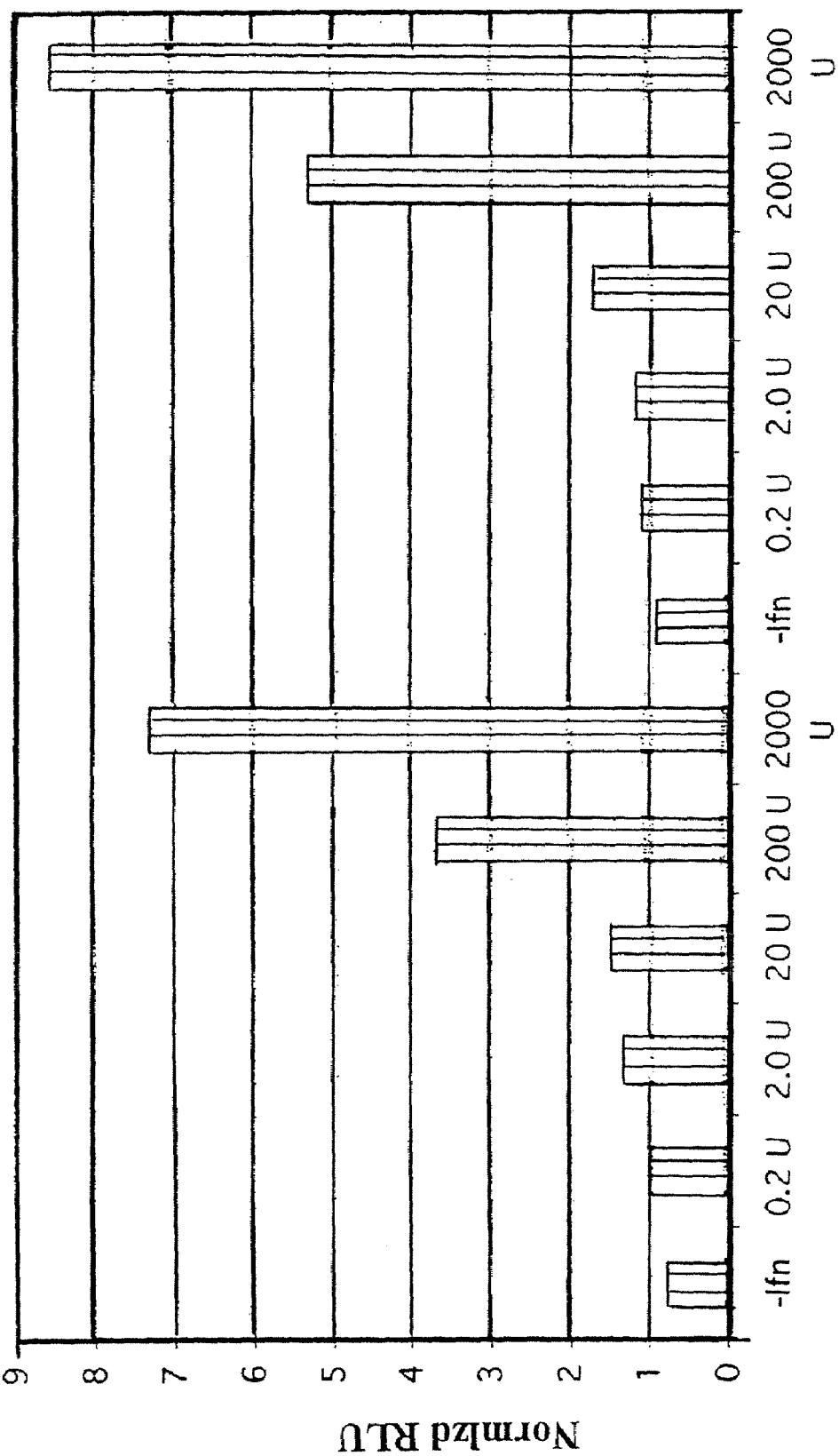
FIG. 13: Responsiveness of the mda-5 promoter to IFN-β levels: Stable clones #20 and #40 were treated with IFN-β and samples were harvested and analyzed for luciferase activity 48 h after initiation of treatment. The extent of activity was normalized based on equivalent protein content and performed in duplicate for each clone.
Figure 13B:
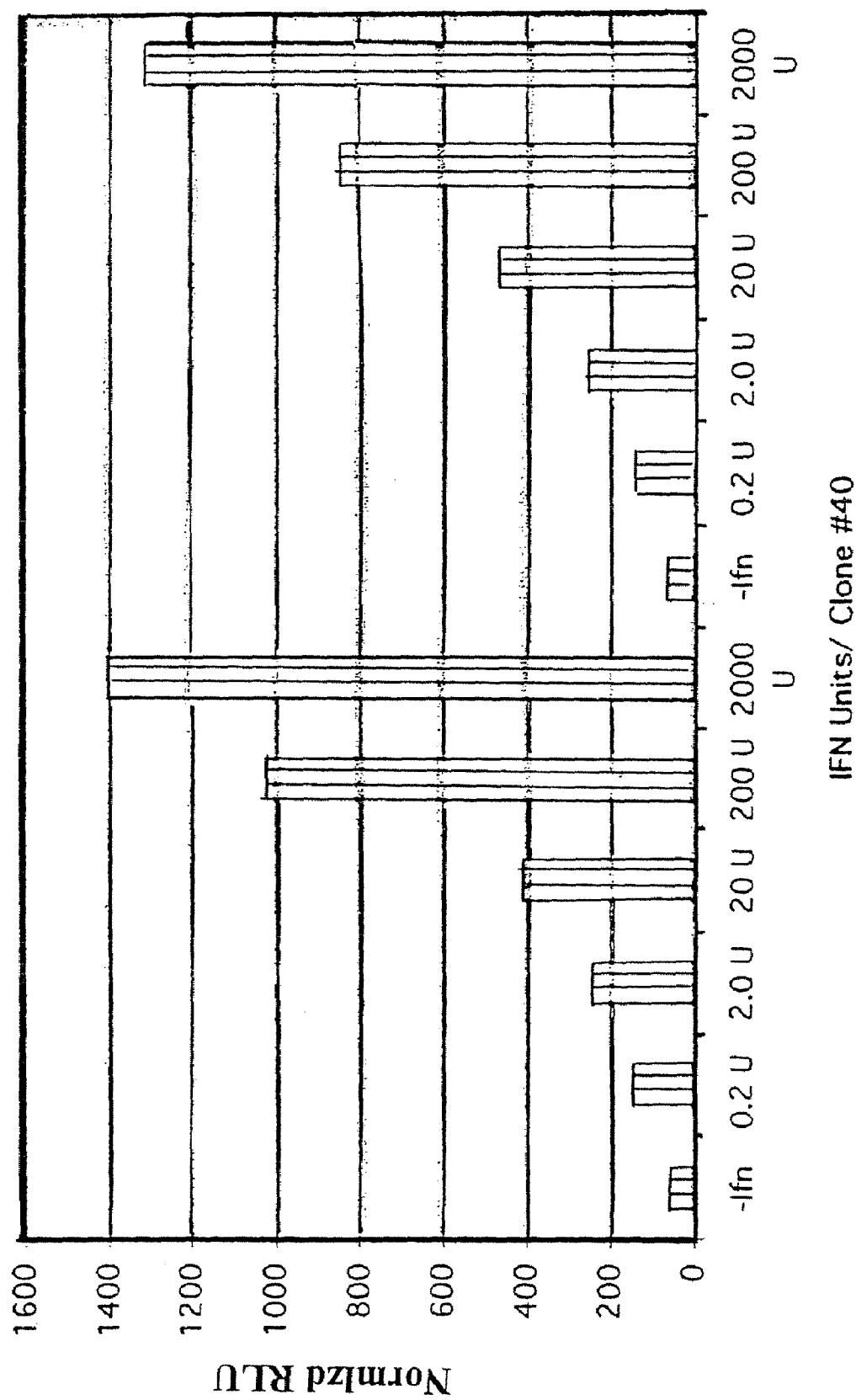
Figure 14A:
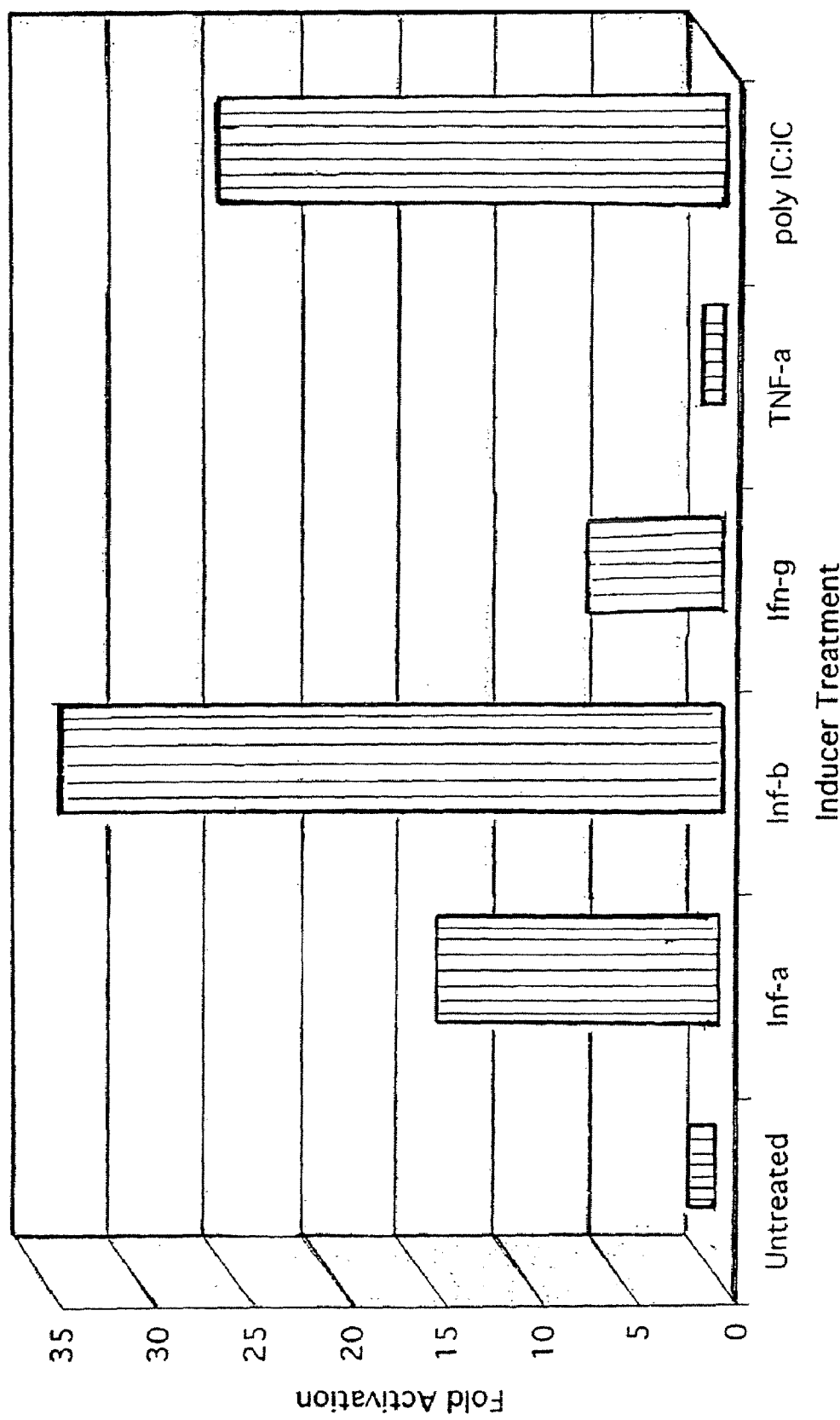
FIGS. 14A–14B: Responsiveness of the mda-5 promoter to various inducers.
Figure 14B:
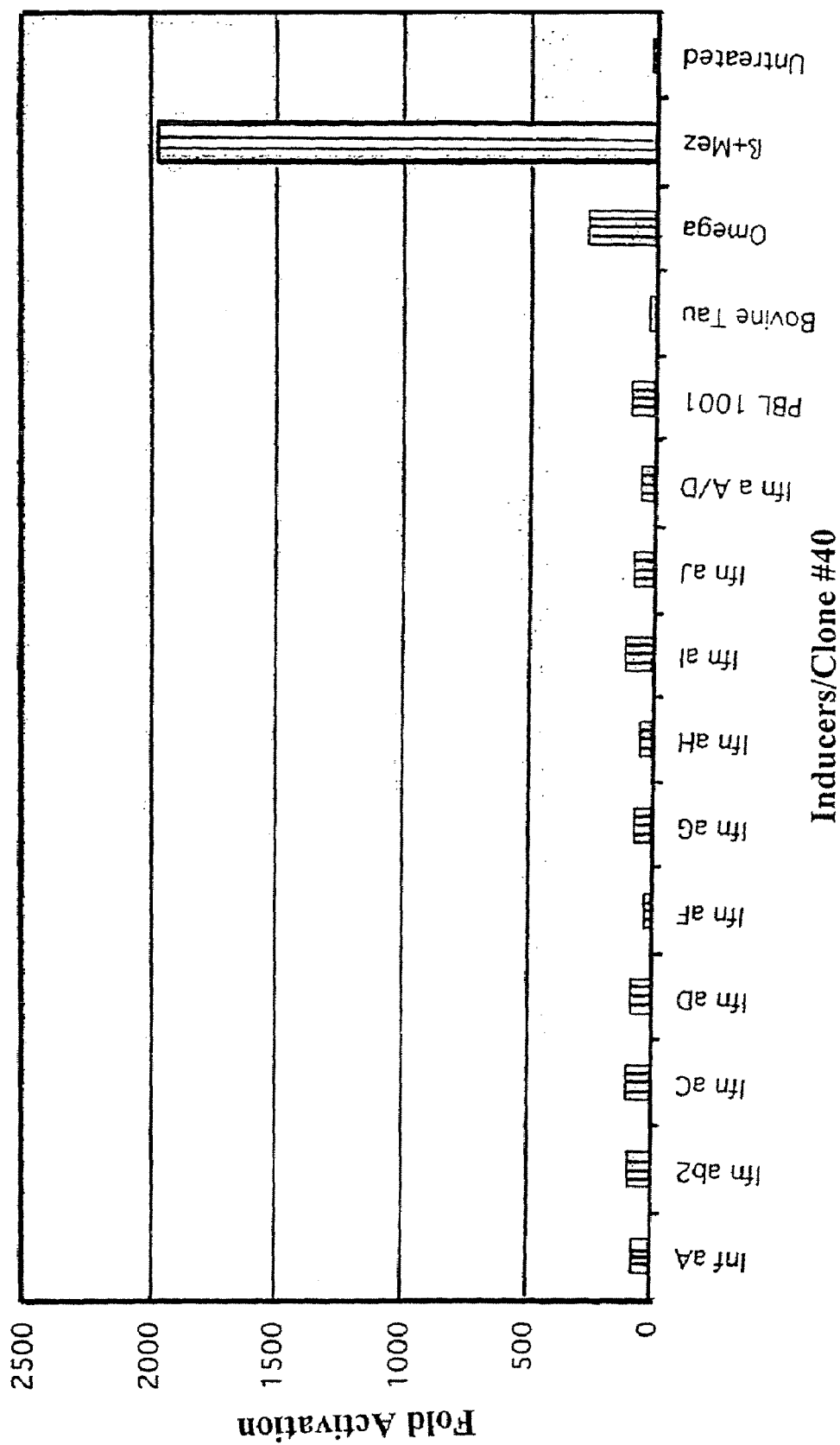
Figure 15A:
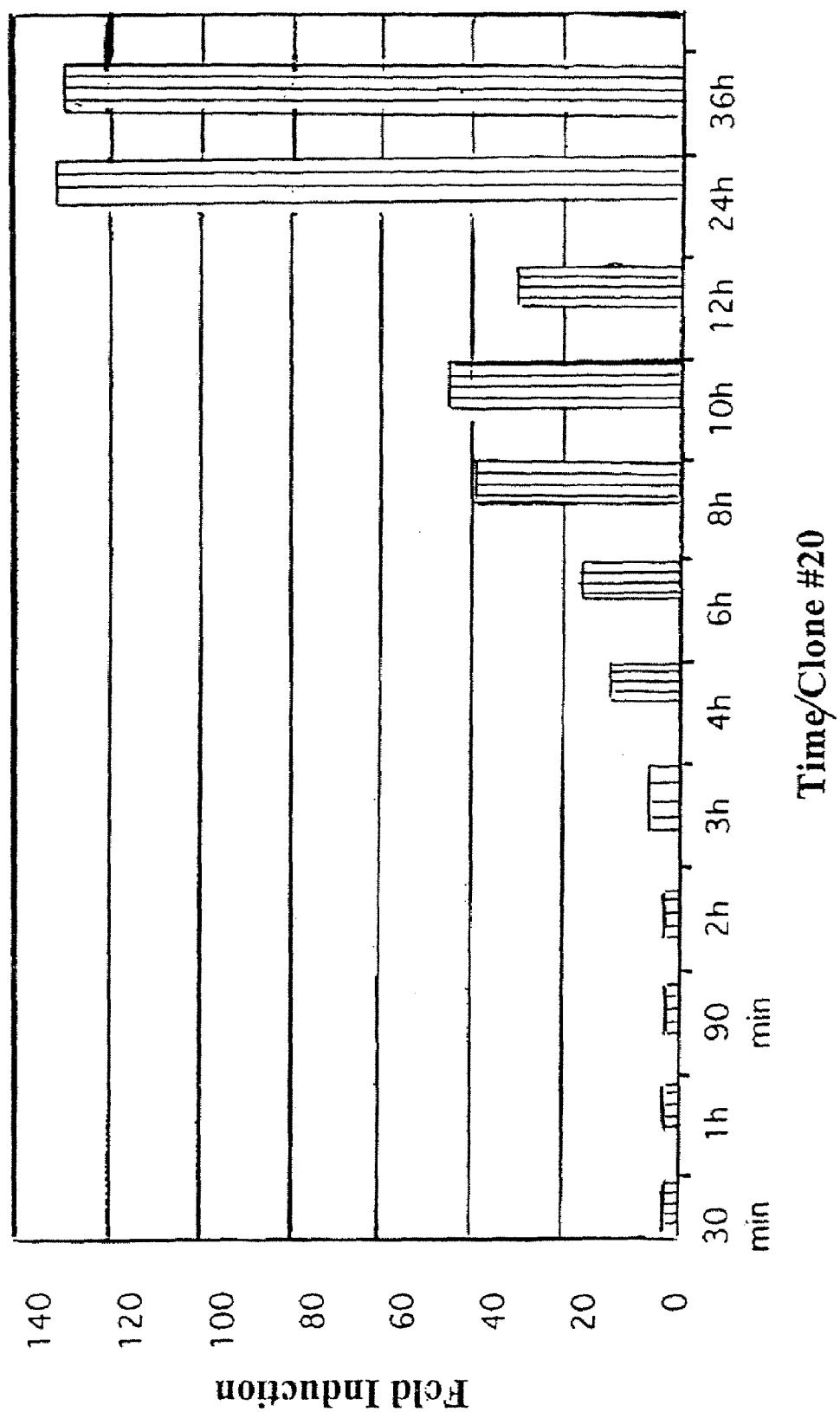
FIG. 15: Induction kinetics of mda-5 promoter activity by double stranded RNA. Stable clones #20 and #40 were treated with 2 µg/ml poly IC:IC and samples harvested and analyzed for luciferase activity at the times indicated.

The modified mda-5 reporter construct was transfected into parallel sets of HO-1 cells that were treated or not with IFN-β. Quantitation of luciferase activity indicated that this modified reporter containing a partially deleted Exon 1 and around 6 kb of upstream sequences, showed ~10 fold higher luciferase activity in cells that had been treated with IFN-β compared to untreated controls. This level of induction was comparable to that seen with the endogenous gene in Northern blot analyses. It therefore appeared that the cloned regulatory genomic DNA sequence in the reporter construct contained the elements required for the regulation of the mda-5 gene. It was however, necessary to confirm that the cloned sequences contained all the regulatory elements involved in the transcriptional control of the endogenous cellular gene. Since HO-1 melanoma cells show a very low and variable transfection efficiency it initially proved very difficult to determine the activity of the transiently transfected reporter in a consistent way for variables such as kinetics of induction, optimal concentration of inducer and the identification of other is potential activators. To circumvent this technical problem the mda-5 promoter construct was stably integrated into genomic DNA of HO-1 cells by co-transfection with a puromycin resistance plasmid and selection to isolate a clonal population of stable integrants. This selection procedure resulted in the production of several clones of which 48 were randomly picked for further analysis. Screening of these stable promoter clones by treatment with IFN-β indicated that an entire range from completely inactive to highly active, as measured by luciferase activity, had been obtained (FIG. 11). Some of the clonal isolates showed induction levels similar to the endogenous gene (around 10 fold), while others displayed much higher induction (around 100-fold). It is a likely possibility that the clones showing higher levels of induction contain multiple copies of integrated plasmid that due to an additive effect show higher levels of activity. Two individual clones (#20 and #40) were selected for further analyses to determine if activation kinetics and overall responsiveness to inducer, as a measure to ascertain the completeness of the isolated promoter sequence, mimicked that previously observed for the endogenous gene. In the initial screen (FIG. 11) the clone designated #20 showed a very low basal activity that on induction was >1000 fold. It was therefore not included in the plot to permit the scale to represent the other clones (ranging from 0–150 fold induction) accurately. This clone on subsequent analysis displayed a very low basal activity but a much lesser final fold activation (FIG. 12) than seen in the initial screen, but has maintained this property over several subsequent culture passages. To determine the induction kinetics of the promoter construct following treatment with IFN-β, a fixed number of cells (106/6 cm culture dish) was treated with inducer and assayed for luciferase activity compared with a parallel uninduced control sample, at various time-points following treatment (FIG. 12). Irrespective of the final fold-induction of luciferase levels, which varied in an individual clone, the overall pattern of induction kinetics was almost identical and similar to that of the endogenous gene as determined by Northern blotting. Similarly, assays were performed to determine the range of sensitivity of detection of exogenously added Interferon levels as determined by a luciferase read out (FIG. 13). The results of this assay closely paralleled that observed for the endogenous gene with measurable levels of 0.2 U of IFN-β being detectable. The promoter clone isolates were also used to determine responsiveness to different forms of IFNs including human IFN-α, β, and γ synthetic double stranded RNA (polyIC:IC; Amersham) and TNF-α (FIG. 14A) using transient transfection assays with the reporter construct, in HO-1 melanoma cells. In addition, Clone #40 stable HO-1 cells were treated with human IFN-αA, -αb2, -αC, αD, αF, -αG, αH, -αI, -αJ, -αA/D, PBL 1001, Bovine Tau, Ω and Human IFN-β (FIG. 14B). Differential levels of responsiveness were seen dependent on the type of compound used, in general the Mda-5 promoter construct was most responsive to INF-β relative to other IFNs, comparable to the results obtained in Northern analyses with the endogenous cellular gene. As seen above, Mda-5 gene induction also occurs upon treatment of cells with synthetic double stranded RNA (poly IC:IC). Studies identical to those described for IFN-β were performed using double stranded RNA as an inducer with the stable HO-1 promoter clones. These experiments generated results that were similar to endogenous gene induction for parameters including time and level of induction (FIG. 15).

Discussion

Genes displaying differential expression as a function of induction of terminal differentiation by treatment of HO-1 melanoma cells with IFN-β+MEZ are classified into four subgroups based on their induction pattern (Jiang and Fisher, 1993). Mda-5 represents a Type I mda gene, which is induced by IFN-β and IFN-β+MEZ. Treatment with MEZ alone, which is a protein kinase C activator and a weak second-stage tumor promoter, does not induce mda-5 expression, but it potentiates mda-5 expression at a transcriptional level when combined with IFN-β. The inducible expression of 2'-5'oligoadenylate synthetase, another IFN-responsive gene, by IFN-α is augmented by TPA. Numerous evidence based on the use of PKC inhibitors indicate that the potentiation of IFN-gene expression by TPA involved activation of PKC, but the exact mechanism of this induction remains to be determined.

HO-1 melanoma cells treated with IFN-β increase in size, display slower growth kinetics and exhibit enhanced melanogenesis, but they do not undergo obvious morphological changes or cell death (Fisher et al., 1985). In contrast, MEZ, which does not induce mda-5, induces profound changes in the morphology of HO-1 cells, including the production of dendrite-like processes. Reagents that induce specific components of melanocytic differentiation in human melanoma cells, including all trans retinoic acid (RA), mycophenolic acid (MPA), cyclic-AMP (cAMP), dimethyl sulfoxide (DMSO) and TPA, also fail to significantly induce mda-5 expression. Therefore, it is possible that the primary role of mda-5 in the induction of terminal cell differentiation of HO-1 cells by IFN-β+MEZ is restricted to IFN-β-mediated suppression of cell proliferation.

Although IFN-α and IFN-γ significantly induce mda-5 expression, IFN-β was >5-fold more effective in inducing mda-5 expression than either IFN-α or IFN-γ. IFN-β enhanced the expression of mda-5 in normal and tumor cell lines, including various melanoma cell lines regardless of their p53 or Rb status. Although mda-5 was undetectable in Northern blot of whole brain Poly A+ mRNA, mda-5 was detected and further induced by IFN-β treatment in cultured normal cerebellum and glioblastoma multiforme cells. In these contexts, mda-5 can be classified as an IFN-β-inducible gene. Both IFN-β and IFN-α share a common receptor (IFN-R1) and often display a similar pattern of gene expression changes, but the biological effects of these agents can be distinct. Mda-5 and a gene named INF-R1 are unique in that they display increased responsiveness to IFN-β than to IFN-α, which may involve IFN-α-specific cellular processes.

In addition to IFNs, the expression of mda-5 is also induced in both HO-1 melanoma and human skin fibroblast cells by TNF-α and poly IC. Both TNF-α and poly IC are established inducers of IFN-β gene expression. Based on these facts it is possible that TNF-α and poly IC may induce mda-5 gene expression by modulating IFN-β gene expression. In contrast, pretreatment with cycloheximide (CHX), a protein synthesis inhibitor did not inhibit mda-5 expression induced by TNF-α or poly IC, which suggests that these agents are direct inducers of mda-5. Poly IC directly activates PKR (dsRNA activated interferon-inducible protein kinase) and induces class I MHC expression. TNF-α signaling was also found to be dependent on PKR activation. Alternatively or additionally, PKR which, independent of IFN receptor signaling, phosphorylates IkB and transactivates NFkB could be the mediator of TNF-α and poly IC-induced mda-5 expression. However, it is still possible that TNF-α and poly IC could stimulate secretion of preexisting IFN-β without the requirement of new protein synthesis.

IFNs were initially identified as molecules that provide immediate protection against viral infection by eliciting an antiviral state in treated cells. IFN treatment evokes diverse responses depending on the target cell which include growth inhibition, changes in differentiation, induction or inhibition of apoptosis and changes in the expression of immune system modulating genes. IFN-β displays more potent growth inhibitory effects on normal melanocytes and melanoma cells, including HO-1, than IFN-α and IFN-γ. Interestingly, the growth inhibitory effect of IFNs in these cells correlates well with the level of induction of mda-5 expression. In addition, both inducers of mda-5, TNF-α and poly IC inhibit cell proliferation and induce apoptosis in a cell type specific manner. Induction of mda-5 by IFN-β is an early event, since the steady state mRNA message levels begin increasing within two hr of treatment. These results suggests that mda-5 may play a pivotal role in IFN-β-mediated suppression of cell proliferation.

Ectopic expression of mda-5 reduces the colony-forming capacity of HO-1 melanoma cells by ~70%. Considering the inefficient nature of transfection and the random incorporation of transfected genes into the cellular genome, the effect of ectopic mda-5 expression on colony-forming efficiency is quite dramatic. Surprisingly, the expression of a deletion mutant of mda-5 (deletion of the ATPase motif) also reduced colony formation (~47%), but was markedly less potent than the wild type mda-5 gene. Colony-forming efficiency is regulated by multiple parameters including inherent plating efficiency, and the growth inhibitory or toxic effect of the transfected gene product. Further studies are required to determine which factor is most critical in reducing the colony-forming efficiency of cells ectopically expressing mda-5.

Profile scans of the MDA-5 protein reveal putative CARD and RNA helicase motifs. Multiple sequence alignments of the CARD motif in MDA-5 using the ClustalW system indicate that this region most closely resembles the CARD of RAIDD, which is a component of TNF-R1-mediated apoptotic signaling pathway and which contains both a death domain and a CARD motif. RAIDD interacts with RIP through its death domain and with ICH-1 (caspase-2) probably via its CARD motif. Although not as effective as IFN-β, TNF-α also induces mda-5 expression in HO-1 melanoma cells. In is therefore conceivable that mda-5 may interact with RAIDD and serve as a death effector molecule like ICH-1. A pro-apoptotic role of mda-5 is also supported by the dsRNA-dependent induction of this gene, which also activates PKR, a recognized molecule involved in growth suppression and apoptosis. However, a direct apoptotic role of mda-5 does not coincide with the effect of IFN-β on HO-1 melanoma cells, which results in growth suppression and not cell death. It is feasible that mda-5 may be a component of a death effector molecule, but by itself it lacks the capacity to trigger apoptosis. In this context, ectopic expression of mda-5 may result in growth inhibition and not apoptosis. It is also possible that the level of ectopic expression of mda-5 may determine whether this molecule is growth inhibitory or toxic. If this is true, expression of mda-5 by means of a adenovirus under the control of a strong promoter may produce sufficiently high levels of MDA-5 to induce cell death as opposed to growth inhibition.

Another distinct motif present in the MDA-5 protein is a RNA helicase signature domain, which spans the C-terminal half of this molecule. RNA helicase is a family of enzymes with a helicase motif, which potentially catalyzes NTP-dependent dsRNA unwinding activity. Not only are the core residues among the RNA helicases conserved, but also the spaces between these residues are retained in the different RNA helicases. Three main features characterize RNA helicases from the N- to C-terminal, an ATPase A motif (GXXGXGKT), an ATPase B motif (DEAD; SEQ ID NO:20, DEAH; SEQ ID NO:21 or DEXH; SEQ ID NO:22) and a critical domain for RNA interaction (HRIGRXXR; SEQ ID NO:23). RNA helicases are classified into three subgroups based on their ATPase B motifs. RNA helicases are implicated in the majority of steps associated with RNA processing and transcription, nuclear and mitochondrial RNA splicing, RNA editing, ribosomal biogenesis, nuclear cytosolic RNA export, degradation of nonsense RNA and RNA translation. Hence, RNA helicases affect many biological phenomena including cell differentiation, proliferation, development and viral life cycle. Although the RNA helicases are classified into three subgroups, the biological relevance of these groups remains to be defined. In addition, the enzymatic activity of many putative RNA helicases has not been confirmed, this could partly be because of the absence of the appropriate substrate and standard protocol due to the diversity of these enzymes.

Despite the well-conserved attributes of RNA helicases, MDA-5 contains four unique features that could mediate functional divergence. The CARD domain of MDA-5 in its N-terminal region is not found in any previously identified helicases, although the functional significance of this region is currently under investigation. The ATPase A motif of mda-5 is unique and contains LPTGSGKT as opposed to the sequences found in other RNA helicases (GXXGXGKT) and a mutation of the first glycine residue of murine eIF-4A to valine abolishes ATP binding ability. Since leucine is a non-polar amino acid as is valine, but it has a bulkier side chain than valine, MDA-5 may not bind ATP effectively and, hence, may be an ATPase defective helicase or it may require a different energy source and/or metals for activity. This property of MDA-5 may explain the reduction in colony forming efficiency by a expression of a mutant of mda-5 lacking this region of the MDA-5 protein. The HRIGRXXR motif which is critical for RNA binding in vitro is not well conserved in MDA-5 (ARGRI; SEQ ID NO:24). The functional role of such sequence divergence in the MDA-5 protein remains to be determined. Three yeast hypothetical ORFs share specific features of MDA-5 including ATPase and RNA binding sites, but their biological function has not been ascertained. Complementation assays between these proteins can provide insights on functional and evolutionary relationship among these molecules.

Taken together, the distinctive features of the MDA-5 protein suggest that this molecule represents a member of a new family of RNA helicases. If this is the case, mda-5 may participate in degradation, translation or inhibition of translation of pro- or anti-apoptotic RNA molecules through its RNA helicase domain. Alternatively, mda-5 might be a signal transducer between IFN signals and the apoptotic machinery to prepare the cell for viral invasion and dsRNA accumulation. Localization of GFP-mda-5 fusion protein in the cytoplasm is not contradictory to this hypothesis.

The reporter isolate comprising the mda-5 promoter sequences driving the luciferase cDNA, based on comparison of the quantitation of luciferase assays to fold induction seen in Northern blot analyses of RNA from treated cells, closely mimicked the induction behavior of the endogenous gene. Activation of gene expression occurred primarily with IFN-β and double stranded RNA and to a lesser extent with other IFNs. This DNA sequence is therefore of considerable utility in understanding the regulation of mda-5 in particular and IFN-β inducible genes in general, also encompassing but not restricted to the analysis of compounds including synthetic small molecules that affect this pathway.

Due to the high level of sensitivity, technical simplicity and amenability toward semi-automation of luciferase assays, the mda-5 promoter clone isolates in HO-1 melanoma cells comprise an additional very useful detection and assay system for IFN levels with potentially significant advantages in terms of cost, convenience and reproducibility. Moreover due to the presence of the reporter construct within an in vivo biological context, in addition to the ability to quantitate the amount of exogenously added IFNs or determine responsiveness to specific IFNS, the system is utilizable in the study of compounds of a diverse nature that potentially impinge on the pathway with respect to multiple biological and pharmacological aspects. These include agonistic or antagonistic effects of a specific compound on the IFN pathway combined with the general biological toxicity of that or a combination of compounds, potentially within the same assay itself. The promoter sequence may also be introduced into appropriate cells with an IFN relevant responsiveness similar to that achieved for HO-1 and studied parallel to those described in the HO-1 human melanoma system be performed.

In summary, mda-5 is a new IFN-β inducible putative RNA helicase containing a CARD motif. The expression of mda-5 is also induced by growth inhibitory and apoptotic signal molecules such as TNF-_and poly IC. Although it was not demonstrated in the present experiments, the ability of IFN-β and poly IC to induce mda-5 expression support the potential for viral induction of this gene. Ectopic expression of mda-5 significantly reduces colony-forming efficiency of HO-1 melanoma cells as expected from the inductive nature and sequence of this gene. The enzymatic activity of MDA-5 remains to be determined. As mentioned earlier, mda-5 may be a defective RNA helicase and a naturally occurring inhibitor of additional unknown helicases. If this is the case, it will be important to identify counterparts of mda-5 which display antiviral, proliferation inhibitory and/or apoptotic roles in cellular physiology. Of particular note is that viruses like hepatitis C virus (HCV) contain a helicase in their genome. Defining the enzymatic activity of MDA-5 may be achieved by modulating the experimental conditions, i.e., by changing reaction conditions including NTP and metal requirements, using potential stimulators like 2'–5' oligoadenylate, etc. Investigation of the physiological role and molecular basis of mda-5 action should provide important insights into the mechanism of cellular defense conferred by IFN against viral attack. This information should prove valuable in developing new strategies for inhibiting viral pathogenicity and for designing more effective antiviral therapeutics.

Example 2

Reporter Cell Lines

Reporter cell lines derived from the HO-1 human melanoma cell line containing genomically integrated copies of the Melanoma Differentiation Associated Gene-5 (Mda-5) upstream promoter sequences.

A Bacterial Artificial Chromosome (BAC), human genomic library was screened to isolate sequences containing the Mda-5 gene. Two BAC clones containing the coding and upstream sequences of the gene were isolated and characterized.

The complete intron/exon structure of the coding sequences has been determined. An approximately 6 kb fragment upstream of the transcription start site was also isolated. This fragment was cloned into a promoterless luciferase vector (pGL3 Basic, Promega) and assayed by transient transfection assays for transcriptional activity. The activity displayed by this promoter construct was identical to that of the endogenous gene in terms of responsiveness to inducers (recombinant human β-interferon or synthetic double stranded RNA, poly IC) and time kinetics of induction.

Several sublines containing stably integrated copies of the transcriptionally active luciferase plasmid in a HO-1 human melanoma background was constructed. Independent clonally isolated colonies were expanded and assayed for luciferase activity in the presence of recombinant human β-interferon or synthetic double stranded RNA, poly IC. These clones exhibited luciferase activity similar to the endogenous gene except that the level of induction varied from 10 to 100 fold, probably dependent on the number of integrated copies for each clone (the endogenous gene is induced about 10 fold). While these clones are most responsive to recombinant human β-interferon or synthetic double stranded RNA, poly IC they are also induced at lower levels by other interferons.

These cell lines may be used for:

A. Quantitation of biologically active amounts of interferon produced by various procedures;

B. In rapid high throughput screens to determine or distinguish the relative efficacy of compounds agonistic or antagonistic to the interferon biochemical and signalling pathway;

C. In a rapid high throughput screen to detect small molecules of potential pharmacological and therapeutic utility that synergizes or boosts cellular interferon pathways.

REFERENCES

1. Fisher, P. B. and S. Grant, Effects of interferon on differentiation of normal and tumor cells. Pharmacology & Therapeutics, 1985. 27(2): p. 143–66.
2. Waxman, S., ed. Differentiation Therapy (Ares Serono Symposia Publications, Rome). Vol. 10. 1995. 1–531.
3. Jiang, H., J. Lin, and P. B. Fisher, A Molecular Definition of Terminal Differentiation in Human Melanoma Cells. Molecular Cellular Differentiation, 1994. 2(3): p. 221–239.
4. Waxman, S., G. B. Rossi, and T. F., The Status of Differentiation Therapy of Cancer, in The Status of Differentiation Therapy of Cancer, S. Waxman, G. B. Rossi, and T. F., Editors. 1988, Raven Press: New York, N.Y. P. 1–422.
5. Fisher, P. B., et al., Effects of combined treatment with interferon and mezerein on melanogenesis and growth in human melanoma cells. Journal of Interferon Research, 1985. 5(1): p. 11–22.
6. Jiang, H., et al., Gene Expression Changes Associated with Reversible Growth Suppression and the Induction of Terminal Differentiation in Human Melanoma Cells. Molecular Cellular Differentiation, 1993. 1(1): p. 41–66.
7. Jiang, H., S. Waxman, and P. B. Fisher, Regulatin of c-fos, c-jun and jun-B Gene Expression in Human Melanoma Cells Induced to Terminally Differentiate. Molecular cellular Differentiation, 1993. 1(2): p. 197–214.
8. Jiang, H. and P. B. Fisher, Use a Sensitive and Efficient Subtraction Hybridization Protocol for the Identification of Genes Differentially Regulated during the Induction of Differentiation, in Human Melanoma Cells. Molecular Cellular Differentiation, 1993. 1(3): p. 285–299.
9. Jiang, H., et al., Subtraction hybridization identifies a novel melanoma differentiation associated gene, mda-7, modulated during human melanoma differentiation, growth and progression. Oncogene, 1995. 11(12): p. 2477–86.
10. Jiang, H., et al., The melanoma differentiation-associated gene mda-6, which encodes the cyclin-dependent kinase inhibitor p21, is differentially expressed during growth, differentiation and progression in human melanoma cells. Oncogene, 1995. 10(9): p. 1855–64.
11. Jiang, H., et al., The melanoma differentiation associated gene mda-7 suppresses cancer cell growth. Proceedings of the National Academy of Sciences of the United States of America, 1996. 93(17): p. 9160–5.
12. Lin, J. J., H. Jiang, and P. B. Fisher, Melanoma differentiation associated gene-9, mda-9, is a human gamma interferon responsive gene. Gene, 1998. 207(2): P. 105–10.
13. Huang, F., et al., Differentiation induction subtraction hybridization (DISH): a strategy for cloning genes displaying differential expression during growth arrest and terminal differentiation. Gene, 1999. 236(1): p. 125–31.
14. Huang, F., et al., Identification and temporal expression pattern of genes modulated during irreversible growth arrest and terminal differentiation in human melanoma cells. Oncogene, 1999. 18(23): p. 3546–52.
15. Jiang, H., et al., The Melanoma Differentiation Associated Gene-6 (mda-6), Which Encodes the Cyclin-Dependent Kinase Inhibitor p21, May Function as a Negative Regulator of Human Melanoma Growth and Progression. Molecular Cellular Differentiation, 1996. 4(1): p. 67–89.
16. Kang, D.-C. And P. B. Fisher, C-ORF, A simple and Efficient Way to Clone Full Open Reading Frame. (Manuscript in preparation). 2000.
17. Su, Z.-z., Y. Shi, and P. B. Fisher, Subtraction hybridization identifies a transformation progression-associated gene PEG-3 with sequence homology to a growth arrest and DNA damage-inducible gene. Proc. Natl. Acad. Sci. USA, 1997. 94: p. 9125–30.
18. Sambrook, J., E. Fritsch, and T. Maniatis, Molecular Cloning. 2 ed. 1989, New York, N.Y.: Cold Spring Harbor Laboratory Press.
19. Hofmann, K., P. Bucher, and J. Tschopp, The CARD domain: a new apoptotic signalling motif. Trends Biochem Sci, 1997. 22(5): p. 155–6.
20. Luking, A., U. Stahl, and U. Schmidt, The protein family of RNA Helicases. Crit Rev Biochem Mol Biol, 1998. 33(4): p. 259–96.
21. Rani, M. R. S., et al., Characterization of beta-R1, a gene that is selectively induced by interferon beta (IFN-beta) compared with IFN-alpha. J Biol Chem, 1996. 271(37): p. 22878–84.

What is claimed is:

1. An isolated nucleic acid comprising the sequence shown in SEQ ID NO:1 encoding a Melanoma Differentiation Associated Gene-5 (Mda-5) polypeptide.

2. An isolated nucleic acid comprising a cDNA sequence encoding an Mda-5 polypeptide having the sequence of SEQ ID NO:2.

3. An isolated nucleic acid molecule having at least 90% homology with SEQ ID NO:1.

4. A vector comprising the nucleic acid of claim 1, 2 or 3.

5. An isolated host cell comprising the vector of claim 4.

6. The host cell of claim 5, wherein the host cell is stably transformed with the vector of claim 4.

7. The host cell of claim 5, wherein the host cell is a tumor cell.

8. The host cell of claim 5, wherein the host cell is a melanocyte.

9. The host cell of claim 5, wherein the cell is an immortalized cell.

10. The host cell of claim 7, wherein the tumor cell is selected from the group consisting of a melanoma cell, a neuroblastoma cell, an astrocytoma cell, a glioblastoma multiforme cell, a cervical cancer cell, a breast cancer cell, a lung cancer cell and a prostate cancer cell.

* * * * *

UNITED STATES PATENT AND TRADEMARK OFFICE
CERTIFICATE OF CORRECTION

PATENT NO. : 7,229,822 B1 Page 1 of 1
APPLICATION NO. : 09/515363
DATED : June 12, 2007
INVENTOR(S) : Fisher et al.

It is certified that error appears in the above-identified patent and that said Letters Patent is hereby corrected as shown below:

ON THE COVER PAGE, item [73], insert

--"The Trustees Of Columbia University In The City Of New York,

New York, NY (US)"--

Signed and Sealed this

Twenty-ninth Day of April, 2008

JON W. DUDAS
*Director of the United States Patent and Trademark Office*

SEQUENCE LISTING

<160> NUMBER OF SEQ IDS NOS: 25

<210> SEQ ID NO 1
<211> LENGTH: 3365
<212> TYPE: DNA
<213> ORGANISM: homo sapiens

<400> SEQUENCE: 1

| | | | | | |
|---|---|---|---|---|---|
| gcgcgccggc | ctgagagccc | tgtggacaac | ctcgtcattg | tcaggcacag | agcggtagac | 60 |
| cctgcttctc | taagtgggca | gcggacagcg | gcacgcacat | ttcacctgtc | ccgcagacaa | 120 |
| cagcaccatc | tgcttgggag | aaccctctcc | cttctctgag | aaagaaagat | gtcgaatggg | 180 |
| tattccacag | acgagaattt | ccgctatctc | atctcgtgct | tcagggccag | ggtgaaaatg | 240 |
| tacatccagg | tggagcctgt | gctggactac | ctgacctttc | tgcctgcaga | ggtgaaggag | 300 |
| cagattcaga | ggacagtcgc | cacctccggg | aacatgcagg | cagttgaact | gctgctgagc | 360 |
| accttggaga | agggagtctg | gcaccttggt | tggactcggg | aattcgtgga | ggccctccgg | 420 |
| agaaccggca | gccctctggc | cgcccgctac | atgaaccctg | agctcacgga | cttgccctct | 480 |
| ccatcgtttg | agaacgctca | tgatgaatat | ctccaactgc | tgaacctcct | tcagcccact | 540 |
| ctggtggaca | agcttctagt | tagagacgtc | ttggataagt | gcatggagga | ggaactgttg | 600 |
| acaattgaag | acagaaaccg | gattgctgct | gcagaaaaca | atggaaatga | atcaggtgta | 660 |
| agagagctac | taaaaaggat | tgtgcagaaa | gaaaactggt | tctctgcatt | tctgaatgtt | 720 |
| cttcgtcaaa | caggaaacaa | tgaacttgtc | caagagttaa | caggctctga | ttgctcagaa | 780 |
| agcaatgcag | agattgagaa | tttatcacaa | gttgatggtc | ctcaagtgga | agagcaactt | 840 |
| cttttcaacca | cagttcagcc | aaatctggag | aaggaggtct | ggggcatgga | gaataactca | 900 |
| tcagaatcat | cttttgcaga | ttcttctgta | gtttcagaat | cagacacaag | tttggcagaa | 960 |
| ggaagtgtca | gctgcttaga | tgaaagtctt | ggacataaca | gcaacatggg | cagtgattca | 1020 |
| ggcaccatgg | gaagtgattc | agatgaagag | aatgtggcag | caagagcatc | cccggagcca | 1080 |
| gaactccagc | tcaggcctta | ccaaatggaa | gttgcccagc | cagccttgga | agggaagaat | 1140 |
| atcatcatct | gcctccctac | agggagtgga | aaaaccagag | tggctgttta | cattgccaag | 1200 |
| gatcacttag | acaagaagaa | aaaagcatct | gagcctggaa | aagttatagt | tcttgtcaat | 1260 |
| aaggtactgc | tagttgaaca | gctcttccgc | aaggagttcc | aaccatttt | gaagaaatgg | 1320 |
| tatcgtgtta | ttggattaag | tggtgatacc | caactgaaaa | tatcatttcc | agaagttgtc | 1380 |
| aagtcctgtg | atattattat | cagtacagct | caaatccttg | aaaactccct | cttaaacttg | 1440 |
| gaaaatggag | aagatgctgg | tgttcaattg | tcagactttt | ccctcattat | cattgatgaa | 1500 |
| tgtcatcaca | ccaacaaaga | agcagtgtat | aataacatca | tgaggcatta | tttgatgcag | 1560 |
| aagttgaaaa | acaatagact | caagaaagaa | acaaaccag | tgattcccct | tcctcagata | 1620 |
| ctgggactaa | cagcttcacc | tggtgttgga | ggggccacga | agcaagccaa | agctgaagaa | 1680 |
| cacatttttaa | aactatgtgc | caatcttgat | gcatttacta | ttaaaactgt | taagaaaaac | 1740 |
| cttgatcaac | tgaaaaacca | aatacaggag | ccatgcaaga | agttgccat | gcagatgca | 1800 |
| accagagaag | atccatttaa | agagaaactt | ctagaaataa | tgacaaggat | tcaaacttat | 1860 |
| tgtcaaatga | gtccaatgtc | agatttgga | actcaaccct | atgaacaatg | ggccattcaa | 1920 |
| atggaaaaaa | aagctgcaaa | aaaaggaaat | cgcaaagaac | gtgtttgtgc | agaacatttg | 1980 |
| aggaagtaca | atgaggccct | acaaattaat | gacacaattc | gaatgataga | tgcgtatact | 2040 |

-continued

```
catcttgaaa ctttctataa tgaagagaaa gataagaagt ttgcagtcat agaagatgat    2100
agtgatgagg gtggtgatga tgagtattgt gatggtgatg aagatgagga tgatttaaag    2160
aaacctttga aactggatga aacagataga tttctcatga ctttatttt tgaaaacaat    2220
aaaatgttga aaggctggc tgaaaaccca gaatatgaaa atgaaaagct gaccaaatta    2280
agaaatacca taatggagca atatactagg actgaggaat cagcacgagg aataatcttt    2340
acaaaaacac gacagagtgc atatgcgctt tcccagtgga ttactgaaaa tgaaaatttt    2400
gctgaagtag gagtcaaagc ccaccatctg attggagctg acacagcag tgagttcaaa    2460
cccatgacac agaatgaaca aaaagaagtc attagtaaat ttcgcactgg aaaaatcaat    2520
ctgcttatcg ctaccacagt ggcagaagaa ggtctggata ttaaagaatg taacattgtt    2580
atccgttatg gtctcgtcac caatgaaata gccatggtcc aggcccgtgg tcgagccaga    2640
gctgatgaga gcacctacgt cctggttgct cacagtggtt caggagttat cgaacatgag    2700
acagttaatg atttccgaga gaagatgatg tataaagcta tacattgtgt tcaaaatatg    2760
aaaccagagg agtatgctca taagattttg gaattacaga tgcaaagtat aatggaaaag    2820
aaaatgaaaa ccaagagaaa tattgccaag cattacaaga ataacccatc actaataact    2880
ttcctttgca aaaactgcag tgtgctagcc tgttctgggg aagatatcca tgtaattgag    2940
aaaatgcatc acgtcaatat gaccccagaa ttcaaggaac tttacattgt aagagaaaac    3000
aaagcactgc aaaagaagtg tgccgactat caaataaatg gtgaaatcat ctgcaaatgt    3060
ggccaggctt ggggaacaat gatggtgcac aaaggcttag atttgccttg tctcaaaata    3120
aggaattttg tagtggtttt caaaaataat tcaacaaaga aacaatacaa aaagtgggta    3180
gaattaccta tcacatttcc caatcttgac tattcagaat gctgtttatt tagtgatgag    3240
gattagcact tgattgaaga ttcttttaaa atactatcag ttaaacattt aatatgatta    3300
tgattaatgt attcattatg ctacagaact gacataagaa tcaataaaat gattgtttta    3360
ctctg                                                               3365
```

<210> SEQ ID NO 2
<211> LENGTH: 1025
<212> TYPE: PRT
<213> ORGANISM: homo sapiens

<400> SEQUENCE: 2

```
Met Ser Asn Gly Tyr Ser Thr Asp Glu Asn Phe Arg Tyr Leu Ile Ser
 1               5                  10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125
```

-continued

```
Leu Leu Val Arg Asp Val Leu Asp Lys Cys Met Glu Glu Leu Leu
    130                 135                 140

Thr Ile Glu Asp Arg Asn Arg Ile Ala Ala Ala Glu Asn Asn Gly Asn
145                 150                 155                 160

Glu Ser Gly Val Arg Glu Leu Leu Lys Arg Ile Val Gln Lys Glu Asn
                165                 170                 175

Trp Phe Ser Ala Phe Leu Asn Val Leu Arg Gln Thr Gly Asn Asn Glu
            180                 185                 190

Leu Val Gln Glu Leu Thr Gly Ser Asp Cys Ser Glu Ser Asn Ala Glu
        195                 200                 205

Ile Glu Asn Leu Ser Gln Val Asp Gly Pro Gln Val Glu Glu Gln Leu
    210                 215                 220

Leu Ser Thr Thr Val Gln Pro Asn Leu Glu Lys Glu Val Trp Gly Met
225                 230                 235                 240

Glu Asn Asn Ser Ser Glu Ser Ser Phe Ala Asp Ser Ser Val Val Ser
                245                 250                 255

Glu Ser Asp Thr Ser Leu Ala Glu Gly Ser Val Ser Cys Leu Asp Glu
            260                 265                 270

Ser Leu Gly His Asn Ser Asn Met Gly Ser Asp Ser Gly Thr Met Gly
        275                 280                 285

Ser Asp Ser Asp Glu Glu Asn Val Ala Ala Arg Ala Ser Pro Glu Pro
    290                 295                 300

Glu Leu Gln Leu Arg Pro Tyr Gln Met Glu Val Ala Gln Pro Ala Leu
305                 310                 315                 320

Glu Gly Lys Asn Ile Ile Cys Leu Pro Thr Gly Ser Gly Lys Thr
                325                 330                 335

Arg Val Ala Val Tyr Ile Ala Lys Asp His Leu Asp Lys Lys Lys
            340                 345                 350

Ala Ser Glu Pro Gly Lys Val Ile Val Leu Val Asn Lys Val Leu Leu
        355                 360                 365

Val Glu Gln Leu Phe Arg Lys Glu Phe Gln Pro Phe Leu Lys Lys Trp
    370                 375                 380

Tyr Arg Val Ile Gly Leu Ser Gly Asp Thr Gln Leu Lys Ile Ser Phe
385                 390                 395                 400

Pro Glu Val Val Lys Ser Cys Asp Ile Ile Ile Ser Thr Ala Gln Ile
                405                 410                 415

Leu Glu Asn Ser Leu Leu Asn Leu Glu Asn Gly Glu Asp Ala Gly Val
            420                 425                 430

Gln Leu Ser Asp Phe Ser Leu Ile Ile Ile Asp Glu Cys His His Thr
        435                 440                 445

Asn Lys Glu Ala Val Tyr Asn Asn Ile Met Arg His Tyr Leu Met Gln
    450                 455                 460

Lys Leu Lys Asn Asn Arg Leu Lys Lys Glu Asn Lys Pro Val Ile Pro
465                 470                 475                 480

Leu Pro Gln Ile Leu Gly Leu Thr Ala Ser Pro Gly Val Gly Gly Ala
                485                 490                 495

Thr Lys Gln Ala Lys Ala Glu His Ile Leu Lys Leu Cys Ala Asn
            500                 505                 510

Leu Asp Ala Phe Thr Ile Lys Thr Val Lys Glu Asn Leu Asp Gln Leu
        515                 520                 525

Lys Asn Gln Ile Gln Glu Pro Cys Lys Lys Phe Ala Ile Ala Asp Ala
    530                 535                 540

Thr Arg Glu Asp Pro Phe Lys Glu Lys Leu Leu Glu Ile Met Thr Arg
```

```
                 545                 550                 555                 560
Ile Gln Thr Tyr Cys Gln Met Ser Pro Met Ser Asp Phe Gly Thr Gln
                565                 570                 575
Pro Tyr Glu Gln Trp Ala Ile Gln Met Glu Lys Lys Ala Ala Lys Lys
                580                 585                 590
Gly Asn Arg Lys Glu Arg Val Cys Ala Glu His Leu Arg Lys Tyr Asn
                595                 600                 605
Glu Ala Leu Gln Ile Asn Asp Thr Ile Arg Met Ile Asp Ala Tyr Thr
                610                 615                 620
His Leu Glu Thr Phe Tyr Asn Glu Glu Lys Asp Lys Lys Phe Ala Val
625                 630                 635                 640
Ile Glu Asp Asp Ser Asp Glu Gly Gly Asp Asp Glu Tyr Cys Asp Gly
                645                 650                 655
Asp Glu Asp Glu Asp Asp Leu Lys Lys Pro Leu Lys Leu Asp Glu Thr
                660                 665                 670
Asp Arg Phe Leu Met Thr Leu Phe Phe Glu Asn Asn Lys Met Leu Lys
                675                 680                 685
Arg Leu Ala Glu Asn Pro Glu Tyr Glu Asn Glu Lys Leu Thr Lys Leu
                690                 695                 700
Arg Asn Thr Ile Met Glu Gln Tyr Thr Arg Thr Glu Glu Ser Ala Arg
705                 710                 715                 720
Gly Ile Ile Phe Thr Lys Thr Arg Gln Ser Ala Tyr Ala Leu Ser Gln
                725                 730                 735
Trp Ile Thr Glu Asn Glu Lys Phe Ala Glu Val Gly Val Lys Ala His
                740                 745                 750
His Leu Ile Gly Ala Gly His Ser Ser Glu Phe Lys Pro Met Thr Gln
                755                 760                 765
Asn Glu Gln Lys Glu Val Ile Ser Lys Phe Arg Thr Gly Lys Ile Asn
                770                 775                 780
Leu Leu Ile Ala Thr Thr Val Ala Glu Glu Gly Leu Asp Ile Lys Glu
785                 790                 795                 800
Cys Asn Ile Val Ile Arg Tyr Gly Leu Val Thr Asn Glu Ile Ala Met
                805                 810                 815
Val Gln Ala Arg Gly Arg Ala Arg Ala Asp Glu Ser Thr Tyr Val Leu
                820                 825                 830
Val Ala His Ser Gly Ser Gly Val Ile Glu His Glu Thr Val Asn Asp
                835                 840                 845
Phe Arg Glu Lys Met Met Tyr Lys Ala Ile His Cys Val Gln Asn Met
                850                 855                 860
Lys Pro Glu Glu Tyr Ala His Lys Ile Leu Glu Leu Gln Met Gln Ser
865                 870                 875                 880
Ile Met Glu Lys Lys Met Lys Thr Lys Arg Asn Ile Ala Lys His Tyr
                885                 890                 895
Lys Asn Asn Pro Ser Leu Ile Thr Phe Leu Cys Lys Asn Cys Ser Val
                900                 905                 910
Leu Ala Cys Ser Gly Glu Asp Ile His Val Ile Glu Lys Met His His
                915                 920                 925
Val Asn Met Thr Pro Glu Phe Lys Glu Leu Tyr Ile Val Arg Glu Asn
                930                 935                 940
Lys Ala Leu Gln Lys Lys Cys Ala Asp Tyr Gln Ile Asn Gly Glu Ile
945                 950                 955                 960
Ile Cys Lys Cys Gly Gln Ala Trp Gly Thr Met Met Val His Lys Gly
                965                 970                 975
```

```
Leu Asp Leu Pro Cys Leu Lys Ile Arg Asn Phe Val Val Phe Lys
        980                 985                 990

Asn Asn Ser Thr Lys Lys Gln Tyr Lys Lys Trp Val Glu Leu Pro Ile
        995                 1000                1005

Thr Phe Pro Asn Leu Asp Tyr Ser Glu Cys Cys Leu Phe Ser Asp Glu
        1010                1015                1020

Asp
1025

<210> SEQ ID NO 3
<211> LENGTH: 1036
<212> TYPE: DNA
<213> ORGANISM: homo sapiens
<220> FEATURE:
<221> NAME/KEY: misc_feature
<222> LOCATION: 551
<223> OTHER INFORMATION: n = A,T,C or G

<400> SEQUENCE: 3
gcacattttg gcctacaaag gaccttattg ttaaggcaga acctgctggg aaaacaaaat      60
atccgccgga ggagctttgt agagcgttgg tcttggtgtc agagagaatt cgctttcctt    120
ttctgtttcc cgcggtgtcc ttaaccaaag gcctcctctc ttcacccgcc ccgaccaaaa    180
ggtggcgtct ccctgaggaa actccctccc cgccaggcag attacgttta caaagtcctg    240
agaagagaat cgaaacagaa accaaagtca ggcaaactct gtaagaactg cctgacagaa    300
agctggactc aaagctccta cccgagtgtg cagcaggatc gccccggtcc gggacccag     360 gcgcacaccg cagagtccaa agtgccgcgc ctgccggccg cacctgcctg ccgcggcccc    420
gcgcgccgcc ccgctgccca cctgcccgcc tgcccacctg cccaggtgcg agtgcagccc    480
cgcgcgccgg cctgagagcc ctgtggacaa cctcgtcatt gtcaggcaca gagcggtaga    540
ccctgcttct ntaagtgggc agcggacagc ggcacgcaca tttcacctgt cccgcagaca    600
acagcaccat ctgcttggga gaaccctctc ccttctctga gaaagaaaga tgtcgaatgg    660
gtattccaca gacgagaatt tccgctatct catctcgtgc ttcagggcca gggtgaaaat    720
gtacatccag gtggagcctg tgctggacta cctgaccttt ctgcctgcag aggtgaagga    780
gcagattcag aggacagtcg ccactccgg gaacatgcag gcagttgaac tgctgctgag    840 cacccttggag aagggagtct ggcaccttgg ttggactcgg gaattcgtgg aggccctccg    900
gagaaccggc agccctctgg ccgcccgcta catgaaccct gagctcacgg acttgccctc    960
tccatcgttt gagaacgctc atgatgaata tctccaactg ctgaacctcc ttcagcccac   1020
tctggtggac aagctt                                                    1036

<210> SEQ ID NO 4
<211> LENGTH: 202
<212> TYPE: DNA
<213> ORGANISM: homo sapiens
<220> FEATURE:
<221> NAME/KEY: misc_feature
<222> LOCATION: 33
<223> OTHER INFORMATION: n = A,T,C or G
<220> FEATURE:
<221> NAME/KEY: misc_feature
<222> LOCATION: 73
<223> OTHER INFORMATION: n = A,T,C or G
<220> FEATURE:
<221> NAME/KEY: misc_feature
<222> LOCATION: 107
<223> OTHER INFORMATION: n = A,T,C or G
```

-continued

<400> SEQUENCE: 4

```
cattgaactc ttttaagaa cacaatatat tangcattat ccatcttatt gttgggcaga      60
ggtaaggaaa atntaccaat aattttcatt agtgtggagc attatantcc tgtggaaaga    120
atgctgaagt acaaatgaga atccaaagta ccagtctcag ttctgtcact aattttcaga    180
ataaaattag gcaaatcagt tc                                             202
```

<210> SEQ ID NO 5
<211> LENGTH: 112
<212> TYPE: PRT
<213> ORGANISM: homo sapiens

<400> SEQUENCE: 5

```
Met Ala Glu Gly Asn His Arg Lys Lys Pro Leu Lys Val Leu Glu Ser
  1               5                  10                  15

Leu Gly Lys Asp Phe Leu Thr Gly Val Leu Asp Asn Leu Val Glu Gln
             20                  25                  30

Asn Val Leu Asn Trp Lys Glu Glu Lys Lys Lys Tyr Tyr Asp Ala
         35                  40                  45

Lys Thr Glu Asp Lys Val Arg Val Met Ala Asp Ser Met Gln Glu Lys
     50                  55                  60

Gln Arg Met Ala Gly Gln Met Leu Leu Gln Thr Phe Phe Asn Ile Asp
 65                  70                  75                  80

Gln Ile Ser Pro Asn Lys Lys Ala His Pro Asn Met Glu Ala Gly Pro
                 85                  90                  95

Pro Glu Ser Gly Glu Ser Thr Asp Ala Leu Lys Leu Cys Pro His Glu
            100                 105                 110
```

<210> SEQ ID NO 6
<211> LENGTH: 118
<212> TYPE: PRT
<213> ORGANISM: homo sapiens

<400> SEQUENCE: 6

```
Met Ala Asp Lys Val Leu Lys Glu Lys Arg Lys Leu Phe Ile Arg Ser
  1               5                  10                  15

Met Gly Glu Gly Thr Ile Asn Gly Leu Leu Asp Glu Leu Leu Gln Thr
             20                  25                  30

Arg Val Leu Asn Lys Glu Glu Met Glu Lys Val Lys Arg Glu Asn Ala
         35                  40                  45

Thr Val Met Asp Lys Thr Arg Ala Leu Ile Asp Ser Val Ile Pro Lys
     50                  55                  60

Gly Ala Gln Ala Cys Gln Ile Cys Ile Thr Tyr Ile Cys Glu Glu Asp
 65                  70                  75                  80

Ser Tyr Leu Ala Gly Thr Leu Gly Leu Ser Ala Ala Pro Gln Ala Val
                 85                  90                  95

Gln Asp Asn Pro Ala Met Pro Thr Ser Ser Gly Ser Gly Asn Val
            100                 105                 110

Lys Leu Cys Ser Leu Glu
        115
```

<210> SEQ ID NO 7
<211> LENGTH: 108
<212> TYPE: PRT
<213> ORGANISM: homo sapiens

<400> SEQUENCE: 7

```
Met Ala Ser Asp Asp Leu Ser Leu Ile Arg Lys Asn Arg Met Ala Leu
 1               5                  10                  15

Phe Gln Gln Leu Thr Cys Val Leu Pro Ile Leu Asp Asn Leu Leu Lys
                20                  25                  30

Ala Asn Val Ile Asn Lys Gln Glu His Asp Ile Ile Lys Gln Lys Thr
            35                  40                  45

Gln Ile Pro Leu Gln Ala Arg Glu Leu Ile Asp Thr Ile Leu Val Lys
        50                  55                  60

Gly Asn Ala Ala Ala Asn Ile Phe Lys Asn Cys Leu Lys Glu Ile Asp
 65                  70                  75                  80

Ser Thr Leu Tyr Lys Asn Leu Phe Val Asp Lys Asn Met Lys Tyr Ile
                85                  90                  95

Pro Thr Glu Asp Val Ser Gly Leu Ser Leu Glu Glu
            100                 105
```

<210> SEQ ID NO 8
<211> LENGTH: 107
<212> TYPE: PRT
<213> ORGANISM: homo sapiens

<400> SEQUENCE: 8

```
Glu Ser Asn Asp Leu Leu Ile Arg Lys Asn Arg Met Ala Leu Phe
 1               5                  10                  15

Gln His Leu Thr Cys Val Ile Pro Ile Leu Asp Ser Leu Leu Thr Ala
                20                  25                  30

Gly Ile Ile Asn Glu Gln Glu His Asp Val Ile Lys Gln Lys Thr Gln
            35                  40                  45

Thr Ser Leu Gln Ala Arg Glu Leu Ile Asp Thr Ile Leu Val Lys Gly
        50                  55                  60

Asn Ile Ala Ala Thr Val Phe Arg Asn Ser Leu Gln Glu Ala Glu Ala
 65                  70                  75                  80

Val Leu Tyr Glu His Leu Phe Val Gln Gln Asp Ile Lys Tyr Ile Pro
                85                  90                  95

Thr Glu Asp Val Ser Asp Leu Pro Val Glu Glu
            100                 105
```

<210> SEQ ID NO 9
<211> LENGTH: 115
<212> TYPE: PRT
<213> ORGANISM: homo sapiens

<400> SEQUENCE: 9

```
Met His Pro His His Gln Glu Thr Leu Lys Lys Asn Arg Val Val Leu
 1               5                  10                  15

Ala Lys Gln Leu Leu Leu Ser Glu Leu Leu Glu His Leu Leu Glu Lys
                20                  25                  30

Asp Ile Ile Thr Leu Glu Met Arg Glu Leu Ile Gln Ala Lys Val Gly
            35                  40                  45

Ser Phe Ser Gln Asn Val Glu Leu Leu Asn Leu Leu Pro Lys Arg Gly
        50                  55                  60

Pro Gln Ala Phe Asp Ala Phe Cys Glu Ala Leu Arg Glu Thr Lys Gln
 65                  70                  75                  80

Gly His Leu Glu Asp Met Leu Leu Thr Thr Leu Ser Gly Leu Gln His
                85                  90                  95

Val Leu Pro Pro Leu Ser Cys Asp Tyr Asp Leu Ser Leu Pro Phe Pro
            100                 105                 110
```

-continued

```
Val Cys Glu
        115

<210> SEQ ID NO 10
<211> LENGTH: 50
<212> TYPE: PRT
<213> ORGANISM: homo sapiens

<400> SEQUENCE: 10

Leu Val Asp Lys Leu Val Arg Asp Val Leu Asp Lys Cys Met Glu
1               5                   10                  15

Glu Glu Leu Leu Thr Ile Glu Asp Arg Asn Arg Ile Ala Ala Ala Glu
            20                  25                  30

Asn Asn Gly Asn Glu Ser Gly Val Arg Glu Leu Leu Lys Arg Ile Val
            35                  40                  45

Gln Lys
    50

<210> SEQ ID NO 11
<211> LENGTH: 109
<212> TYPE: PRT
<213> ORGANISM: homo sapiens

<400> SEQUENCE: 11

Met Glu Ala Arg Asp Lys Gln Val Leu Arg Ser Leu Arg Leu Glu Leu
1               5                   10                  15

Gly Ala Glu Val Leu Val Glu Gly Leu Val Leu Gln Tyr Leu Tyr Gln
            20                  25                  30

Glu Gly Ile Leu Thr Glu Asn His Ile Gln Glu Ile Asn Ala Gln Thr
            35                  40                  45

Thr Gly Leu Arg Lys Thr Met Leu Leu Leu Asp Ile Leu Pro Ser Arg
    50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Glu Ala Met Thr Asp
                85                  90                  95

Leu Pro Ala Gly Asp Arg Leu Thr Gly Ile Pro Ser His
            100                 105

<210> SEQ ID NO 12
<211> LENGTH: 406
<212> TYPE: PRT
<213> ORGANISM: mus musculus

<400> SEQUENCE: 12

Met Ser Ala Ser Gln Asp Ser Arg Ser Arg Asp Asn Gly Pro Asp Gly
1               5                   10                  15

Met Glu Pro Glu Gly Val Ile Glu Ser Asn Trp Asn Glu Ile Val Asp
            20                  25                  30

Ser Phe Asp Asp Met Asn Leu Ser Glu Ser Leu Leu Arg Gly Ile Tyr
            35                  40                  45

Ala Tyr Gly Phe Glu Lys Pro Ser Ala Ile Gln Gln Arg Ala Ile Leu
    50                  55                  60

Pro Cys Ile Lys Gly Tyr Asp Val Ile Ala Gln Ala Gln Ser Gly Thr
65                  70                  75                  80

Gly Lys Thr Ala Thr Phe Ala Ile Ser Ile Leu Gln Gln Ile Glu Leu
                85                  90                  95

Asp Leu Lys Ala Thr Gln Ala Leu Val Leu Ala Pro Thr Arg Glu Leu
```

```
                100             105              110
Ala Gln Gln Ile Gln Lys Val Val Met Ala Leu Gly Asp Tyr Met Gly
            115                 120                 125

Ala Ser Cys His Ala Cys Ile Gly Gly Thr Asn Val Arg Ala Glu Val
        130                 135                 140

Gln Lys Leu Gln Met Glu Ala Pro His Ile Ile Val Gly Thr Pro Gly
145                 150                 155                 160

Arg Val Phe Asp Met Leu Asn Arg Arg Tyr Leu Ser Pro Lys Tyr Ile
                165                 170                 175

Lys Met Phe Val Leu Asp Glu Ala Asp Glu Met Leu Ser Arg Gly Phe
            180                 185                 190

Lys Asp Gln Ile Tyr Asp Ile Phe Gln Lys Leu Asn Ser Asn Thr Gln
        195                 200                 205

Val Val Leu Leu Ser Ala Thr Met Pro Ser Asp Val Leu Glu Val Thr
    210                 215                 220

Lys Lys Phe Met Arg Asp Pro Ile Arg Ile Leu Val Lys Lys Glu Glu
225                 230                 235                 240

Leu Thr Leu Glu Gly Ile Arg Gln Phe Tyr Ile Asn Val Glu Arg Glu
                245                 250                 255

Glu Trp Lys Leu Asp Thr Leu Cys Asp Leu Tyr Glu Thr Leu Thr Ile
            260                 265                 270

Thr Gln Ala Val Ile Phe Ile Asn Thr Arg Arg Lys Val Asp Trp Leu
        275                 280                 285

Thr Glu Lys Met His Ala Arg Asp Phe Thr Val Ser Ala Met His Gly
    290                 295                 300

Asp Met Asp Gln Lys Glu Arg Asp Val Ile Met Arg Glu Phe Arg Ser
305                 310                 315                 320

Gly Ser Ser Arg Val Leu Ile Thr Thr Asp Leu Leu Ala Arg Gly Ile
                325                 330                 335

Asp Val Gln Gln Val Ser Leu Val Ile Asn Tyr Asp Leu Pro Thr Asn
            340                 345                 350

Arg Glu Asn Tyr Ile His Arg Ile Gly Arg Gly Gly Arg Phe Gly Arg
        355                 360                 365

Lys Gly Val Ala Ile Asn Met Val Thr Glu Glu Asp Lys Arg Thr Leu
    370                 375                 380

Arg Asp Ile Glu Thr Phe Tyr Asn Thr Ser Ile Glu Glu Met Pro Leu
385                 390                 395                 400

Asn Val Ala Asp Leu Ile
                405

<210> SEQ ID NO 13
<211> LENGTH: 500
<212> TYPE: PRT
<213> ORGANISM: molgula oculata

<400> SEQUENCE: 13

Met Ser Gly Tyr Ser Ser Asp Arg Asp Arg Gly Arg Asp Arg Gly Phe
1               5                   10                  15

Gly Ala Pro Arg Phe Gly Gly Ser Arg Ala Gly Pro Leu Ser Gly Lys
            20                  25                  30

Lys Phe Gly Asn Pro Gly Glu Lys Leu Val Lys Lys Trp Asn Leu
        35                  40                  45

Asp Glu Leu Pro Lys Phe Glu Lys Asn Phe Tyr Gln Glu His Pro Asp
50                  55                  60
```

-continued

```
Leu Ala Arg Arg Thr Ala Gln Glu Val Glu Thr Tyr Arg Arg Ser Lys
 65                  70                  75                  80

Glu Ile Thr Val Arg Gly His Asn Cys Pro Lys Pro Val Leu Asn Phe
                 85                  90                  95

Tyr Glu Ala Asn Phe Pro Ala Asn Val Met Asp Val Ile Ala Arg Gln
            100                 105                 110

Asn Phe Thr Glu Pro Thr Ala Ile Gln Ala Gln Gly Trp Pro Val Ala
        115                 120                 125

Leu Ser Gly Leu Asp Met Val Gly Val Ala Gln Thr Gly Ser Gly Lys
130                 135                 140

Thr Leu Ser Tyr Leu Leu Pro Ala Ile Val His Ile Asn His Gln Pro
145                 150                 155                 160

Phe Leu Glu Arg Gly Asp Gly Pro Ile Cys Leu Val Leu Ala Pro Thr
                165                 170                 175

Arg Glu Leu Ala Gln Gln Val Gln Gln Val Ala Ala Glu Tyr Cys Arg
            180                 185                 190

Ala Cys Arg Leu Lys Ser Thr Cys Ile Tyr Gly Gly Ala Pro Lys Gly
        195                 200                 205

Pro Gln Ile Arg Asp Leu Glu Arg Gly Val Glu Ile Cys Ile Ala Thr
210                 215                 220

Pro Gly Arg Leu Ile Asp Phe Leu Glu Cys Gly Lys Thr Asn Leu Arg
225                 230                 235                 240

Arg Thr Thr Tyr Leu Val Leu Asp Glu Ala Asp Arg Met Leu Asp Met
                245                 250                 255

Gly Phe Glu Pro Gln Ile Arg Lys Ile Val Asp Gln Ile Arg Pro Asp
            260                 265                 270

Arg Gln Thr Leu Met Trp Ser Ala Thr Trp Pro Lys Glu Val Arg Gln
        275                 280                 285

Leu Ala Glu Asp Phe Leu Lys Asp Tyr Ile His Ile Asn Ile Gly Ala
290                 295                 300

Leu Glu Leu Ser Ala Asn His Asn Ile Leu Gln Ile Val Asp Val Cys
305                 310                 315                 320

His Asp Val Glu Lys Asp Glu Lys Leu Ile Arg Leu Met Glu Glu Ile
                325                 330                 335

Met Ser Glu Lys Glu Asn Lys Thr Ile Val Phe Val Glu Thr Lys Arg
            340                 345                 350

Arg Cys Asp Glu Leu Thr Arg Lys Met Arg Arg Asp Gly Trp Pro Ala
        355                 360                 365

Met Gly Ile His Gly Asp Lys Ser Gln Gln Glu Arg Asp Trp Val Leu
370                 375                 380

Asn Glu Phe Lys His Gly Lys Ala Pro Ile Leu Ile Ala Thr Asp Val
385                 390                 395                 400

Ala Ser Arg Gly Leu Asp Val Glu Asp Val Lys Phe Val Ile Asn Tyr
                405                 410                 415

Asp Tyr Pro Asn Ser Ser Glu Asp Tyr Ile His Arg Ile Gly Arg Thr
            420                 425                 430

Ala Arg Ser Thr Lys Thr Gly Thr Ala Tyr Thr Phe Phe Thr Pro Asn
        435                 440                 445

Asn Ile Lys Gln Val Ser Asp Leu Ile Ser Val Leu Arg Glu Ala Asn
450                 455                 460

Gln Ala Ile Asn Pro Lys Leu Leu Gln Leu Val Glu Asp Arg Gly Ser
465                 470                 475                 480

Gly Arg Ser Arg Gly Arg Gly Gly Met Lys Asp Asp Arg Arg Asp Arg
```

```
                485                 490                 495

Tyr Ser Ala Gly
            500

<210> SEQ ID NO 14
<211> LENGTH: 6
<212> TYPE: PRT
<213> ORGANISM: Artificial Sequence
<220> FEATURE:
<223> OTHER INFORMATION: protein domain

<400> SEQUENCE: 14

Thr Gly Ser Gly Lys Thr
1               5

<210> SEQ ID NO 15
<211> LENGTH: 4
<212> TYPE: PRT
<213> ORGANISM: Artificial Sequence
<220> FEATURE:
<223> OTHER INFORMATION: protein domain

<400> SEQUENCE: 15

Asp Glu Cys His
1

<210> SEQ ID NO 16
<211> LENGTH: 5
<212> TYPE: PRT
<213> ORGANISM: Artificial Sequence
<220> FEATURE:
<223> OTHER INFORMATION: protein domain

<400> SEQUENCE: 16

Ala Arg Gly Arg Ala
1               5

<210> SEQ ID NO 17
<211> LENGTH: 10
<212> TYPE: PRT
<213> ORGANISM: Artificial Sequence
<220> FEATURE:
<223> OTHER INFORMATION: protein domain
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 9
<223> OTHER INFORMATION: Xaa = Any Amino Acid

<400> SEQUENCE: 17

Tyr Ile His Arg Ile Gly Arg Xaa Xaa Arg
1               5                   10

<210> SEQ ID NO 18
<211> LENGTH: 8
<212> TYPE: PRT
<213> ORGANISM: Artificial Sequence
<220> FEATURE:
<223> OTHER INFORMATION: protein domain

<400> SEQUENCE: 18

Leu Pro Thr Gly Ser Gly Lys Thr
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: protein domain
<220> FEATURE:
<221> NAME/KEY: VARIANT
<222> LOCATION: 1
<223> OTHER INFORMATION: Xaa = Ala or Gly
<220> FEATURE:
<221> NAME/KEY: VARIANT
<222> LOCATION: 2
<223> OTHER INFORMATION: Xaa = any amino acid
<220> FEATURE:
<221> NAME/KEY: VARIANT
<222> LOCATION: 3
<223> OTHER INFORMATION: Xaa = any amino acid
<220> FEATURE:
<221> NAME/KEY: VARIANT
<222> LOCATION: 5
<223> OTHER INFORMATION: Xaa = any amino acid

<400> SEQUENCE: 19

Xaa Xaa Xaa Gly Xaa Gly Lys Thr
 1               5

<210> SEQ ID NO 20
<211> LENGTH: 4
<212> TYPE: PRT
<213> ORGANISM: Artificial Sequence
<220> FEATURE:
<223> OTHER INFORMATION: protein domain

<400> SEQUENCE: 20

Asp Glu Ala Asp
 1

<210> SEQ ID NO 21
<211> LENGTH: 4
<212> TYPE: PRT
<213> ORGANISM: Artificial Sequence
<220> FEATURE:
<223> OTHER INFORMATION: protein domain

<400> SEQUENCE: 21

Asp Glu Ala His
 1

<210> SEQ ID NO 22
<211> LENGTH: 4
<212> TYPE: PRT
<213> ORGANISM: Artificial Sequence
<220> FEATURE:
<223> OTHER INFORMATION: protein domain
<220> FEATURE:
<221> NAME/KEY: VARIANT
<222> LOCATION: 3
<223> OTHER INFORMATION: Xaa = Any Amino Acid

<400> SEQUENCE: 22

Asp Glu Xaa His
 1

<210> SEQ ID NO 23
<211> LENGTH: 8
<212> TYPE: PRT
<213> ORGANISM: Artificial Sequence
<220> FEATURE:
<223> OTHER INFORMATION: protein domain
<220> FEATURE:
```

```
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Any Amino Acid

<400> SEQUENCE: 23

His Arg Ile Gly Arg Xaa Xaa Arg
 1               5

<210> SEQ ID NO 24
<211> LENGTH: 5
<212> TYPE: PRT
<213> ORGANISM: Artificial Sequence
<220> FEATURE:
<223> OTHER INFORMATION: protein domain

<400> SEQUENCE: 24

Ala Arg Gly Arg Ile
 1               5

<210> SEQ ID NO 25
<211> LENGTH: 6406
<212> TYPE: DNA
<213> ORGANISM: homo sapiens

<400> SEQUENCE: 25
tccactcaat ataaagcttg cactcattct ccaagcccag gtgtgatccg attcttccag     60
tataccaagt caagaacctg ggatacagaa agccctctgt ccttgagaca atgtagaggg    120
tctaactgag cttgttaaca caagccacct atagacagca aaactaaaag atcaccctgt    180
aacacacgcc cactgaggct tcagaagctg taaacatcca ccctagaca ctgccgtggg     240
tcggagcccc acagcctgcc catctgcagg ctcccctaga ggtttgagca gtggggcact    300
gaagaagcga gccacacccc catactgccc aaggtaattt acagattcaa tgccatcccc    360
atcaagctac caatgacttt cttcacagaa ttggaaaaaa ctactttaaa gttcatatgg    420
aaccaaaaaa gagcccgcat cgccaagtca atcctaagcc aaaagaacaa agctggaggc    480
atcaccctac ctgacttcaa acaatactac aaggctacag taaccaaaac agcatggtac    540
tggtaccaaa acagagatat agatcaatgg aacagaacag agccctcaga ataatgccca    600
tatactaca actatctgat cttttgacaaa cctgagaaaa acaagcaatg gggaaagtat    660
tccctattta taaatggtg ctgggaaaac tggctagcca tatgtagaaa gctgaaactg    720
ggttccttcc ttacacctta tacaaaaatc aattcaagat ggattaaaga cttaaacgtt    780
agacctaaaa ccataaaaac cctagaagaa acctaggca ttaccattca ggacatacgc      840
atgggcaagg acttcatgtc taaaacacca aaagcaatgg caacaaaagc caaattgac     900
aaacggtatc taattaaact aaagagcttc tgcacagcaa agaaactac cattagagtg      960
aacaggcaac ctacaaaatg ggagaaaatt ttcgcaacct actcatccga caagggcta    1020
atatccagaa tctacaatga actcaaacaa atttacaaga aaaaaacaaa caccccatc    1080
aaaaagtggg tgaaggacat gaacagacac ttgtcaaaag aagacattta tgcagccaaa    1140
aaacacatga aaaatgctc accatcactg gccatcagag aaatgcaaat caaaaccaca    1200
atgagatacc atctcacacc agttagaatg gcaatcatta aaagtcagg aaacaacagg    1260
tgatggagag gatgtggaga aataggaaca cttttgcact gttggtggga ctgtaaacta    1320
gttcaaccat tgtggaagtc agtgtggtga ttcctcaggg atctagaact agaaatacca    1380
```

```
tttgacccag ccatcccatt actgggtata tactcaaagg actataaatc ttgctgctat    1440
aaagacacat gcacatgtat gtttattgtg gcattattca caatagcaaa gacttggaac    1500
caacccaaat gtccaacagt gatagactgg attaagaaaa tgtggcacac atacaccatg    1560
gaatactatg cagccataaa aaatgatgag ttcatgtcct ttgtagggac atggatgaaa    1620
ttggaaatca tcattctcag taaactatcg caagaacaaa aaaccaaaca ccgcatattc    1680
tcactcatag gtgggaattg aacaatgcga acacatggac acaggaagga gaacatcaca    1740
ctctggggac tgttgtgggg tgggggagg ggggagggat agcattggta gatataccta    1800
atgctagatg acgagttagt gggtgcagcg caccagcatg acacatgtat acatatgtaa    1860
ccaacctgca cattgtgcac atgtacccta aaacttaaag tataataata aataaataaa    1920
taaataaata aataaataaa gtaaaataaa acaattacaa tctagccttt gaggtaaaag    1980
tactgttttt cacaaaaaca tttgcaggta actgtttttg aaaagacttt aagctatgga    2040
aggagtactt gaaaatgaa tgttccaaaa cttatctatt gatacgtgac tttcattttt      2100
tgccaaaact gctatgtaga aaagttttta tatgtgaaaa cttaaaaacc agaattttaa    2160
ttgaattggt gaaagtgatt aggaaattat tatcaagatt tagtgaactt agccataatt    2220
ttttttctat tttaggctta ctactatttt tgaaataaaa agctacgaca gtatcctttt    2280
aataaacttt cctgctaaat cagcctatca gtttcagtta aatggctgaa agtcttgctt    2340
aaagtctcag ttaaatggct agctattata tagtgtttat atgtatgtgt gtatatatat    2400
atatatatat atatatatat atatatatat atatatatat atgtaactaa attttttcctt    2460 tataaattgt gcattctttg aagactagca ccgcaccatc tcttctttaa tttttatata    2520
agcgtagtgg gctggagtca catattgggc acataaacat gccaggctgg tgctagtgtg    2580
ttacagtcta tccttagaac aaacttctga catgatacca gaatctttcc attttacaac    2640
tgatgtattt gaggtgattt tcaaagcac agcaattaag aaatagtatt gagatgtgaa    2700
ctcagacagc ctgaactcag agtctctgtg cttaaccata ccccacactg ccaggttaag    2760
agcatctaac actttaaatt acacaaagca ggctcattat tgatacaaat gagcaaacaa    2820
gtaaaggaac agaacaacaa ttccagggtt tctcactaaa ctaaaattat tgtcattttc    2880
tttgaaaaag acattattgc tatgcatggt cgttaaattg tagtggcagc tcatattgtt    2940
actacttctt aaaaactcaa atgaaaagtt gcataacaat gggaaaatac atagttcagc    3000
aggatctcct gcctcaaaag agaaaggaaa aagaaactta catttgggaa ctggtgaaaa    3060
ggattaaaat gaaacctagt agaagaaact tgacagagga aaacaattaa ttactcaagt    3120
gaaaaacaga aaataaacta aatcatgatg caaaaaatat agatgaaaaa aggatacatt    3180
gtgagagatt gtgtcttggc ttttgtttcc ttaacctcct ttctccaaaa agggtcccat    3240
caagactatg ggagattcct aaaaaagaag tcccttccac ccacacctaa tcctcatcac    3300
tcagacctca tccagcagag agactcctac ttgtgagaaa atatgaattg ttattgttgg    3360
gtattatgtg atgctaatag ggttagagga ggatgactat ttgggaaatc aacctgtgaa    3420
actgtaatat acattattat gtagatttac tatggtcttc agggcattta tcctcacctg    3480
cacattgcat attttttagt cattacttac catctatctt cccactccca ttagaatgtg    3540
aactccataa aagtaggagc tttgttaatt ttattaactg cacctagatc agtgctggtc    3600
atgtaataga tacttaataa acatatttta aatgactaga tgatacaatg aatgatataa    3660
tttgaatgcc aaatatttaa atatctttgg tttaaatgtt tattatttga gaacaggtca    3720
```

-continued

```
aataccaaac atttgatcct ttctcttcca gagcaacaat taagtggtat gaagaaaata    3780
acattaactg gttccccata ttcagtcagc aacccttct cattcccca tgtttgaaac     3840 caagaaacag aaggataagt gccaggaaaa agaatgtttt ttggtttgtt agtttgtgct    3900
ttaacatgtt gaataaaacc cactggcagc tggggatag gagtatgttt ttgcaacagc    3960
cttaaaagat attttcatag acccaatact taaaattaat aatttgagtg cttttgtaga   4020
aacatctaat tggattatcc tctatctggg tacaaggtca tctcccaaaa ttaagtgaaa   4080
aaggagtagg gttctgtgaa gaaacagaaa agaacagtat aaatcaggcc tacctgcaag   4140
cccaaggttt catttacttc aactttcagt gtatttaaca ttatgccagc tgctatggtc   4200
aactcaaata caactcccag gagagatgtc atcaagagcc caccagttgt gagtagtgta   4260
ctagttacta tgtaaatata tcccttcttc aagcagctta caatccttca ggggtagaaa   4320
aagccttgct acataagata attagagaat aaaataagac atgttaccat aaagtgctca   4380
tttggatatt ttgtatgccc ctagtaaaca ctcaccaaga ctctgtactt ctattatcct   4440
gttcaaagca ctatcaggtt ttcctggcct acacagactt tattgaatgt actttgctaa   4500
cagattattt ttcctaaaata tgtctctttg ataacctaaa tgatctctcc atcctttata  4560
taattctgga ccatgagatt ctagttatgg tgcgtatgtg cctaccaccc acagtcacat   4620
gtggctacag aatgccttca gaatgagtag taacctaag gactcacatt tatgtggctt    4680
ctgtaccaaa atgaagctgc cattttcag tgtgaatatg ttttttttct ctcatgacat   4740
agacaaatgt tgatgtttac tacaagttgg tacattagtt gctaattaag ttcctagctg   4800
ctccagccaa aacttgctgt attgaatcca agaaaagaat ggcagctata tcaaaaataa   4860
gttgttgggg gattttttg ttttgtttta taaaggaaa gttgtatatt aaagaatata    4920
gggaacttac aagctgggat ctaggaaact ttaagtcttg gcttccttct aagctgagtt   4980
ggtggttcaa gtccatccac atctgttacc aggtcctggt caaagctgca taaataccag   5040
caatctaaat atgaggcagt aaagttaact gtttattgtt actcactttt tcgaacccac   5100
ctccaaattc ccagggaaac aagttagtgt ttgggaaccc acaggaggtc aggtttattt   5160
taggaaggac ttcctcctgt cttctccaca tctctgcaaa gatgtcttct gagcttcatc   5220
tctcacctgt ccctcgcagt ctcaccaccc tcagccaggc ctgcctacat tcaccagccg   5280
agggtaactc cctgttcacg tccgggtctg tggcagtttc tgttcacttc ccctttggaa   5340
agtcccaaat cacatgcttt tatgccctgc acattttggc ctacaaagga ccttattgtt   5400
aaggcagaac ctgctgggaa aacaaaatat ccgccggagg agctttgcta gagcgttggt   5460
cttggtgtca gagagaattc gctttccttt tctgtttccc gcggtgtcct taaccaaagg   5520
cctcctctct tcacccgccc cgaccaaaag gtggcgtctc cctgaggaaa ctccctcccc   5580
gccaggcaga ttacgtttac aaagtcctga agagaatc gaaacagaaa ccaaagtcag    5640
gcaaactctg taagaactgc ctgacagaaa gctggactca aagctcctac ccgagtgtgc   5700
agcaggatcg ccccggtccg ggaccccagg cgcacaccgc agagtccaaa gtgccgcgcc   5760
tgccggccgc acctgcctgc cgcggccccg cgcgccgccc cgctgcccac ctgcccgcct   5820
gcccacctgc ccaggtgcga gtgcagcccc gcgcgccggc ctgagagccc tgtggacaac   5880
ctcgtcattg tcaggcacag agcggtagac cctgcttctc taagtgggca gcggacagcg   5940
gcacgcacat ttcacctgtc ccgcagacaa cagcaccatc tgcttgggag aaccctctcc   6000
cttctctgag aaagaaagat gtcgaatggg tattccacag acgagaattt ccgctatctc   6060
atctcgtgct tcagggccag ggtgaaaatg tacatccagg tggagcctgt gctggactac   6120
```

```
ctgaccttc   tgcctgcaga  ggtgaaggag  cagattcaga  ggacagtcgc  cacctccggg   6180
aacatgcagg  cagttgaact  gctgctgagc  accttggaga  agggagtctg  gcaccttggt   6240
tggactcggg  aattcgtgga  ggccctccgg  agaaccggca  gccctctggc  cgcccgctac   6300
atgaaccctg  agctcacgga  cttgccctct  ccatcgtttg  agaacgctca  tgatgaatat   6360
ctccaactgc  tgaacctcct  tcagcccact  ctggtggaca  agcttc                   6406
```